US007060459B2

(12) United States Patent
Saus

(10) Patent No.: US 7,060,459 B2
(45) Date of Patent: Jun. 13, 2006

(54) TNF-INDUCIBLE PROMOTERS AND METHODS FOR USING

(76) Inventor: Juan Saus, Fundación Valenciana de Investigaciones Biomédicas, C/ Amadeo de Saboya 4, 46010, Valencia (ES)

( * ) Notice: Subject to any disclaimer, the term of this patent is extended or adjusted under 35 U.S.C. 154(b) by 607 days.

(21) Appl. No.: 10/008,721

(22) Filed: Dec. 7, 2001

(65) Prior Publication Data

US 2003/0082745 A1 May 1, 2003

Related U.S. Application Data

(60) Provisional application No. 60/254,649, filed on Dec. 8, 2000.

(51) Int. Cl.
*C12P 21/06* (2006.01)
*C12N 15/00* (2006.01)
*C07H 21/02* (2006.01)

(52) U.S. Cl. .................. 435/69.1; 435/69.5; 435/320.1; 435/325; 536/23.1; 536/24.1

(58) Field of Classification Search ................ 435/69.1, 435/69.4, 69.5, 70.1, 325, 320.1, 252.3; 536/23.1, 536/24.1
See application file for complete search history.

(56) References Cited

U.S. PATENT DOCUMENTS 6,127,176 A * 10/2000 Stark et al. .................. 435/325

FOREIGN PATENT DOCUMENTS

WO          WO 00/50607          8/2000

OTHER PUBLICATIONS

Aggarwal et al. (2001) TNFα in *Cytokine Reference. A compedium of cytokines and other mediators of host defense* Oppenheim, J.J eds. vol. 1 (Academic Press Ltd.,London), pp. 413-447.
Beck et al. (1992) DNA sequence analysis of 66 kb of the human MHC class II region encoding a cluster of genes for antigen processing. Database Accession No. X66401.
Brenner et al. (1999) Genomic organization of two novel human genes. Database Accession No. Z68129.
Brenner, V., Nyakatura, G., Rosenthal, A. and Platzer, M. (1997) Genomic organization of two novel genes on human Xq28:Compact head to head arrangement of IDHγ and TRAPδ is conserved in rat and mouse. *Genomics* 44, 8-14.
Brayton et al. (1994) Tow genes for de novo purine nucleotide synthesis on human chromosome 4 are closely linked and divergently transcribed. Database Accession No. U00239.
Casciola-Rosen, L.A., Anhalt, G. and Rosen, A. (1994) Autoantigens targeted in systemic lupus erythematosus are clustered in two populations of surface structures on apoptotic keratinocytes. J. Exp. Med. 179, 1317-1330.
Casciola-Rosen, L., & Rosen, A. (1997) Ultraviolet light-induced keratinocyte apoptosis: a potential mechanism for the induction of skin lesions and autoantibody production in LE.Lupus 6, 175-180.
Chen et al. (1984) The functional human dihydrofolate reductase gene. Database Accession No. K01612.
Echtenacher B, Falk W, Mannel DA and Krammer PH (1990) Requirement of endogenous Tumor Necrosis Factor/ Cachectin for recovery from experimental peritonitis. J. Immunol. 145, 3762-3766.
Felmann, M., Bondeson, J., Brennan, F.M., Foxwell, B.M., and Maini, RN.(1999). The rationale for the current boom in anti-TNFα treatment. Is there an effective means to define therapeutic targets for drugs that provide all the benefits of anti-TNFα and minimise hazards? Ann. Rheum. Dis. 58 Suppll. I27-31.
Gavalas, A. and Zalkin, H. (1995) Analysis of the chicken GPAT/AIRC bi-directional promoter for *de novo* purine nucleotide synthesis. J. Biol. Chem. 270, 2403-2410.
Gerlach, V.L., Aravind, L., Gotway, G., Schultz, R.A., Koonin, E.V. and Friedberg, E.C.(1999) Human and mouse homologs of *E. coli* DinB (DNA polymerase IV), members of the UmuC/DinB superfamily Proc. Natl. Acad. Sci. USA 96, 11922-11927.
Gerlach, V.L., Feaver, W.J., Fischhaber, P.L., and Friedberg, E.C.(2001) Purification characterization of pol $_K$, a DNA polymerase encoded by the human *DINB1* gene. J. Biol. Chem. 276, 92-98.
Gonzalez M, Schurmans S, Ramos A, Merino R, Lambert P-H and Merino J. (1995) CD4+T cells determine the ability of spleen cells from F1 hybrid mice to induce neonatal tolerance to alloantigens and autoimmunity in parental mice. Eur. J. Immunol. 25: 1760-1764.
Haines et al. The Multiple Sclerosis Genetics Group (1996) A complete genomic screen for multiple sclerosis underscores a role for the major histocompatability complex. Nature Genet. 13, 469-471.
Hansen, U. and Sharp, P. (1983) Sequences controlling *in vitro* transcription of SV40 promoters. EMBO J. 2, 2293-2303.
Hansen et al. (2000) Genomic structure and chromosomal localisation of the human Hsp60 and Hsp10 genes. Frequent polymorphisms in the human Hsp60 and Hsp10 genes. Database Accession No. AJ250915.

(Continued)

Primary Examiner—Robert S. Landsman
Assistant Examiner—Jegatheesan Seharaseyon
(74) *Attorney, Agent, or Firm*—McDonnell Boehnen Hulbert & Berghoff LLP

(57) ABSTRACT

The present invention provides isolated TNF-inducible promoter sequences, expression vectors containing such promoter sequences, host cells transfected with such expression vectors, as well as methods for using the promoters, vectors, and host cells for identifying candidate compounds for treating or preventing autoimmune disorders or cancer, or for identifying promoters that are regulated by tumor necrosis factor.

13 Claims, 11 Drawing Sheets

OTHER PUBLICATIONS

Johnson, R.E., Prakash, S.and Prakash, L.(2000) The human *DINB1* gene encodes the DNA polymerase polθ. Proc. Natl. Acad. Sci. USA 97, 3838-3843.

Lavia, P., Macleod, D. and Bird, A. (1987) Coincident start sites for divergent transcripts at a randomly selected CpG-rich island of mouse. EMBO J. 6, 2773-2779.

López-Hoyos, M., Carrió, R., Merino, R., Buelta, L., Izui, S., Núñez, G., and Merino, J.(1996). Constitutive expression of Bcl-2 in B cells causes a lethal form of lupuslike autoimmune disease after induction of neonatal tolerance to $H-2^b$ alloantigens. J. Exp. Med. 183, 2523-2531.

López-Hoyos, M., Diez, M.A., Buelta, L., Izui, S., Merino J., and Merino, R.(1999) Overexpression of human Bcl-2 in germinal center B cells induce a new and severe autoimmune syndrome in (C57BL/6×NZW)F1 mice. Arthritis Rheum. 42(9):S393.

Mariyama, M., Kalluri, R. , Hudson, B.G. and Reeders, S.T. (1992) The α4(V) chain of basement membrane collagen . J. Biol. Chem. 267, 1253-1258.

Momota, R., Sugimoto, M., Oohashi, T., Kigasawa, K., Yoshioka, H. and Ninomiya, Y.(1998) Two genes, *COL4A3* and *COL4A4* coding for the human α3(IV) and α4(IV) collagen chains are arranged head-to-head on chromosome 2q36. FEBS Lett. 424, 11-16.

Nadal, M., Moreno, S., Pritchard, M., Preciado, M.A., Estivill, X., and Ramos-Arroyo, M.A.(1997) Down syndrome: characterisation of a case with partial trisomy of chromosome 21 owing to a paternal balanced translocation (15:21) (q26:q22.1) by FISH. J. Med. Genet. 34, 50-54.

Needleman, S.B. and Wunsch, C.D. (1970) A general method applicable to the search for similarities in the amino acid sequence of two proteins. J. Mol. Biol. 48, 443-453.

Ogi et al. (2001) *Homo sapiens* genomic sequence containing DINB1 & GPBP gene. Database Accession No. AB036934, XP-002212797.

O'Hanlon, T.P., Raben, N., and Miller F.W. (1995) A novel gene oriented in a head-to-head configuration with the human histidyl-tRNA synthetase (HRS) gene encodes an mRNA that predicts a polypeptide homologous to HRS. Biochem. Biophys. Res. Commun. 210, 556-566.

Ohashi, E., Bebenek, K., Matsuda, T., Feaver, W.J., Gerlach, V.L., Friedberg, E.C., Ohmori, H. and Kunkel, T.A.(2000) Fidelity and processivity of DNA synthesis by DNA polymerase $_K$, the product of the human *DINB1* gene. J. Biol. Chem. 275, 39678-39684.

Oohashi, T., Ueki, Y., Sugimoto, M. and Ninomiya, Y.(1995). Isolation and structure of the *COL4A6* gene encoding the human α6(IV) collagen chain and comparison with other type IV collagen genes. J. Biol. Chem. 270, 26863-26867.

Pablos, J.L:, Santiago, B., Galindo, M., Carreira, P.E., Ballestin, C. and Gomez-Reino, J.J. (1999) Keratinocyte apoptosis and p. 53 expression in cutaneous lupus and dermatomyositis. J. Pathol. 188, 63-68.

Pöschl, E., Pollner, R. and Künh, K. (1988) The genes for the α1(IV) and α2(IV) chains of human basement membrane collagen type IV are arranged head-to-head and separated by a bi-directional promoter of unique structure. EMBO J. 7, 2687-2695.

Quinones, S., Bernal, D., García-Sogo, M., Elena, S.F. and Saus, J. (1992) Exon/intron structure of the human α3(IV) gene encompassing the Goodpasture antigen (α3(IV)NC1). J. Biol. Chem. 267, 19780-19784.

Raya, A., Revert, F., Navarro, S., and Saus, J. (1999) Characterization of a novel type of serine/threonine kinase that specifically phosphorylates the human Goodpasture antigen J.Biol. Chem. 274, 12642-12649.

Raya, A., Revert-Ros, F., Martinez-Martinez, P., Navarro, S., Roselló, E., Vieites, B., Granero, F., Forteza, J. and Saus, J. (2000) Goodpasture antigen-binding protein, the kinase that phosphorylates the Goodpasture antigen, is an alternatively spliced variant implicated in autoimmune pathogenesis. J. Biol. Chem. 275, 40392-40399.

Remick D, Manohar P, Bolgos G, Rodriguez J, Moldawer L, and Wollenberg G. (1995) Blockade of tumor necrosis factor reduces lipopolysaccharide lethality, but not the lethality of cecal ligation and puncture. Shock, 4, 89-95.

Ruddle et al. (2001) Lymphotoxin α and β. in *Cytokine Reference. A compedium of cytokines and other mediators of host defense* Oppenheim, J.J eds. vol. 1 (Academic Press Ltd.,London), pp. 436-447.

Ryan, M.T., Herd, S.M., Sberna, G., Samuel, M.M., Hoogenraad, N.J. and Hoj, P.B. (1997) The genes encoding mammalian chaperonin 60 and chaperonin 10 are linked head-to-head and share a bi-directional promoter. Gene 196, 9-17.

Saus, J. (1998) in *Goodpasture's Syndrome: Encyclopedia of Immunology* 2nd edn. vol. 2, eds. Delves, P.J., & Roitt, I.M., (Academic Press Ltd., London), pp. 1005-1011.

Shimada, T, Fujii, H. and Lin, H. (1989) A 165-base pair sequence between the dihydrofolate reductase gene and the divergently transcribed upstream gene is sufficient for bi-directional transcriptional activity. J. Biol. Chem. 264, 20171-20174.

Shinya, E. and Shimada, T. (1994) Identification of two initiator elements in the bi-directional promoter of the human dihydrofolate reductase and mismatch repair protein 1 genes. Nucleic Acids Res. 22, 2143-2149.

Sugimoto, M., Oohashi, T., Yoshioka, H., Matsuo, N., and Ninomiya, Y. (1993). cDNA isolation and partial gene structure of the human α4(IV)collagen chain. FEBS Lett. 330, 122-128.

Sugimoto, M., Oohashi, T., and Ninomiya, Y. (1994) The genes *COL4A5* and *COL4A6*, coding for basement membrane collagen chains α5(IV) and α6(IV), are located head-to-head in close proximity on chromosome Xq22 and *COL4A6* is transcribed from two alternative promoters. Proc. Natl. Acad. Sci. USA 91, 11679-11683.

Tang, M., Pham, P., Shen, X., Taylor, J.-S., O'Donnell, M., Woodgate, R. and Goodman, M.F. (2000) Roles of the *E.coli* DNA polymerases IV and V in lesion-targeted and untargeted SOS mutagenesis. Nature 404, 1014-1018.

Tsui, H.W., Mok, S., Souza, L., Marttin, A., and Tsui, F.W.L.(1993) Transcriptional analyses of the gene region that encodes the human histidyl-tRNA synthetase: Identification of a novel bi-directional regulatory element. Gene 131, 201-208.

Utz, P.J., and Anderson, P. (1998) Posttranslational protein modifications, apoptosis, and the bypass of tolerance to autoantigens. Arthritis & Rheum. 41, 1152-1160.

Wagner, J., Gruz, P., Kim, S.-R., Yamada, M., Matsui, K., Fuchs, R.P.P. and Nohmi, T.(1999) The *dinB* gene encodes a novel *E. coli* DNA polymerase, DNA Pol IV, involved in mutagenesis. Mol. Cell 4, 281-286.

Wasylyk, B., Wasylyk, C., Augereau, P. and Chambon, P.(1983) The SV40 72 bp repeat preferentially potentiates transcription starting form proximal natural or substitute promoter elements. Cell 32, 503-514.

Wright, K.L., White, L.C., Kelly, A., Beck, S., Trowsdale, J., and Ting, J.P.-Y. (1995) Coordinate regulation of the human *TAP1* and *LMP2* genes from a shared bi-directional promoter. J. Exp. Med. 181, 1459-1471.

Zhang, Y., Yuan, F., Xin, H., Wu, X., Rajpal, D.K., Yang, D. and Wang, Z.(2000) Human DNA polymerase $\kappa$ synthesizesDNA with extraordinarily low fidelity. Nucleic Acids Res. 28, 4147-4156.

Zhang, Y., Yuan, F., Wu, X., Wang, M., Rechkoblit, O., Taylor, J.-S., Geacintov, N.E. and Wang, Z.(2000) Error-free and error-prone lesion bypass by human DNA polymerase $\kappa$ *in vitro*. Nucleic Acids Res. 28, 4138-4146.

\* cited by examiner

FIGURE 1a

```
ON-GPBP-18m
GGCATGGTTAACGTGGTTCTCAGTAAGATATTCATTTACAACCAAGAGAAAATCCCAGGCTATCATTCACATTCTGTTTTACTTTAAA       90
CCGTACCAATTGCACCAAGAGTCATTCTATAAGTAAATGTGGTTCTCTTTTAGGGTCCGATAGTAGAGTGTAAGAACAAAATGAAATT
                                        XbaI
AACCTTTCTAAGCGTCATTTATTCTCTGACAACCTCAAAATTACTTTCTACAAGCAAACTCTAGAAATCTAGAGATCTTAGAGAAGTGCGTGCT      180
TTGGAAAGATTGCAGTAAATAAGAGACTGTTGGAGTTTTAAATGAAAGATGTTTCGTTTGAGATCTTTAGAATCTCTAGAATTTCACGCACGA
TGTGAGAAGGTACTAAGGAAATTCTTCCTTTAAACGTCAAATGTGAATTCTAACTTCTAATGAGTAAGACCCTGAGATTTACAGCGGTG       270
ACACTCTTCCATGATTCCTTTAAGAAGGAAATTTGCAGTTTACACTTAAGATTGAAGATTACTCATTCTGGGAGCTCTAAATGTCGCCAC
                                                                         ApaI
GTCTGGTGGAAAGAAAACCCTGGCACTAGTAGCTCACAAAACCCCAGCCCATGGTTGAGGCGGAAGCGGCCAGATGCTCCCGGGCTTTC       360
CAGACCACCTTTCTTTTGGGACCGTGATCATCGAGTGTTTTGGGGTACCAACTCGCCTTCGCCGGTCTACGAGGGCCCGAAAG
GACAAGCCCGCCCTGGAAAGCAGGCCCCTGGGCCCCGAAGCCCGGGGCCCAAGCCCGGAGGGTTCGTGATAAACA       450
CTGTTCGGGGGACCCTTTCGTCCGGGGCAGTAGAAGTCGCCTTTCAGAGAAGTGCAGACCCGGGCGTTCGGGCTCCCAAGCACTATTTGT
                                                                        HeLa 4.1 ←
CACAAGGCAAGGATAGAAGCGAGCGAGGGGCTGGTCACGCAACTGTCAAATCGAAGCCCACCACCGACTGACAAGCCCCAAGGGGAC       540
GTGTTCCGTTCCGTTATCTTCGCTCGCTCCCGACCAGTGCGTTGACAGTTGCTTCGGTGGCTGACTGTTCGGGGTTCCCCTG
```

FIGURE 2
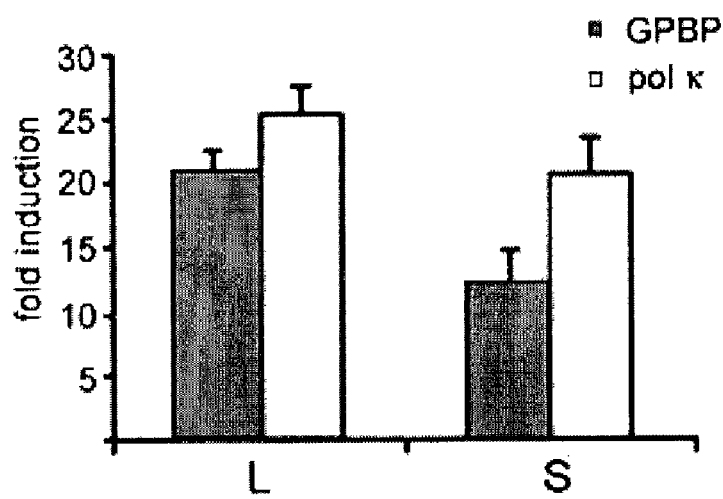
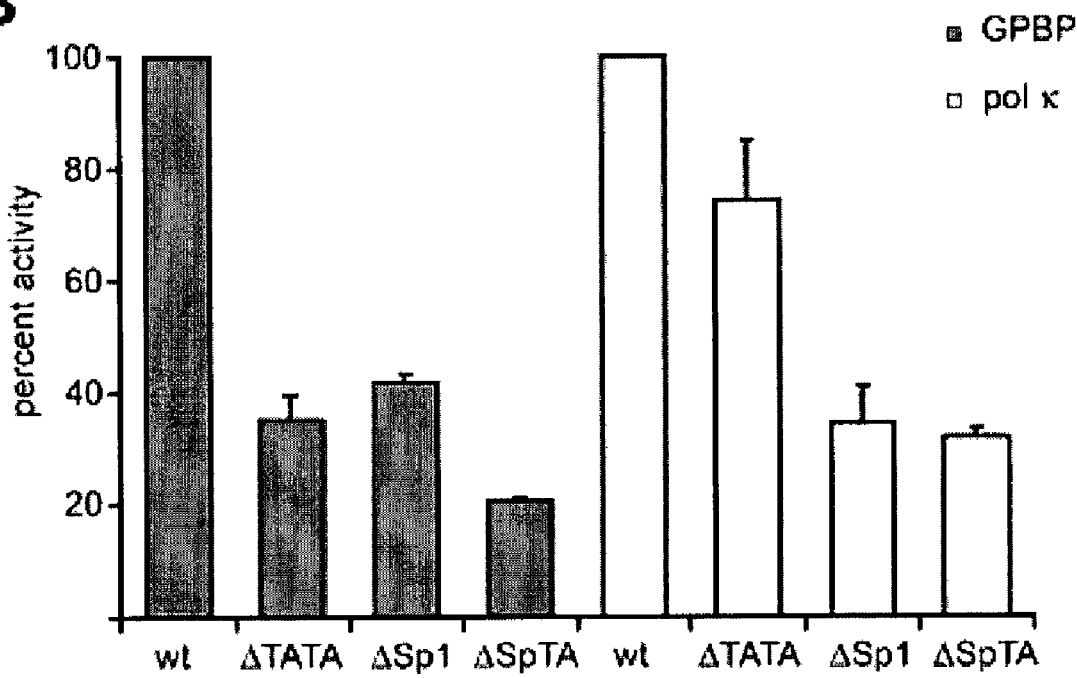

FIGURE 3

| | *COL4A3BP* ▦ | *POLK* ☐ | Alignment map* |
|---|---|---|---|
| *COL4A1-A2*<br>($\alpha_1\alpha_2$)<br>GenBank no. M36963 | Region aligned 469-608<br>$Q=620; E(Q)=591.4\pm17.1$<br>$z=1.6725, P=0.00472$ | Region aligned 583-722<br>$Q=580; E(Q)=571\pm19$<br>$z=0.4737, P=0.3179$ | α1  α2 → ▦ |
| *COL4A3-A4*<br>($\alpha_3\alpha_4$)<br>GenBank no. AF218541 | Region aligned 849-990<br>$Q=674; E(Q)=568.7\pm17.5$<br>$z=6.0171, P<0.0001$ | Region aligned 182-318<br>$Q=641; E(Q)=557.5\pm18.4$<br>$z=4.5380, P<0.0001$ | α3 α4' ▦ α4 → |
| *COL4A5-A6*<br>($\alpha_5\alpha_6$)<br>GenBank no. D28116 | Region aligned 1714-1853<br>$Q=570; E(Q)=524.2\pm18.4$<br>$z=2.4891, P=0.0064$ | Region aligned 440-579<br>$Q=570; E(Q)=527.4\pm17.3$<br>$z=2.4624, P=0.0069$ | α5  α6' → ▦ α6 → |

FIGURE 4

| | *COL4A3BP* ▨ | *POLK* ☐ | Alignment map* |
|---|---|---|---|
| *LMP2-TAP1*<br>GenBank no. X66401 | Region aligned 24579-24718<br>$Q=610; E(Q)=549.9\pm16.9$<br>$z=3.5562, \textbf{P=0.0002}$ | Region aligned 27355-27494<br>$Q=620; E(Q)=582.8\pm18.6$<br>$z=2, P=0.0228$ | *LMP2* ▨ *TAP1* ↑ |
| *MRP1-DHFR*<br>GenBank no. K01612 | Region aligned 849-991<br>$Q=581; E(Q)=557.7\pm20.8$<br>$z=1.1202, P=0.1313$ | Region aligned 704-843<br>$Q=640; E(Q)=553.4\pm18.1$<br>$z=4.7845, \textbf{P<0.0001}$ | *DHFR DHFR'* ↑ ↑ ☐ ☐ ↓ *MRP1* |
| *GPAT-AIRC*<br>GenBank no. U00239 | Region aligned 632-769<br>$Q=554; E(Q)=573.4\pm20.4$<br>$z=-0.9510, P=0.8292$ | Region aligned 561-705<br>$Q=565; E(Q)=549.4\pm18.4$<br>$z=0.8478, P=0.1983$ | |
| *HO3-HRS*<br>GenBank no. M96646 | Region aligned 313-452<br>$Q=600; E(Q)=531\pm17.5$<br>$z=3.9429, \textbf{P<0.0001}$ | Region aligned 214-353<br>$Q=560; E(Q)=557.1\pm16.2$<br>$z=0.1790, P=0.4290$ | *HRS HRS'* ↑ ↑ ▨ ☐ ↓ *HO3* |
| *HSP10-HSP60*<br>GenBank no. AJ250915 | Region aligned 3451-3590<br>$Q=600; E(Q)=546.7\pm16.7$<br>$z=3.1916, \textbf{P=0.0007}$ | Region aligned 3684-3821<br>$Q=594; E(Q)=542.6\pm17.1$<br>$z=3.0058, \textbf{P=0.0013}$ | *HSP10 HSP60* ↑ ↑ ▨ ☐ |
| *IDHG-TRAPD*<br>GenBank no. Z68129 | Region aligned 16283-16422<br>$Q=622; E(Q)=594.8\pm16.5$<br>$z=2.7394, P=0.0031$ | Region aligned 14190-14329<br>$Q=610; E(Q)=601.9\pm15.5$<br>$z=0.5226, P=0.3006$ | |

FIGURE 5
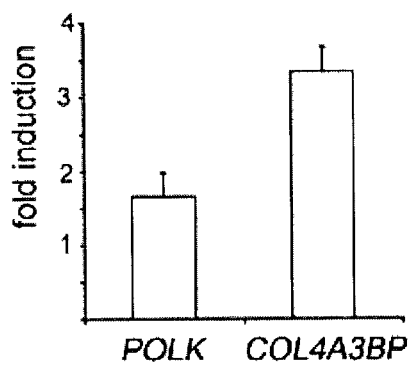
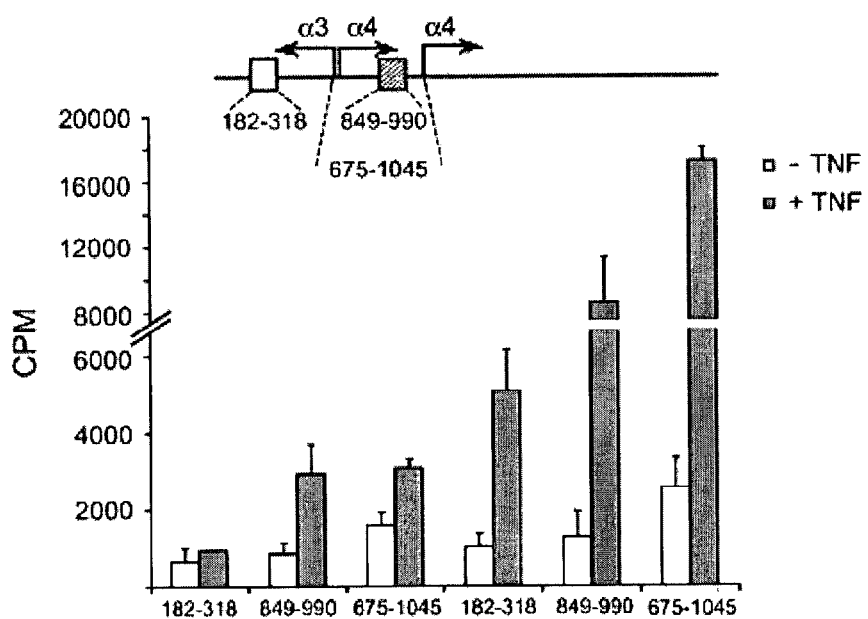
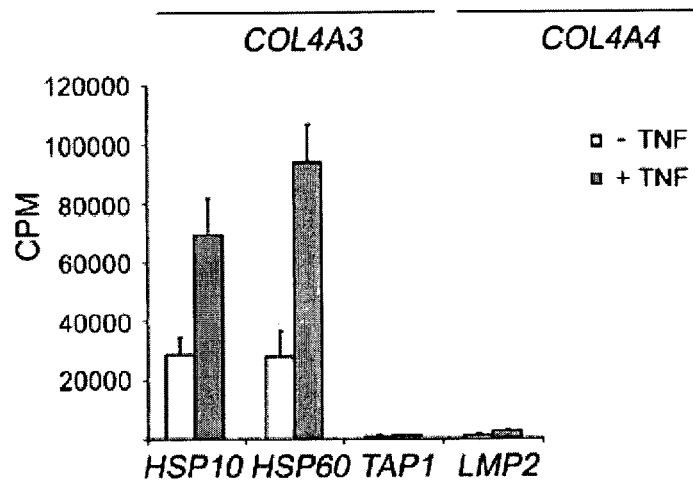

FIGURE 8
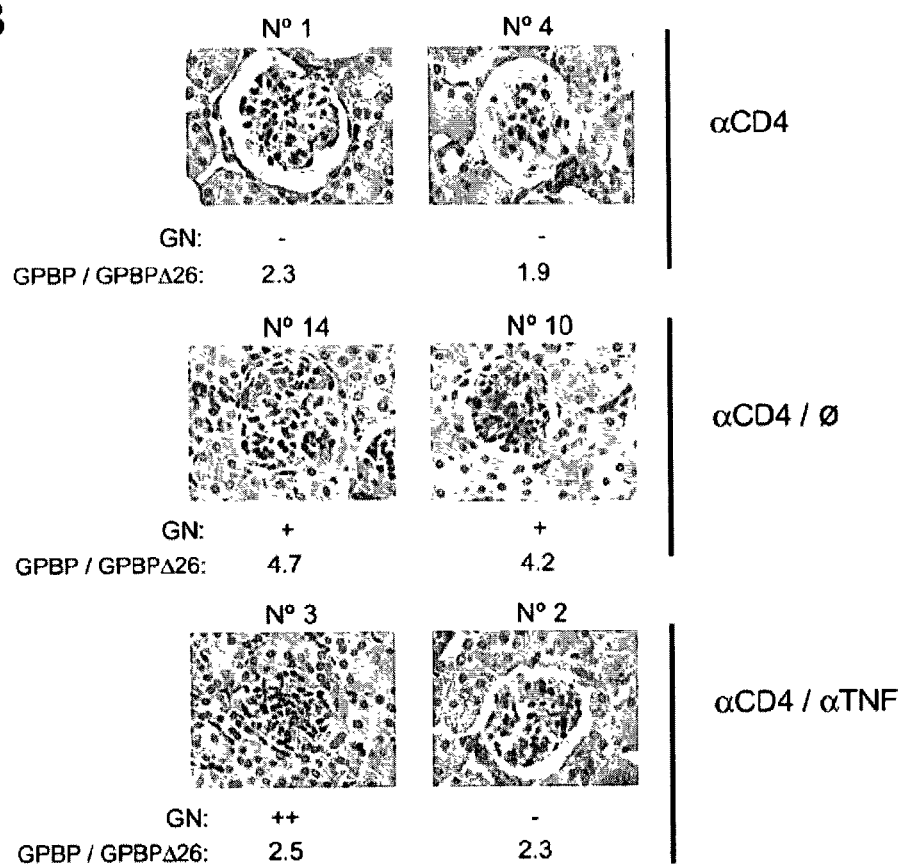
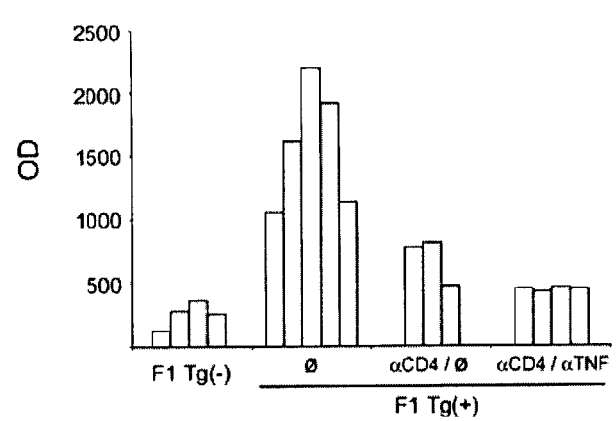

FIGURE 9
A
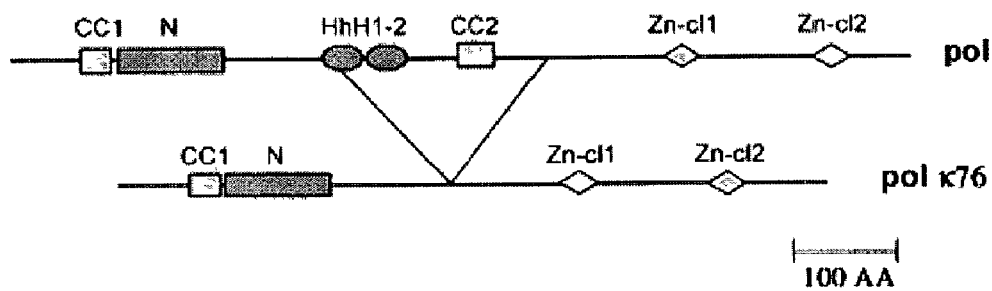
B
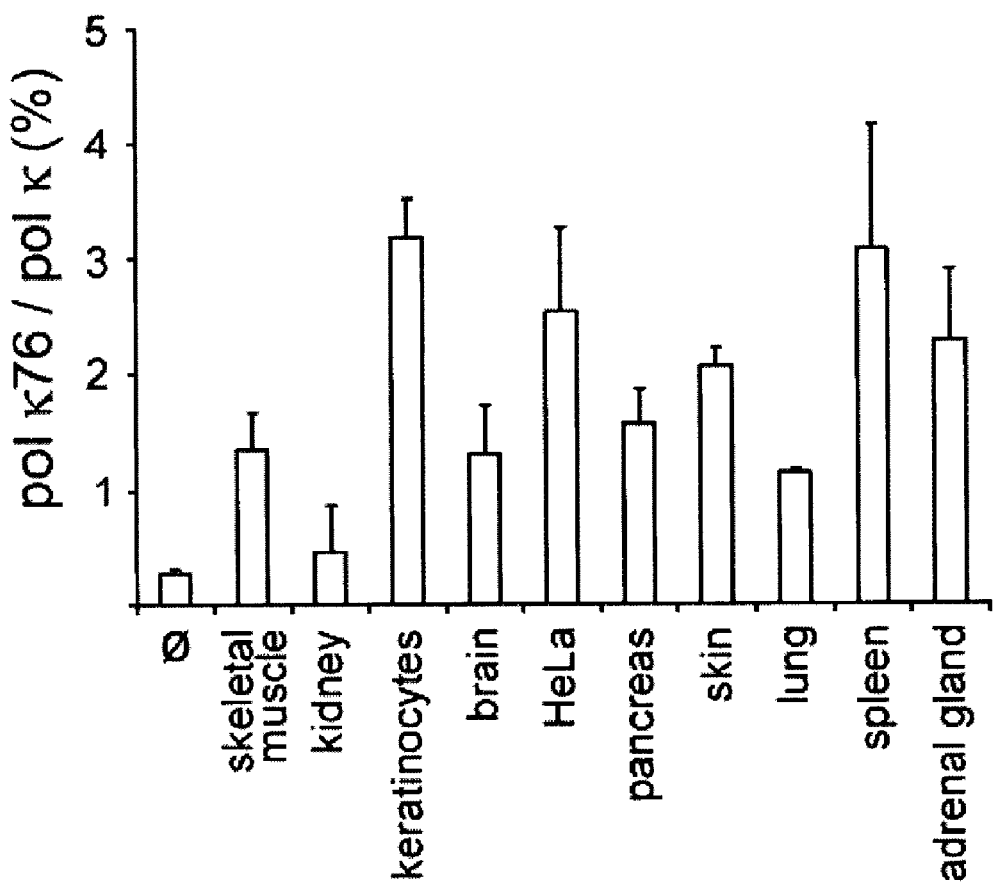

SEQUENCE LISTING

<160> NUMBER OF SEQ ID NOS: 102

<210> SEQ ID NO 1
<211> LENGTH: 2389
<212> TYPE: DNA
<213> ORGANISM: Homo sapiens

<400> SEQUENCE: 1

```
gcaggaagat ggcggcggta gcggaggtgt gagtggacgc gggactcagc ggccggattt     60
tctcttccct tcttttccct tttccttccc tatttgaaat tggcatcgag ggggctaagt    120
tcgggtggca gcgccgggcg caacgcaggg gtcacggcga cggcggcggc ggctgacggc    180
tggaagggta ggcttcattc accgctcgtc ctccttcctc gctccgctcg gtgtcaggcg    240
cggcggcggc gcggcgggcg gacttcgtcc ctcctcctgc tcccccccac accggagcgg    300
gcactcttcg cttcgccatc ccccgaccct tcaccccgag gactgggcgc ctcctccggc    360
gcagctgagg gagcgggggc cggtctcctg ctcggttgtc gagcctccat gtcggataat    420
cagagctgga actcgtcggg ctcggaggag gatccagaga cggagtctgg gccgcctgtg    480
gagcgctgcg gggtcctcag taagtggaca aactacattc atgggtggca ggatcgttgg    540
gtagttttga aaaataatgc tctgagttac tacaaatctg aagatgaaac agagtatggc    600
tgcagaggat ccatctgtct tagcaaggct gtcatcacac ctcacgattt tgatgaatgt    660
cgatttgata ttagtgtaaa tgatagtgtt tggtatcttc gtgctcagga tccagatcat    720
agacagcaat ggatagatgc cattgaacag cacaagactg aatctggata tggatctgaa    780
tccagcttgc gtcgacatgg ctcaatggtg tccctggtgt ctggagcaag tggctactct    840
gcaacatcca cctcttcatt caagaaaggc cacagtttac gtgagaagtt ggctgaaatg    900
gaaacattta gagacatctt atgtagacaa gttgacacgc tacagaagta ctttgatgcc    960

Ytgtgctgatg ctgtctctaa ggatgaactt caagggata agtggtaga agatgatgaa   1020 gatgactttc ctacaacgcg ttctgatggt gacttcttgc atagtaccaa cggcaataaa   1080
gaaaagttat tccacatgt gacaccaaaa ggaattaatg gtatagactt taagggggaa   1140
gcgataactt ttaaagcaac tactgctgga atccttgcaa cactttctca ttgtattgaa   1200
ctaatggtta aacgtgagga cagctggcag aagagactgg ataaggaaac tgagaagaaa   1260
agaagaacag aggaagcata taaaaatgca atgcagaac ttaagaaaaa atcccacttt   1320
ggaggaccag attatgaaga aggccctaac agtctgatta atgaagaaga gttctttgat   1380
gctgttgaag ctgctcttga cagacaagat aaaatagaag aacagtcaca gagtgaaaag   1440
gtgagattac attggcctac atccttgccc tctggagatg cctttctttc tgtggggaca   1500
catagatttg tccaaaagcc ctatagtcgc tcttcctcca tgtcttccat tgatctagtc   1560
```

-continued

```
agtgcctctg atgatgttca cagattcagc tcccaggttg aagagatggt gcagaaccac   1620
atgacttact cattacagga tgtaggcgga gatgccaatt ggcagttggt tgtagaagaa   1680
ggagaaatga aggtatacag aagagaagta aagaaaatg ggattgttct ggatccttta    1740
aaagctaccc atgcagttaa aggcgtcaca ggacatgaag tctgcaatta tttctggaat   1800
gttgacgttc gcaatgactg ggaaacaact atagaaaact tcatgtggt ggaaacatta    1860 gctgataatg caatcatcat ttatcaaaca cacaagaggg tgtggcctgc ttctcagcga   1920
gacgtattat atctttctgt cattcgaaag ataccagcct tgactgaaaa tgaccctgaa   1980
acttggatag tttgtaattt ttctgtggat catgacagtg ctcctctaaa caaccgatgt   2040
gtccgtgcca aaataaatgt tgctatgatt tgtcaaacct tggtaagccc accagaggga   2100
aaccaggaaa ttagcaggga caacattcta tgcaagatta catatgtagc taatgtgaac   2160
cctggaggat gggcaccagc ctcagtgtta agggcagtgg caaagcgaga gtatcctaaa   2220
tttctaaaac gttttacttc ttacgtccaa gaaaaaactg caggaaagcc tattttgttc   2280
tagtattaac aggtactaga agatatgttt tatcttttttt taactttatt tgactaatat   2340
gactgtcaat actaaaattt agttgttgaa agtatttact atgttttt              2389
```

<210> SEQ ID NO 2
<211> LENGTH: 1304
<212> TYPE: DNA
<213> ORGANISM: Homo sapiens

<400> SEQUENCE: 2

```
gacgaaccct ccgggcttgc gggcccagac gtgagagagc tttccgctga agatgacggg     60
cctgctttcc agggcggctt gtcgaaagcc cgggagcatc tggccgcttc cgcctcaacc    120
atgggctggg gttttgtgag ctactagtgc caagggtttt cttttccacca gaccaccgct   180 gtaaatctcg agggtcttac tcattagaag ttagaattca catttgacgt ttaaaggaag    240
aatttcctta gtaccttctc acaagcacgc acttcgcatt tttagatttc tagagttttgc   300 tttgtagaaa gtaattttga ggttgtcaga gaataaatga cgttagaaag gttttttaaag   360 taaaacaaga atgtgagatg atagcctggg attttctctt ggttgtaaat gaatatctta    420
ctgagaacca cgttaaccat gcctgcccct caaagatagg aaaggttgga tatatagaaa    480
ctttctcgta ttagaaatac cgaagtgcag tggttttgtg tgtacaaggg attaggcaat    540
aggaggctat ttttgtttta agactagggt tgaattagca gaaagaccaa tagaagatct    600
aacaactctt gtcagttgtc aaggataact ttgattatga gactttgact ttgtagcttc    660
agtaatttcc tctcgttagc tatttaataa tagtcgattt ccttgtaatt gccaagagta    720
aaatttgtta ttaaacctta gaaagagtac tttcttacta caaggatggg acgataggag    780
cgaaatttcg agtctaaggg aaaacgctgg ccgagtgtgg tggctcacgc ctgtgatccc    840
ggcacttcgg gaggccgagg tgggtggatc acctgaggcc gggagtttga gaccagcctg    900
ggcggcaggg tgggacccg tctctactaa aaatacaaag attagccgag catggtggta     960
ggtgcctgta actccagctc tttatatcct ggtttcaaat ctaggcttga tgaccttctc   1020
ccatatccca gtatcatatt tttttcttcc tgcatggggg attaattacg attctgaatg   1080
gttggtagca tgaagctagg ttatccctat cgtggcaatg atatttaag taggcattgc    1140 caatatttat cttgctttct tttacttttct tcttttctg accatccaca ctccatttat   1200
attgatgagt tctttactaa atatcaatta ttattatatt atgctcatac tgccatgtct   1260
```
tattctgcag ctttgatcct taaggtgact ttgcatatct gtct            1304

<210> SEQ ID NO 3
<211> LENGTH: 955
<212> TYPE: DNA
<213> ORGANISM: Homo sapiens

<400> SEQUENCE: 3
ggcatggtta acgtggttct cagtaagata ttcatttaca accaagagaa aatcccaggc      60
tatcatctca cattcttgtt ttactttaaa aacctttcta acgtcattta ttctctgaca     120
acctcaaaat tactttctac aaagcaaact ctagaaatct aaaaatgcga agtgcgtgct     180
tgtgagaagg tactaaggaa attcttcctt taaacgtcaa atgtgaattc taacttctaa     240
tgagtaagac cctcgagatt tacagcggtg gtctggtgga aagaaaaccc ttggcactag     300
tagctcacaa aaccccagcc catggttgag gcggaagcgg ccagatgctc ccgggctttc     360
gacaagccgc cctggaaagc aggcccgtca tcttcagcgg aaagctctct cacgtctggg     420
cccgcaagcc cggagggttc gtcataaaca cacaaggcaa ggatagaagc gaggccgagg     480
ggctggtcac gcaactgtca acgaagccc acccaccgac tgacaaggcc caaggggac      540
aagcgatccc cgcgcgggat actcacccgt tacctcagga tcgcgactac aactcccagg     600
aggctgcgcg agcgacggac caacgccctt cccagaatgc agcacagctg catccctacc     660
ccgccctctc ctttctccgc tcctcctgct tttctacccg tcgtcacccg ggagagccgg     720
aggtagggtt cgggaggagg atcccgaagg ctcggcgtgt cgcgtcagac gccgggaggg     780
ggacggggcg gggagtagtg ggggagaatg ggaggacgaa ggggagggga aaggacaggg     840
gaggggaggg taaatagtgg gccaggcagg aagatggcgg cggtagcgga ggtgtgagtg     900
gacgcgggac tcagcggccg gattttctct tcccttcttt tccctttttcc ttccc         955

<210> SEQ ID NO 4
<211> LENGTH: 771
<212> TYPE: DNA
<213> ORGANISM: Homo sapiens

<400> SEQUENCE: 4
tctagaaatc taaaaatgcg aagtgcgtgc ttgtgagaag gtactaagga aattcttcct      60
ttaaacgtca atgtgaatt ctaacttcta atgagtaaga ccctcgagat ttacagcggt     120
ggtctggtgg aaagaaaacc cttggcacta gtagctcaca aaaccccagc ccatggttga     180
ggcggaagcg gccagatgct cccgggcttt cgacaagccg cctggaaag caggcccgtc     240
atcttcagcg gaaagctctc tcacgtctgg gcccgcaagc ccggagggtt cgtcataaac     300
acacaaggca aggatagaag cgaggccgag gggctggtca cgcaactgtc aacgaagcc      360
cacccaccga ctgacaaggc ccaaggggga caagcgatcc ccgcgcggga tactcacccg     420
ttacctcagg atcgcgacta caactcccag gaggctgcgc gagcgacgga ccaacgccct     480
tcccagaatg cagcacagct gcatccctac cccgccctct cctttctccg ctcctcctgc     540
tttctaccc gtcgtcaccc gggagagccg gaggtagggt cgggaggag gatcccgaag     600
gctcggcgtg tcgcgtcaga cgccgggagg gggacggggc ggggagtagt ggggagaat      660
gggaggacga aggggagggg aaaggacagg ggaggggagg gtaaatagtg ggccaggcag     720
gaagatggcg gcggtagcgg aggtgtgagt ggacgcggga ctcagcggcc g              771

<210> SEQ ID NO 5
<211> LENGTH: 771

```
<212> TYPE: DNA
<213> ORGANISM: Homo sapiens

<400> SEQUENCE: 5
cggccgctga gtcccgcgtc cactcacacc tccgctaccg ccgccatctt cctgcctggc    60
ccactattta ccctcccctc ccctgtcctt tccccctccc ttcgtcctcc cattctcccc   120
cactactccc cgccccgtcc ccctcccggc gtctgacgcg acacgccgag ccttcgggat   180
cctcctcccg aaccctacct ccggctctcc cgggtgacga cgggtagaaa agcaggagga   240
gcggagaaag gagagggcgg ggtagggatg cagctgtgct gcattctggg aagggcgttg   300
gtccgtcgct cgcgcagcct cctgggagtt gtagtcgcga tcctgaggta acgggtgagt   360
atcccgcgcg gggatcgctt gtccccttgg ggccttgtca gtcggtgggt gggcttcgtt   420
tgacagttgc gtgaccagcc cctcggcctc gcttctatcc ttgccttgtg tgtttatgac   480
gaaccctccg ggcttgcggg cccagacgtg agagagcttt ccgctgaaga tgacgggcct   540
gctttccagg gcggcttgtc gaaagcccgg gagcatctgg ccgcttccgc ctcaaccatg   600
ggctggggtt ttgtgagcta ctagtgccaa gggttttctt tccaccagac caccgctgta   660
aatctcgagg gtcttactca ttagaagtta gaattcacat ttgacgttta aaggaagaat   720
ttccttagta ccttctcaca agcacgcact tcgcattttt agatttctag a            771

<210> SEQ ID NO 6
<211> LENGTH: 140
<212> TYPE: DNA
<213> ORGANISM: Homo sapiens

<400> SEQUENCE: 6
gggttcggga ggaggatccc gaaggctcgg cgtgtcgcgt cagacgccgg gagggggacg    60
gggcggggag tagtggggga gaatgggagg acgaagggga ggggaaagga caggggaggg   120
gagggtaaat agtgggccag                                                140

<210> SEQ ID NO 7
<211> LENGTH: 140
<212> TYPE: DNA
<213> ORGANISM: Homo sapiens

<400> SEQUENCE: 7
ctggcccact atttaccctc ccctcccctg tcctttcccc tcccttcgt cctcccattc     60
tcccccacta ctccccgccc cgtccccctc ccggcgtctg acgcgacacg ccgagccttc   120
gggatcctcc tcccgaaccc                                                140

<210> SEQ ID NO 8
<211> LENGTH: 137
<212> TYPE: DNA
<213> ORGANISM: Homo sapiens

<400> SEQUENCE: 8
gggctagtgg cgaggctgag ggcttcacgc aggtcccgac aggcagcgag cggaagggag    60
caagcgggga tgccccggaa caggtggaat gcgcggggct gggggaagag gcgaggaggg   120
ggcttgtcca gtgccta                                                  137

<210> SEQ ID NO 9
<211> LENGTH: 137
<212> TYPE: DNA
<213> ORGANISM: Homo sapiens
```

-continued

<400> SEQUENCE: 9

```
taggcactgg acaagccccc tcctcgcctc ttcccccagc cccgcgcatt ccacctgttc    60
cggggcatcc ccgcttgctc ccttccgctc gctgcctgtc gggacctgcg tgaagccctc   120
agcctcgcca ctagccc                                                  137
```

<210> SEQ ID NO 10
<211> LENGTH: 142
<212> TYPE: DNA
<213> ORGANISM: Homo sapiens

<400> SEQUENCE: 10

```
tggccactcc ctccaccctg cgcagccacc tccccaccgc gcagccacct ccccaccgca    60
cacccccaaa cgccccacct ccgaccgcac cccacttccc cgcctgggcc cccggaccttt  120
gggagcatca cctccttaac cc                                            142
```

<210> SEQ ID NO 11
<211> LENGTH: 142
<212> TYPE: DNA
<213> ORGANISM: Homo sapiens

<400> SEQUENCE: 11

```
gggttaagga ggtgatgctc ccaaggtccg ggggcccagg cggggaagtg gggtgcggtc    60
ggaggtgggg cgtttggggg tgtgcggtgg ggaggtggct gcgcggtggg gaggtggctg   120
cgcagggtgg agggagtggc ca                                            142
```

<210> SEQ ID NO 12
<211> LENGTH: 371
<212> TYPE: DNA
<213> ORGANISM: Homo sapiens

<400> SEQUENCE: 12

```
aagcggggcc tcccgcagac gccggcgcgc ctcccgttaa tctgggcagg gccgctggcc    60
actccctcca ccctgcgcag ccactcccc accgcgcagc cacctcccca ccgcacaccc   120
ccaaacgccc cacctccgac cgcaccccac ttccccgcct gggcccccgg accttgggag   180
catcacctcc ttaacccctt acctggatc cgcgcccacc tgcccctcag gcgcccagcc   240
ctttctcgcc tcctgggcac gatgcccggg tagaagggac actgcctggt aagttgggag   300
ggagggggta tgagggcggg acctgagcca cgtcttccct cccttgaagc cacaaccaaa   360
aagcctgggt g                                                        371
```

<210> SEQ ID NO 13
<211> LENGTH: 371
<212> TYPE: DNA
<213> ORGANISM: Homo sapiens

<400> SEQUENCE: 13

```
cacccaggct ttttggttgt ggcttcaagg gagggaagac gtggctcagg tcccgccctc    60
atacccctc cctcccaact taccaggcag tgtcccttct acccgggcat cgtgcccagg   120
aggcgagaaa gggctgggcg cctgaggggc aggtgggcgc ggatccaggg taagggggtta  180
aggaggtgat gctcccaagg tccggggggcc caggcgggga agtgggggtgc ggtcggaggt  240
ggggcgtttg ggggtgtgcg gtggggaggt ggctgcgcgg tggggaggtg gctgcgcagg   300
gtggagggag tggccagcgg ccctgcccag attaacggga ggcgcgccgg cgtctgcggg   360
aggccccgct t                                                        371
```

<210> SEQ ID NO 14
<211> LENGTH: 140
<212> TYPE: DNA
<213> ORGANISM: Homo sapiens

<400> SEQUENCE: 14

```
ctggtgccca attttctcca tcacgcacac ccttctcgcc tctccctgcc tcctgccttt      60
ccacttgcac cagtttttccc accccagcct cagggcgggg ctgcctcgtc acttgtctcg    120
gggcagatct gccctacaca                                                 140
```

<210> SEQ ID NO 15
<211> LENGTH: 140
<212> TYPE: DNA
<213> ORGANISM: Homo sapiens

<400> SEQUENCE: 15

```
tgtgtagggc agatctgccc cgagacaagt gacgaggcag ccccgccctg aggctggggt      60
gggaaaactg gtgcaagtgg aaaggcagga ggcagggaga ggcgagaagg gtgtgcgtga    120
tggagaaaat tgggcaccag                                                 140
```

<210> SEQ ID NO 16
<211> LENGTH: 140
<212> TYPE: DNA
<213> ORGANISM: Homo sapiens

<400> SEQUENCE: 16

```
gggctggggg ggcggggctt gtgggtaagg cgggcggagg cggggaccct ccgcccgatg      60
atagggctgg aggaggaagc ggcgggctga agaaggggaa ggtgggaaga gcccagccgg    120
ggctacaaat tgggtgaagc                                                 140
```

<210> SEQ ID NO 17
<211> LENGTH: 140
<212> TYPE: DNA
<213> ORGANISM: Homo sapiens

<400> SEQUENCE: 17

```
gcttcaccca atttgtagcc ccggctgggc tcttcccacc ttcccttct tcagcccgcc       60
gcttcctcct ccagccctat catcgggcgg agggtccccg cctccgcccg ccttacccac    120
aagccccgcc ccccagccc                                                  140
```

<210> SEQ ID NO 18
<211> LENGTH: 140
<212> TYPE: DNA
<213> ORGANISM: Homo sapiens

<400> SEQUENCE: 18

```
ggttgccggt gcagtctaaa actgtggcgg agtgatactc aaattccctt gtgctggtga      60
ggagggggc cttgcacggg gaagagaggg aggaaagtag atctgtagga attgagtgaa     120
gaaaaagttt gcaagtctgg                                                 140
```

<210> SEQ ID NO 19
<211> LENGTH: 140
<212> TYPE: DNA
<213> ORGANISM: Homo sapiens

<400> SEQUENCE: 19

```
ccagacttgc aaactttttc ttcactcaat tcctacagat ctactttcct ccctctcttc    60
cccgtgcaag gccccctcc tcaccagcac aagggaattt gagtatcact ccgccacagt    120
tttagactgc accggcaacc                                                140
```

<210> SEQ ID NO 20
<211> LENGTH: 140
<212> TYPE: DNA
<213> ORGANISM: Homo sapiens

<400> SEQUENCE: 20

```
cggggctgtc tgctgtcaat catccccct accttgggca gccggtagtc tttctcactt    60
tcaggcacct ttccacacaa cagccctaag tatctccaca gcttcacaca cagccccta    120 gagacctata cgctaagacc                                                140
```

<210> SEQ ID NO 21
<211> LENGTH: 140
<212> TYPE: DNA
<213> ORGANISM: Homo sapiens

<400> SEQUENCE: 21

```
ggtcttagcg tataggtctc taaggggctg tgtgtgaagc tgtggagata cttagggctg    60
ttgtgtggaa aggtgcctga aagtgagaaa gactaccggc tgcccaaggt agggggatg    120 attgacagca gacagccccg                                                140
```

<210> SEQ ID NO 22
<211> LENGTH: 140
<212> TYPE: DNA
<213> ORGANISM: Homo sapiens

<400> SEQUENCE: 22

```
cggagccctg gtgtcccggc gcactgcagc cacactcccg ggccgcgcgc tcccgccgcc    60
tcttacccgc gccgcagggt cctccccttt gaggcgccgc ccgcgcaccg ccgggcggga    120 ggggcagcg ccaacaaatt                                                 140
```

<210> SEQ ID NO 23
<211> LENGTH: 140
<212> TYPE: DNA
<213> ORGANISM: Homo sapiens

<400> SEQUENCE: 23

```
aatttgttgg cgctgccccc tcccgcccgg cggtgcgcgg gcggcgcctc aaagggagg    60 accctgcggc gcgggtaaga ggcggcggga gcgcgcggcc cgggagtgtg gctgcagtgc    120
gccgggacac cagggctccg                                                140
```

<210> SEQ ID NO 24
<211> LENGTH: 140
<212> TYPE: DNA
<213> ORGANISM: Homo sapiens

<400> SEQUENCE: 24

```
gaggtgcgca aacgcccgag ttttccctgg tgcgcgggtt ccgcctttgc agtgccctcc    60 accccttcctg gtgtctgacc cgcctccttc ccaggccttt tgttcctgtc ccggaaagcc    120
ggcgtcctgc cgcgcgatgc                                                140
```

<210> SEQ ID NO 25
<211> LENGTH: 140

<210> SEQ ID NO 25
<211> LENGTH: 140
<212> TYPE: DNA
<213> ORGANISM: Homo sapiens

<400> SEQUENCE: 25
gcatcgcgcg gcaggacgcc ggctttccgg gacaggaaca aaaggcctgg gaaggaggcg    60
ggtcagacac caggaagggt ggagggcact gcaaaggcgg aacccgcgca ccagggaaaa   120
ctcgggcgtt tgcgcacctc                                                140

<210> SEQ ID NO 26
<211> LENGTH: 140
<212> TYPE: DNA
<213> ORGANISM: Homo sapiens

<400> SEQUENCE: 26
cgcggcaccg cgtgtgcagg cagctcccac ccacttcccg tcagcccggg ccctgcaatc    60
tgcacaccct gcgcgcgagc cccgcccctc cctacccgcg cagggtgtgc tagcgcgctc   120
agccctctcc ggccggctta                                                140

<210> SEQ ID NO 27
<211> LENGTH: 140
<212> TYPE: DNA
<213> ORGANISM: Homo sapiens

<400> SEQUENCE: 27
taagccggcc ggagagggct gagcgcgcta gcacaccctg cgcgggtagg gaggggcggg    60
gctcgcgcgc aggtgtgca gattgcaggg cccgggctga cgggaagtgg gtgggagctg   120
cctgcacacg cggtgccgcg                                                140

<210> SEQ ID NO 28
<211> LENGTH: 138
<212> TYPE: DNA
<213> ORGANISM: Homo sapiens

<400> SEQUENCE: 28
cggaactcca ggttgtcgcc gcccgcaccc tccagctgga ccgcagagga ggaaggccca    60
ctcgggggtc gcaggagccg gggggaggtg gtgcgggaag ccgcgtacc tgcggggcgg   120
cggcaaggcg tgcgctcg                                                  138

<210> SEQ ID NO 29
<211> LENGTH: 138
<212> TYPE: DNA
<213> ORGANISM: Homo sapiens

<400> SEQUENCE: 29
cgagcgcacg ccttgccgcc gccccgcagg tacgcggcct tcccgcacca cctccccccg    60
gctcctgcga cccccgagtg ggccttcctc ctctgcggtc cagctggagg gtgcgggcgg   120
cgacaacctg gagttccg                                                  138

<210> SEQ ID NO 30
<211> LENGTH: 2026
<212> TYPE: DNA
<213> ORGANISM: Homo sapiens
<220> FEATURE:
<221> NAME/KEY: CDS
<222> LOCATION: (1)..(2016)

<400> SEQUENCE: 30

-continued

| | |
|---|---|
| atg gat agc aca aag gag aag tgt gac agt tac aaa gat gat ctt ctg<br>Met Asp Ser Thr Lys Glu Lys Cys Asp Ser Tyr Lys Asp Asp Leu Leu<br>1               5                   10                  15 | 48 |
| ctt agg atg gga ctt aat gat aat aaa gca gga atg gaa gga tta gat<br>Leu Arg Met Gly Leu Asn Asp Asn Lys Ala Gly Met Glu Gly Leu Asp<br>         20                  25                  30 | 96 |
| aaa gag aaa att aac aaa att ata atg gaa gcc acg aag ggg tcc aga<br>Lys Glu Lys Ile Asn Lys Ile Ile Met Glu Ala Thr Lys Gly Ser Arg<br>     35                  40                  45 | 144 |
| ttt tat gga aat gag ctc aag aaa gaa aag caa gtc aac caa cga att<br>Phe Tyr Gly Asn Glu Leu Lys Lys Glu Lys Gln Val Asn Gln Arg Ile<br>50                  55                  60 | 192 |
| gaa aat atg atg caa caa aaa gct caa atc acc agc caa cag cta aga<br>Glu Asn Met Met Gln Gln Lys Ala Gln Ile Thr Ser Gln Gln Leu Arg<br>65                  70                  75                  80 | 240 |
| aaa gca caa tta cag gtt gac aga ttt gca atg gaa tta gaa caa agc<br>Lys Ala Gln Leu Gln Val Asp Arg Phe Ala Met Glu Leu Glu Gln Ser<br>             85                  90                  95 | 288 |
| cga aat ttg agc aat acc ata gtg cac att gac atg gat gct ttc tat<br>Arg Asn Leu Ser Asn Thr Ile Val His Ile Asp Met Asp Ala Phe Tyr<br>             100                 105                 110 | 336 |
| gca gct gta gaa atg agg gac aat cca gaa ttg aag gat aaa ccc att<br>Ala Ala Val Glu Met Arg Asp Asn Pro Glu Leu Lys Asp Lys Pro Ile<br>         115                 120                 125 | 384 |
| gct gta gga tca atg agt atg ctg tct act tca aat tac cat gca agg<br>Ala Val Gly Ser Met Ser Met Leu Ser Thr Ser Asn Tyr His Ala Arg<br>130                 135                 140 | 432 |
| aga ttt ggt gtt cgt gca gcc atg cca gga ttt att gct aag agg ctg<br>Arg Phe Gly Val Arg Ala Ala Met Pro Gly Phe Ile Ala Lys Arg Leu<br>145                 150                 155                 160 | 480 |
| tgc cca caa ctt ata ata gtg ccc ccc aac ttt gac aaa tac cga gct<br>Cys Pro Gln Leu Ile Ile Val Pro Pro Asn Phe Asp Lys Tyr Arg Ala<br>             165                 170                 175 | 528 |
| gtg agt aaa gag gtt aag gaa ata ctt gct gat tat gat ccc aat ttt<br>Val Ser Lys Glu Val Lys Glu Ile Leu Ala Asp Tyr Asp Pro Asn Phe<br>         180                 185                 190 | 576 |
| atg gcc atg agt ctt gat gaa gcc tac ttg aat ata aca aag cac tta<br>Met Ala Met Ser Leu Asp Glu Ala Tyr Leu Asn Ile Thr Lys His Leu<br>         195                 200                 205 | 624 |
| gaa gaa aga caa aat tgg cct gag gat aaa aga agg tat ttc atc aaa<br>Glu Glu Arg Gln Asn Trp Pro Glu Asp Lys Arg Arg Tyr Phe Ile Lys<br>     210                 215                 220 | 672 |
| atg gga agc tct gta gaa aat gat aat cca gga aag gaa gtt aat aaa<br>Met Gly Ser Ser Val Glu Asn Asp Asn Pro Gly Lys Glu Val Asn Lys<br>225                 230                 235                 240 | 720 |
| ctg agt gag cat gaa cga tcc atc tct cca cta ctt ttt gaa gag agt<br>Leu Ser Glu His Glu Arg Ser Ile Ser Pro Leu Leu Phe Glu Glu Ser<br>             245                 250                 255 | 768 |
| cct tct gat gtg cag ccc cca gga gat cct ttc caa gtg aac ttt gaa<br>Pro Ser Asp Val Gln Pro Pro Gly Asp Pro Phe Gln Val Asn Phe Glu<br>         260                 265                 270 | 816 |
| gaa caa aac aat cct caa ata ctc caa aac tca gtt gtt ttt gga aca<br>Glu Gln Asn Asn Pro Gln Ile Leu Gln Asn Ser Val Val Phe Gly Thr<br>     275                 280                 285 | 864 |
| tca gcc cag gaa gtg gta aag gaa att cgt ttc aga att gag cag aaa<br>Ser Ala Gln Glu Val Val Lys Glu Ile Arg Phe Arg Ile Glu Gln Lys<br>290                 295                 300 | 912 |
| aca aca ctg aca gcc agt gca ggt gtt cgg ata tct agt ttt ccc aat<br>Thr Thr Leu Thr Ala Ser Ala Gly Val Arg Ile Ser Ser Phe Pro Asn<br>305                 310                 315                 320 | 960 |

-continued

| | |
|---|---|
| gaa gag gac agg aaa cac caa caa agg agc att att ggc ttt tta cag<br>Glu Glu Asp Arg Lys His Gln Gln Arg Ser Ile Ile Gly Phe Leu Gln<br>               325                      330                  335 | 1008 |
| gct gga aac caa gcc ctg tca gcc act gag tgt aca tta gag aaa act<br>Ala Gly Asn Gln Ala Leu Ser Ala Thr Glu Cys Thr Leu Glu Lys Thr<br>       340                      345                      350 | 1056 |
| gac aaa gat aag ttt gta aaa cct cta gaa atg tct cat aag aag agt<br>Asp Lys Asp Lys Phe Val Lys Pro Leu Glu Met Ser His Lys Lys Ser<br>               355                      360                  365 | 1104 |
| ttc ttt gat aaa aaa cga tca gaa agg aaa tgg agt cac caa gat aca<br>Phe Phe Asp Lys Lys Arg Ser Glu Arg Lys Trp Ser His Gln Asp Thr<br>370                      375                      380 | 1152 |
| ttt aaa tgt gaa gcc gtg aat aaa caa agt ttc cag aca tca caa cca<br>Phe Lys Cys Glu Ala Val Asn Lys Gln Ser Phe Gln Thr Ser Gln Pro<br>385                      390                      395                  400 | 1200 |
| ttc caa gtt tta aag aag aag atg aat gag aat ttg gaa ata tca gag<br>Phe Gln Val Leu Lys Lys Lys Met Asn Glu Asn Leu Glu Ile Ser Glu<br>                      405                      410                  415 | 1248 |
| aat tca gat gac tgt cag ata ctt acc tgt cct gtt tgc ttt agg gct<br>Asn Ser Asp Asp Cys Gln Ile Leu Thr Cys Pro Val Cys Phe Arg Ala<br>               420                      425                  430 | 1296 |
| caa ggg tgc atc agt ctg gaa gcc ttg aat aaa cat gta gat gaa tgt<br>Gln Gly Cys Ile Ser Leu Glu Ala Leu Asn Lys His Val Asp Glu Cys<br>       435                      440                      445 | 1344 |
| ctt gat gga cct tca atc agt gaa aac ttt aaa atg ttc tcg tgt tca<br>Leu Asp Gly Pro Ser Ile Ser Glu Asn Phe Lys Met Phe Ser Cys Ser<br>450                      455                      460 | 1392 |
| cat gtt tct gct acc aaa gtt aac aag aaa gaa aat gtt cct gct tct<br>His Val Ser Ala Thr Lys Val Asn Lys Lys Glu Asn Val Pro Ala Ser<br>465                      470                      475                  480 | 1440 |
| tca ctt tgt gag aag caa gat tat gaa gcc cat cca aaa att aaa gaa<br>Ser Leu Cys Glu Lys Gln Asp Tyr Glu Ala His Pro Lys Ile Lys Glu<br>                      485                      490                  495 | 1488 |
| ata tct tca gta gat tgt ata gct tta gta gat act ata gat aac tca<br>Ile Ser Ser Val Asp Cys Ile Ala Leu Val Asp Thr Ile Asp Asn Ser<br>               500                      505                  510 | 1536 |
| tct aaa gca gaa agc ata gat gct tta agt aat aag cat agc aag gaa<br>Ser Lys Ala Glu Ser Ile Asp Ala Leu Ser Asn Lys His Ser Lys Glu<br>       515                      520                      525 | 1584 |
| gaa tgt tct agt ctc cca agc aag tct ttt aat att gaa cac tgt cat<br>Glu Cys Ser Ser Leu Pro Ser Lys Ser Phe Asn Ile Glu His Cys His<br>530                      535                      540 | 1632 |
| cag aat tct tct tct act gtt tca ttg gaa aac gaa gat gtt gga tca<br>Gln Asn Ser Ser Ser Thr Val Ser Leu Glu Asn Glu Asp Val Gly Ser<br>545                      550                      555                  560 | 1680 |
| ttt aga caa gaa tac cgc cag cct tac tta tgt gaa gtg aaa aca ggc<br>Phe Arg Gln Glu Tyr Arg Gln Pro Tyr Leu Cys Glu Val Lys Thr Gly<br>                      565                      570                  575 | 1728 |
| caa gct cta gtt tgt cct gtt tgt aac gta gaa caa aag act tca gat<br>Gln Ala Leu Val Cys Pro Val Cys Asn Val Glu Gln Lys Thr Ser Asp<br>               580                      585                  590 | 1776 |
| cta acc ctg ttc aat gtg cat gtg gat gtt tgc tta aat aaa agt ttt<br>Leu Thr Leu Phe Asn Val His Val Asp Val Cys Leu Asn Lys Ser Phe<br>       595                      600                      605 | 1824 |
| atc caa gaa tta aga aag gat aaa ttt aac cca gtt aat caa ccc aaa<br>Ile Gln Glu Leu Arg Lys Asp Lys Phe Asn Pro Val Asn Gln Pro Lys<br>610                      615                      620 | 1872 |
| gaa agc tcc aga agt act ggt agc tca agt gga gta cag aag gct gta<br>Glu Ser Ser Arg Ser Thr Gly Ser Ser Ser Gly Val Gln Lys Ala Val | 1920 |

```
                    625                 630                 635                 640
aca aga aca aaa agg cca gga ttg atg aca aag tac tca aca tca aag              1968
Thr Arg Thr Lys Arg Pro Gly Leu Met Thr Lys Tyr Ser Thr Ser Lys
                    645                 650                 655 aaa ata aaa cca aac aat ccc aaa cat acc ctt gat ata ttt ttt aag              2016
Lys Ile Lys Pro Asn Asn Pro Lys His Thr Leu Asp Ile Phe Phe Lys
                660                 665                 670 taagtcgacc                                                                   2026

<210> SEQ ID NO 31
<211> LENGTH: 672
<212> TYPE: PRT
<213> ORGANISM: Homo sapiens

<400> SEQUENCE: 31

Met Asp Ser Thr Lys Glu Lys Cys Asp Ser Tyr Lys Asp Asp Leu Leu
 1               5                  10                  15

Leu Arg Met Gly Leu Asn Asp Asn Lys Ala Gly Met Glu Gly Leu Asp
             20                  25                  30

Lys Glu Lys Ile Asn Lys Ile Ile Met Glu Ala Thr Lys Gly Ser Arg
         35                  40                  45

Phe Tyr Gly Asn Glu Leu Lys Lys Glu Lys Gln Val Asn Gln Arg Ile
     50                  55                  60

Glu Asn Met Met Gln Gln Lys Ala Gln Ile Thr Ser Gln Gln Leu Arg
 65                  70                  75                  80

Lys Ala Gln Leu Gln Val Asp Arg Phe Ala Met Glu Leu Glu Gln Ser
                 85                  90                  95

Arg Asn Leu Ser Asn Thr Ile Val His Ile Asp Met Asp Ala Phe Tyr
            100                 105                 110

Ala Ala Val Glu Met Arg Asp Asn Pro Glu Leu Lys Asp Lys Pro Ile
        115                 120                 125

Ala Val Gly Ser Met Ser Met Leu Ser Thr Ser Asn Tyr His Ala Arg
    130                 135                 140

Arg Phe Gly Val Arg Ala Ala Met Pro Gly Phe Ile Ala Lys Arg Leu
145                 150                 155                 160

Cys Pro Gln Leu Ile Ile Val Pro Pro Asn Phe Asp Lys Tyr Arg Ala
                165                 170                 175

Val Ser Lys Glu Val Lys Glu Ile Leu Ala Asp Tyr Asp Pro Asn Phe
            180                 185                 190

Met Ala Met Ser Leu Asp Glu Ala Tyr Leu Asn Ile Thr Lys His Leu
        195                 200                 205

Glu Glu Arg Gln Asn Trp Pro Glu Asp Lys Arg Arg Tyr Phe Ile Lys
    210                 215                 220

Met Gly Ser Ser Val Glu Asn Asp Asn Pro Gly Lys Glu Val Asn Lys
225                 230                 235                 240

Leu Ser Glu His Glu Arg Ser Ile Ser Pro Leu Leu Phe Glu Glu Ser
                245                 250                 255

Pro Ser Asp Val Gln Pro Pro Gly Asp Pro Phe Gln Val Asn Phe Glu
            260                 265                 270

Glu Gln Asn Asn Pro Gln Ile Leu Gln Asn Ser Val Val Phe Gly Thr
        275                 280                 285

Ser Ala Gln Glu Val Val Lys Glu Ile Arg Phe Arg Ile Glu Gln Lys
    290                 295                 300

Thr Thr Leu Thr Ala Ser Ala Gly Val Arg Ile Ser Ser Phe Pro Asn
305                 310                 315                 320
```

```
Glu Glu Asp Arg Lys His Gln Gln Arg Ser Ile Ile Gly Phe Leu Gln
            325                 330                 335

Ala Gly Asn Gln Ala Leu Ser Ala Thr Glu Cys Thr Leu Glu Lys Thr
            340                 345                 350

Asp Lys Asp Lys Phe Val Lys Pro Leu Glu Met Ser His Lys Lys Ser
            355                 360                 365

Phe Phe Asp Lys Arg Ser Glu Arg Lys Trp Ser His Gln Asp Thr
370                 375                 380

Phe Lys Cys Glu Ala Val Asn Lys Gln Ser Phe Gln Thr Ser Gln Pro
385                 390                 395                 400

Phe Gln Val Leu Lys Lys Met Asn Glu Asn Leu Glu Ile Ser Glu
            405                 410                 415

Asn Ser Asp Asp Cys Gln Ile Leu Thr Cys Pro Val Cys Phe Arg Ala
            420                 425                 430

Gln Gly Cys Ile Ser Leu Glu Ala Leu Asn Lys His Val Asp Glu Cys
            435                 440                 445

Leu Asp Gly Pro Ser Ile Ser Glu Asn Phe Lys Met Phe Ser Cys Ser
450                 455                 460

His Val Ser Ala Thr Lys Val Asn Lys Lys Glu Asn Val Pro Ala Ser
465                 470                 475                 480

Ser Leu Cys Glu Lys Gln Asp Tyr Glu Ala His Pro Lys Ile Lys Glu
            485                 490                 495

Ile Ser Ser Val Asp Cys Ile Ala Leu Val Asp Thr Ile Asp Asn Ser
            500                 505                 510

Ser Lys Ala Glu Ser Ile Asp Ala Leu Ser Asn Lys His Ser Lys Glu
            515                 520                 525

Glu Cys Ser Ser Leu Pro Ser Lys Ser Phe Asn Ile Glu His Cys His
            530                 535                 540

Gln Asn Ser Ser Ser Thr Val Ser Leu Glu Asn Glu Asp Val Gly Ser
545                 550                 555                 560

Phe Arg Gln Glu Tyr Arg Gln Pro Tyr Leu Cys Glu Val Lys Thr Gly
            565                 570                 575

Gln Ala Leu Val Cys Pro Val Cys Asn Val Glu Gln Lys Thr Ser Asp
            580                 585                 590

Leu Thr Leu Phe Asn Val His Val Asp Val Cys Leu Asn Lys Ser Phe
            595                 600                 605

Ile Gln Glu Leu Arg Lys Asp Lys Phe Asn Pro Val Asn Gln Pro Lys
            610                 615                 620

Glu Ser Ser Arg Ser Thr Gly Ser Ser Gly Val Gln Lys Ala Val
625                 630                 635                 640

Thr Arg Thr Lys Arg Pro Gly Leu Met Thr Lys Tyr Ser Thr Ser Lys
            645                 650                 655

Lys Ile Lys Pro Asn Asn Pro Lys His Thr Leu Asp Ile Phe Phe Lys
            660                 665                 670

<210> SEQ ID NO 32
<211> LENGTH: 1335
<212> TYPE: DNA
<213> ORGANISM: Homo sapiens

<400> SEQUENCE: 32
tgagagagct ttccgctgaa gatgacgggc ctgctttcca gggcggcttg tcgaaagccc      60
gggagcatct ggccgcttcc gcctcaacca tgggctgggg ttttgtgagc tactagtgcc     120
```

-continued

```
aagggttttc tttccaccag accaccgctg taaatctcga gggtcttact cattagaagt        180
tagaattcac atttgacgtt taaaggaaga atttccttag taccttctca caagcacgca        240
cttcgcattt ttagatttct agagtttgct ttgtagaaag taattttgag gttgtcagag        300
aataaatgac gttagaaagg tttttaaagt aaaacaagaa tgtgagatga tagcctggga        360 tttctcttg gttgtaaatg aatatcttac tgagaaccac gttaaccatg cctgcccctc         420
aaagatagga aaggttggat atatagaaac tttctcgtat tagaaatacc gaagtgcagt       480
ggttttgtgt gtacaaggga ttaggcaata ggaggctatt tttgttttaa gactagggtt        540
gaattagcag aaagaccaat agaagatcta acaactcttg tcagttgtca aggataactt        600
tgattatgag actttgactt tgtagcttca gtaatttcct ctcgttagct attttaatat        660
agtcgatttc cttgtaattg ccaagagtaa aatttgttat taaaccttag aaagagtact       720
ttcttactac aaggatggga cgataggagc gaaatttcga gtctaaggga aaacgctggc        780
cgagtgtggt ggctcacgcc tgtaatccca gcacttcggg aggccgaggt gggtggatca        840
cctgaggccg ggagtttgag accagcctgg gcaacaagat ttttcttcat ccctttactt       900
tgagtctgtg gatgtcattg catgtgatat ggtctcctg aagacagcat accattggat         960
tttgcttctt tatccaagtt atcattctgt ctttttaattg gggtgtgcat tcaagataag      1020
tttataccat ggatagcaca aaggagaagt gtgacagtta caaagatgat cttctgctta      1080
ggatgggact taatgataat aaagcaggaa tggaaggatt agataaagag aaaattaaca      1140
aaattataat ggaagccacg aagggtccca gattttatgg aaatgagctc aagaaagaaa      1200
agcaagtcaa ccaacgaatt gaaaatatga tgcaacaaaa agctcaaatc accagccaac      1260
agctaagaaa agcacaatta caggttgaca gatttgcaat ggaattagaa caaagccgaa      1320
atttgagcaa tacca                                                        1335
```

<210> SEQ ID NO 33
<211> LENGTH: 105
<212> TYPE: DNA
<213> ORGANISM: Mus musculus

<400> SEQUENCE: 33

```
gggagcgtcg cgagccgccg ggaggggccc ggggcggggt ggaggagga tgggaggacg         60 gaggggaggg agctgagaga ggagggaggg taaatagtgg acccg                       105
```

<210> SEQ ID NO 34
<211> LENGTH: 105
<212> TYPE: DNA
<213> ORGANISM: Mus musculus

<400> SEQUENCE: 34

```
cgggtccact atttaccctc cctcctctct cagctccctc ccctccgtcc tcccatcctc         60
cctccacccc gccccgggcc cctccgggcg ctcgcgacg ctccc                         105
```

<210> SEQ ID NO 35
<211> LENGTH: 140
<212> TYPE: DNA
<213> ORGANISM: Homo sapiens

<400> SEQUENCE: 35

```
ccctgcttat atagatgacc ccctccccga gactctgaca gacccaggtc acaggcagtc        60
ctcacctgct cctgacaccc ccggcccctc agtgctgctc tctctagcca ccgagctgaa       120
gtactgagga gcccctacct                                                   140
```

<210> SEQ ID NO 36
<211> LENGTH: 140
<212> TYPE: DNA
<213> ORGANISM: Homo sapiens

<400> SEQUENCE: 36

```
aggtagggc tcctcagtac ttcagctcgg tggctagaga gagcagcact gaggggccgg      60
gggtgtcagg agcaggtgag gactgcctgt gacctgggtc tgtcagagtc tcgggagggg    120
ggtcatctat ataagcaggg                                                140
```

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence:
      Primer ON-GPBP-6c

<400> SEQUENCE: 37

```
ctcgctcgcc cagggaagga aaagggaaaa gaaggga                              37
```

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence:
      Primer ON-GPBP-14c

<400> SEQUENCE: 38

```
ctgcctggcc cactatttac c                                               21
```

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence:
      Primer ON-GPBP-18m

<400> SEQUENCE: 39

```
ggcatggtta acgtggttct c                                               21
```

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence:
      Primer ON-XbaG/Bpro1m

<400> SEQUENCE: 40

```
gactctagag ggttcgggag gaggatcccg                                      30
```

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence:
      Primer ON-XbaG/Bpro1c

<400> SEQUENCE: 41

```
gactctagac tggcccacta tttaccctcc                                      30
```

-continued

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence:
      Primer ON-SP1Del

<400> SEQUENCE: 42
cgccgggagg gggacgtagt gggggagaat                                    30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence:
      Primer ON-TATADel

<400> SEQUENCE: 43
caggggaggg gagggggtggg ccagtctaga                                   30

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence:
      Primer ON-DIN2c

<400> SEQUENCE: 44
ggattattgc acttgccttc ac                                            22

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence:
      Primer ON-DIN5'm

<400> SEQUENCE: 45
aaaggatcca tggatagcac aaaggag                                       27

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence:
      Primer ON-DIN-THc

<400> SEQUENCE: 46
aaaaaagtcg acttacttaa aaatatatc aagggt                              36

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence:
      Primer ON-DINB1-R2

<400> SEQUENCE: 47
tggtattgct caaatttcgg c                                             21

```
<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence:
      Primer ON-GPBP-39c

<400> SEQUENCE: 48
tgagagagct ttccgctg                                                  18

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence:
      Primer ON-LMPTAP1m

<400> SEQUENCE: 49
atgtctagat gtgtagggca gatctgccc                                      29

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence:
      Primer ON-LMPTAP1c

<400> SEQUENCE: 50
atgtctagac tggtgcccaa ttttctcca                                      29

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence:
      Primer ON-HSP1m

<400> SEQUENCE: 51
atgtctagat aagccggccg gagagggct                                      29

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence:
      Primer ON-HSP1c

<400> SEQUENCE: 52
atgtctagac gcggcaccgc gtgtgcagg                                      29

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence:
      Primer ON-SA3A4m

<400> SEQUENCE: 53
gactctagag ggttaaggag gtgatgctcc c                                   31
```

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence:
      Primer ON-SA3A4c

<400> SEQUENCE: 54
gactctagat ggccactccc tccaccctgc gc                                    32

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence:
      Primer ON-INGA3A4m

<400> SEQUENCE: 55
gactctagac acccaggctt tttggttgtg gc                                    32

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence:
      Primer ON-INGA3A4c

<400> SEQUENCE: 56
gactctagaa agcggggcct cccgcagacg c                                     31

<210> SEQ ID NO 57
<211> LENGTH: 29
<212> TYPE: DNA
<213> ORGANISM: Artificial Sequence
<220> FEATURE:
<223> OTHER INFORMATION: Description of Artificial Sequence:
      Primer ON-S2A3A4m

<400> SEQUENCE: 57
atgtctagat aggcactgga caagccccc                                        29

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence:
      Primer ON-S2A3A4c

<400> SEQUENCE: 58
atgtctagag ggctagtggc gaggctgag                                        29

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:
      Primer ON-IDH-F1

<400> SEQUENCE: 59
cacagagggc gagtacagca                                                  20

<210> SEQ ID NO 60

```
<211> LENGTH: 21
<212> TYPE: DNA
<213> ORGANISM: Artificial Sequence
<220> FEATURE:
<223> OTHER INFORMATION: Description of Artificial Sequence:
      Primer ON-IDH-R1

<400> SEQUENCE: 60
tgatcttcag gctctccacc a                                         21

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence:
      Primer ON-TRAPD-F1

<400> SEQUENCE: 61
gggtccagaa catggctctc                                           20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:
      Primer ON-TRAPD-R1

<400> SEQUENCE: 62
acatcctggc ctcgagtgac                                           20

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence:
      Primer ON-LMP2-F2

<400> SEQUENCE: 63
gcagcatata agccaggcat g                                         21

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:
      Primer ON-LMP2-R2

<400> SEQUENCE: 64
tggccagagc aatagcgtct                                           20

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence:
      Primer ON-TAP1-F2

<400> SEQUENCE: 65
gccgcctcac tgactggat                                            19

<210> SEQ ID NO 66
<211> LENGTH: 21
```

```
<212> TYPE: DNA
<213> ORGANISM: Artificial Sequence
<220> FEATURE:
<223> OTHER INFORMATION: Description of Artificial Sequence:
      Primer ON-TAP1-R2

<400> SEQUENCE: 66
tcgagtgaag gtatcggctg a                                              21

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence:
      Primer ON-DHFR-F1

<400> SEQUENCE: 67
cctgtggagg aggaggtgg                                                 19

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence:
      Primer ON-DHFR-R1

<400> SEQUENCE: 68
ccgattcttc cagtctacgg g                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence:
      Primer ON-MSH3-F1

<400> SEQUENCE: 69
tgggtaaagg ttggaagcac a                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence:
      Primer ON-MSH3-R1

<400> SEQUENCE: 70
aaaaggagag tgaaagcggc t                                              21

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence:
      Primer ON-HO3-F2

<400> SEQUENCE: 71
gagctgttgt ccctccgct                                                 19

<210> SEQ ID NO 72
<211> LENGTH: 20
<212> TYPE: DNA
```

```
<213> ORGANISM: Artificial Sequence
<220> FEATURE:
<223> OTHER INFORMATION: Description of Artificial Sequence:
      Primer ON-HO3-R2

<400> SEQUENCE: 72
ggccagataa cgagcaaagg                                                     20

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence:
      Primer ON-HARS-F2

<400> SEQUENCE: 73
aggtggcgaa actcctgaaa c                                                   21

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence:
      Primer ON-HARS-R2

<400> SEQUENCE: 74
tgctttcatc aggacccagc                                                     20

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence:
      Primer ON-Hsp10-F1

<400> SEQUENCE: 75
ggagggagta atggcaggac a                                                   21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence:
      Primer ON-Hsp10-R1

<400> SEQUENCE: 76
agcagcactc ctttcaacca a                                                   21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence:
      Primer ON-Hsp60-F1

<400> SEQUENCE: 77
gcctttggtc ataatcgctg a                                                   21

<210> SEQ ID NO 78
<211> LENGTH: 21
<212> TYPE: DNA
<213> ORGANISM: Artificial Sequence
```

```
<220> FEATURE:
<223> OTHER INFORMATION: Description of Artificial Sequence:
      Primer ON-Hsp60-R1

<400> SEQUENCE: 78
tgccacaacc tgaagaccaa c                                           21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence:
      Primer ON-COL4A1-F1

<400> SEQUENCE: 79
gctctacgtg caaggcaatg a                                           21

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence:
      Primer ON-COL4A1-R1

<400> SEQUENCE: 80
attgtgctga acttgcgcag                                             20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence:
      Primer ON-COL4A2-F1

<400> SEQUENCE: 81
gaaaagggtg acgtagggca                                             20

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence:
      Primer ON-COL4A2-R1

<400> SEQUENCE: 82
ggtgtctgat ggaatcccgt t                                           21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence:
      Primer ON-GP-F1

<400> SEQUENCE: 83
ggagacagtg gatcacctgc a                                           21

<210> SEQ ID NO 84
<211> LENGTH: 21
<212> TYPE: DNA
<213> ORGANISM: Artificial Sequence
<220> FEATURE:
```

```
<223> OTHER INFORMATION: Description of Artificial Sequence:
      Primer ON-GP-R1

<400> SEQUENCE: 84
tgctgtggtt tgactgtgtc g                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence:
      Primer ON-COL4A4-F1

<400> SEQUENCE: 85
cttgccttcc cgtatttagc a                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence:
      Primer ON-COL4A4-R1

<400> SEQUENCE: 86
ggatctgtcg tttctctggg c                                              21

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence:
      Primer ON-COL4A5-F1

<400> SEQUENCE: 87
catcgaatgt catgggaggg                                                20

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence:
      Primer ON-COL4A5-R1

<400> SEQUENCE: 88
agttgccagc caaaagctgt a                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence:
      Primer ON-COL4A6-F1

<400> SEQUENCE: 89
tttgggctag actaccggac a                                              21

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence:
```

-continued

Primer ON-COL4A6-R1

<400> SEQUENCE: 90
tctctatgga cccgagggct                                         20

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence:
      Primer ON-GPBP-F1

<400> SEQUENCE: 91
ctgaatccag cttgcgtcg                                          19

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence:
      Primer ON-GPBP-R1

<400> SEQUENCE: 92
gcagagtagc cacttgctcc                                         20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence:
      Primer ON-DinB1-F3

<400> SEQUENCE: 93 gcccccaac tttgacaaat                                          20

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence:
      Primer ON-DinB1-R3

<400> SEQUENCE: 94
gcttcatcaa gactcatggc c                                       21

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence:
      Primer ON-hGAPDH-F1

<400> SEQUENCE: 95
gaaggtgaag gtcggagtc                                          19

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence:
      Primer ON-hGAPDH-R1

```
<400> SEQUENCE: 96
gaagatggtg atgggatttc                                               20

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence:
      Primer ON-GPBP-26-1F

<400> SEQUENCE: 97
gctgttgaag ctgctcttga ca                                            22

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence:
      Primer ON-mGPBP-26-1R

<400> SEQUENCE: 98
ccatttcttc aacctttgt acaa                                           24

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence:
      Primer ON-GPBPe26-1R

<400> SEQUENCE: 99
cttgggagct gaatctgtga a                                             21

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence:
      Primer ON-huDINB-76-F1

<400> SEQUENCE: 100
ccagtgcagg tgttcggata                                               20

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence:
      Primer ON-huDINB-76-R1

<400> SEQUENCE: 101
tttccagcct gtaaaaagcc a                                             21

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence:
      Primer ON-hGPBP-26-1R
```

-continued

```
<400> SEQUENCE: 102
ccatctcttc aaccttttgg aca                                              23
```

TNF-INDUCIBLE PROMOTERS AND METHODS FOR USING

CROSS REFERENCE

This application claims priority to U.S. provisional application Ser. No. 60/254,649, filed Dec. 8, 2000.

FIELD OF THE INVENTION

The present invention relates to the fields of gene regulation, autoimmunity, cancer, and apoptosis.

BACKGROUND OF THE INVENTION

Tumor necrosis factor α and β (collectively referred to as "TNF") are two different cytokines with similar biological effects that are secreted primarily by macrophages and TH1 cells in response to various inflammatory stimuli, including parasitic, bacterial, and viral infection [see Ref. 12 for a review]. While TNF is known to exert many biological effects, it is known to be the mediator whereby cytolytic immune cells induce fatal injury to their targets via induction of apoptosis or necrosis/lysis However, excessive TNF production or exposure, in concert with other inflammatory cytokines, can lead to severe side effects, including shock, cachexia and autoimmune responses, such as rheumatoid arthritis, insulin-dependent diabetes mellitus, Crohn's disease, glomerulonephritis (renal disease), systemic lupus erythematosus and multiple sclerosis.

Effective anti-TNF based therapeutic approaches have been demonstrated in the treatment of several autoimmune conditions, including rheumatoid arthritis and Crohn's disease, and are presently at the clinical trial stage [12,43]. Anti-TNF based therapy has also been shown to have therapeutic effects on experimental allergic encephalomyelitis (EAE), an animal model for multiple sclerosis. However, when a similar therapy was used in human clinical trials with multiple sclerosis patients, the beneficial effects were not obtained, and a clinical worsening was observed. These contradictory results may be due to the multiple and distinct TNF biological as well as immunological actions, which vary between tissues and also between species. For example, TNF has been shown to be involved in both blocking and promoting tumorigenesis and metastasis, and at the site of its anti-cancer action, it is believed to be responsible for the wasting and anemia characteristic of these patients [12 and references therein].

Thus, it would be useful to develop therapeutic options for autoimmune conditions that interfere with TNF-induced autoimmunity, but which do not augment the immune response, and thus worsen the autoimmune process. For example, it would be useful to be able to identify common transcription factors, that regulate the expression of genes known to be induced by TNF, and which are involved in autoimmune disorder development and progression, in order to design therapeutic interventions to inhibit the activity of such factors, and thereby provide more effective therapies for autoimmune disorders.

SUMMARY OF THE INVENTION

In one aspect, the present invention provides an isolated promoter sequence that can promote the expression of an operatively linked coding region in a TNF-inducible manner, consisting of an isolated sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29, SEQ ID NO:33, SEQ ID NO:34, SEQ ID NO:35, SEQ ID NO:36

In another embodiment, the present invention provides an expression vector comprising an isolated promoter sequence that can modulate the expression of an operatively linked coding region in a TNF-inducible manner, consisting of an isolated sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29, SEQ ID NO:33, SEQ ID NO:34, SEQ ID NO:35, SEQ ID NO:36. In a preferred embodiment, the vector further comprises one or more cloning sites in which to sub-clone a protein-encoding nucleic acid sequence of interest so as to be operatively linked with the promoter sequence.

In a further embodiment, the present invention provides recombinant host cells transfected with one or more of the expression vectors disclosed herein, which can be used to identify compounds that modify TNF induction of protein-encoding sequences operatively linked to the promoter sequences disclosed herein.

In another aspect, the present invention provides methods for identifying candidate compounds for treating or preventing autoimmune disorders or cancer, comprising providing one or more recombinant host cell according to the invention, wherein the recombinant host cell is transfected with at least one of the expression vectors of the invention, which comprise at least one of the TNF-inducible promoter sequences of the invention operably linked to a detectable reporter gene; contacting the recombinant host cell with TNF in the presence or absence of one or more test compounds, determining reporter gene expression levels; and identifying those test compounds that modify TNF-induced reporter gene expression, wherein such modification identifies a test compound as a candidate for the treatment or prevention of autoimmunity or cancer. In an alternative embodiment, the method comprises identifying compounds that modify constitutive reporter gene expression driven by the promoter sequences of the invention, wherein such modification identifies a test compound as a candidate for the treatment or prevention of autoimmunity or cancer.

In a further aspect, the present invention provides methods for identifying promoters that are regulated by tumor necrosis factor, wherein the method comprises aligning one or more known test sequences to be evaluated with a comparison sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29, SEQ ID NO:33, SEQ ID NO:34, SEQ ID NO:35, SEQ ID NO:36, and identifying those test sequences that align with the comparison sequence

BRIEF DESCRIPTION OF THE FIGURES

FIGS. 1A and 1B. Head-to-head arrangement of human POLK and COL4A3BP. The 955-bp between ON-GPBP-18m and ON-GPBP6c (GenBank accession no AF315603) (SEQ ID NO:2) are written in capital letters. In boldface the position and sequence of the two oligonucleotides, the restriction sites used to generate LpromPolκ, LpromGPBP, or the construct from which the ribonucleotide probes are derived, and the DNA sequences which conform to the transcriptional elements identified by the TFSEARCH version 1.3. This DNA fragment contains the first exon of POLK (box), part of the first exon of COL4A3BP and the exon sequence of POLK contained in HeLa 4.1 (open boxes). The 5' end and the transcriptional direction of HeLa 4.1. are indicated with arrows. The 140-bp present in Sprom-Polk and SpromGPBP is highlighted in gray.

FIGS. 2A and 2B. The POLK/COL4A3BP intergene region contains a bidirectional promoter. In A, NIH 3T3 cells were transfected with either pΦGH, Lprom (L bars), or Sprom (S bars) constructs, along with the β-galactosidase expressing vector. Results are expressed as the quotient (fold) of the reporter gene expression of the promoter constructs versus empty vector (pΦGH) after normalization with the corresponding β-galactosidase expression values. We represent the mean of two independent experiments done in duplicate, ±S.D. In B, NIH 3T3 cells were transfected as in A with SpromGPBP or SpromPolκ(wt), or with mutants thereof in which the TATA box (ΔTATA), the Sp1 site (ΔSp1), or both (ΔSpTA) were deleted. Transcriptional activity was estimated as in A and results are expressed as percent activity with respect to the wild type promoter, which was set at 100%, and are the mean±S.D of three experiments done in duplicate.

FIG. 3. Alignment of each orientation of the 140-bp POLK/COL4A3BP promoter region with the corresponding regions of COL4A genes. The parameters of each individual alignment, and those that are significant, are shown in the map therein. Nucleotide numbering and map represent the DNA according to the GenBank accession numbers and the bend arrows mark the position and direction of the transcription start sites of the indicated gene.

FIG. 4. Alignment of each orientation of the 140-bp POLK/COL4A3BP promoter region with the corresponding regions of other bi-directional promoters. In the Table we show the parameters of each individual alignment and those that are significant, as well as that of IDGH-TRAP, which maps 3' end of TRAP are shown in the map therein. Nucleotide numbering and map represent the DNA according to the GenBank accession numbers and the bend arrows mark the position and direction of the transcription start sites of the indicated gene.

FIGS. 5A, 5B and 5C, TNFα/β induce the 140-bp promoter of POLK/COL4A3BP and the homologous regions in other bidirectional promoters in transient gene expression assays. In A, NIH 3T3 cells were transfected with Sprom-Polk and SpromGPBP constructs along with β-galactosidase expressing vector and cells were induced with recombinant human counterparts of TNFα (10 ng/ml) or TNFβ (50 ng/ml). Results are expressed as the quotient (fold) of the reporter gene expression of the induced versus non-induced promoter constructs previous normalization with the corresponding β-galactosidase expression values. We represent the mean of four independent experiments done by duplicated ±S.D. In B, we represent the nucleotide sequence of the COL4A3/COL4A4 contained in AF218541 (SEQ ID NOS:8–13) as in the alignment map of FIG. 3 and we indicate the nucleotide which transcriptional activity was assayed as in A. For these purposes the indicated nucleotides from AF218541 in the indicated transcriptional orientation were individually transfected and further induced as in A. Results are expressed as reporter gene expression in c.p.m. (counts per minute) after normalization with β-galactosidase activity. We represent the mean of three independent experiments done by duplicated ±S.D. In C, the region of HSP10/HSP60 (SEQ ID NOS:26–27) or LMP2/TAP1 (SEQ ID NOS:14–15) homologous with the COL4A3BP orientation of POLK/COL4A3BP promoter (FIG. 4) were individually cloned and assayed as in B.

FIGS. 8A, 8B and 8C, The relative increase of GPBP expression in response to TNF is a phenomenon with pathogenic consequences in a lupus prone mice model. In A, the kidney of female NZW, a male B6-Bcl-2-Tg(+) were paraffin-embedded and stained with GPBP-specific antibodies or mRNA prepared and the ratio of GPBP/GPBPΔ26 determined as in FIG. 7. The presence of glomerulonephritis (GN) in the kidneys was evaluated histologically according to glomerular celulariry and graded from absence (−) to discrete (+) moderate (++) or severe (+++). In B, the kidneys of (NZW×B6)F1Tg(+) mice treated with anti-CD4 (αCD4), treated with anti-CD4 and further maintained without treatment (αCD4/Ø), or treated with anti-CD4 and further treated with anti-TNF (αCD4/αTNF) were analyzed as in A. In A we present representative stainings and average values for GPBP/GPBPΔ26 whereas in B we present two examples for each case (N°1,2,3,4,10 and 14) in which one kidney was used for mRNA determinations and other for morphological studies. In C, the levels of anti-ssDNA autoantibodies in the sera of a number of six month old (NZW×B6Tg(+))F1 mice were determined by ELISA using an alkaline phosphatase-based conjugate. In the histogram each bar represent the values for each individual animal. Represented are non-trangenic F1 [F1Tg(−)], and transgenic F1 [F1Tg(+)] untreated (Ø) or treated with anti-CD4 for three month and then untreated [αCD4/Ø] or treated with anti-CD4 for three month and then treated with anti-TNF [αCD4/αTNF].

FIGS. 9A and 9B. Pol κ76 is a novel alternatively spliced form of pol κ preferentially expressed in keratinocytes which interacts with GIP a tumor suppressor gene product also interacting with GPBP In A, we schematized in a diagram the structural features of pol κ76 in comparison with pol κ. The predicted coiled-coil motifs (CC1 and CC2) previously unrecognized, and the features described in Ref. 5 for pol κ including nucleotidyl transferase domain (N), helix-haipin-helix (HhH1–2) and Zn cluster (Zn-cl1 and Zn-cl2) are indicated. The protein region of pol κ not present in pol κ76 is denoted by the convergent lines. In B, the mRNA levels for pol κ76 and for all of the pol κ molecular species known were estimated by Real Time PCR as described in Material and Methods in the indicated human cells and tissues. Values are expressed as the percentage of pol κ76 with respect total pol κ. With (Ø) we represent the non-specific amplification of pol κ standard plasmid using the pair of oligonucleotides employed for pol κ76 quantification. Values represent the mean±S.D. of four determinations done on two different samples.

DETAILED DESCRIPTION OF THE INVENTION

Figure 1B:
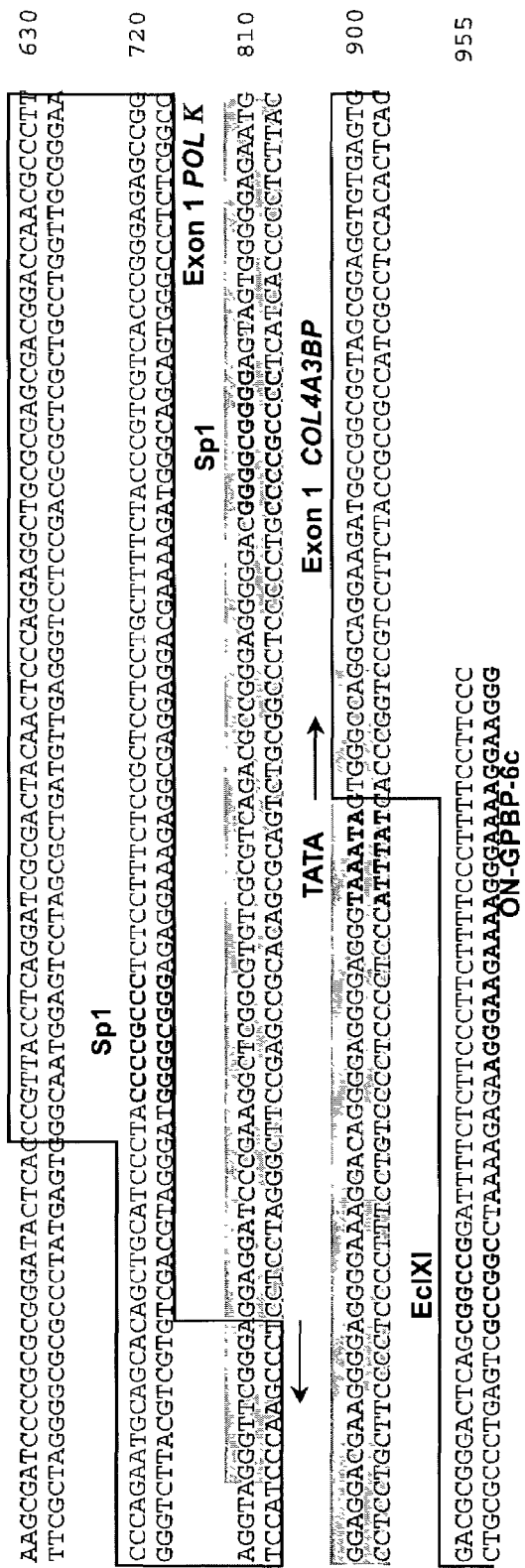

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109–128, ed. E. J. Murray, The Humana Press Inc., Clifton, N.J.), and the Ambion 1998 Catalog (Ambion, Austin, Tex.).

As used herein, the term "COL4A3BP" means the genomic sequence encoding GPBP, as well as controlling sequences for GPBP mRNA expression.

As used herein, the term "POLK" means the genomic sequence encoding pol κ, as well as controlling sequences for pol κ mRNA expression.

As used herein, the term "GPBP" refers to Goodpasture antigen binding protein, and includes both monomers and oligomers thereof, as disclosed in WO 00/50607.

As used herein, the term "GPBPΔ26" refers to the Goodpasture antigen binding protein alternatively spliced product deleted for 26 amino acid residues as disclosed in WO 00/50607, and includes both monomers and oligomers thereof.

As used herein pol κ means the primary protein product of the POLK.

As used herein, pol κ76 means the 76 kDa alternatively spliced isoform product of the POLK.

Goodpasture antigen binding protein (GPBP), is a non-conventional protein kinase that binds to and phosphorylates the human α3(IV)NC1 in vitro. [2,3] Its expression is associated with cells and tissue structures that are target of common autoimmune responses, including the alveolar and glomerular basement membranes [3]. GPBPΔ26 is an alternatively spliced GPBP variant, which is less active than GPBP, but more widely expressed [3]. A balanced expression of the two isoforms appears to be critical for homeostasis, whereas an augmented expression of GPBP relative to GPBPΔ26 has been associated with several autoimmune conditions, including Goodpasture disease and cutaneous lupus [3].

GPBP is expressed at very low levels in cancer cells and highly expressed in apoptotic blebs of differenced keratinocytes at the periphery of normal epidermis [3]. Keratinocytes from patients suffering skin autoimmune processes show an increased sensitivity to UV-induced apoptosis, and a premature apoptosis at the basal keratinocytes has been reported to occur in these patients [38–41]. GPBP is expressed in apoptotic bodies expanding from basal to peripheral strata in epidermis undergoing autoimmune attack [3]. Altered autoantigens, including phosphorylated versions thereof, have been reported to be produced and released from these apoptotic bodies [40]. All these data suggest that GPBP is part of an apoptotic-mediated strategy for desired cell removal that generates aberrant counterparts of critical cell components which operates illegitimately during autoimmune pathogenesis [3].

Pol κ is a member of the UmuC/DinB superfamily of DNA polymerases that can extend aberrant replication forks. Pol κ displays low fidelity, moderate processivity, and extends mispaired DNA by misaligning primer-template to generate −1 frameshift products [4–9]. Pol κ can bypass DNA lesions in both an error-prone [10,11] and an error-free [10] manner. These data indicate that pol κ is a DNA polymerase with a role in the cellular response to DNA-damage, and also in spontaneous mutagenesis, by facilitating base pairing at aberrant replication forks.

In the present study, we have determined that the structural genes encoding polκ and GPBP are present in a head-to-head arrangement in the human genome at chromosome position 5q12–13, and that the genes share a common promoter from which the corresponding transcripts are expressed in a divergent mode. The promoter nucleic acid sequence shows significant sequence identity with a variety of bi-directional promoters encoding genes whose products are not known to be related to GPBP or pol κ. Our results further demonstrate that TNF(α/β) induces transcription directed by these different promoters, suggesting that bi-directional promoters link the expression of proteins that are partners in biological programs which are relevant in autoimmune pathogenesis. As demonstrated in the following examples, pol κ76 shows preferential expression in skin and keratinocytes, which are commonly targeted in systemic lupus erythematosus (SLE) patients. Furthermore, pol κ76 is associated through another protein with GPBP, and augmented expression of GPBP is known to be associated with autoimmune conditions.

Thus, the present invention serves to fill the need for reagents and methods to identify common transcription factors that regulate the expression of genes, such as, COL4A3BP and POLK whose expression is induced and/or enhanced in response to TNF, and which are involved in development and progression of autoimmune responses, in order to design therapeutic interventions to inhibit the activity of such factors, and thereby provide more effective therapies for autoimmune disorders.

In one aspect, the present invention provides an isolated nucleic acid sequence that can promote the expression of an operatively linked coding region in a TNF-inducible manner (Hereinafter, the "TNF inducible promoter"), consisting of an isolated sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29, SEQ ID NO:33, SEQ ID NO:34, SEQ ID NO:35, SEQ ID NO:36. These sequences have been identified as TNF-inducible either on the basis of experimental data, or on the basis of significant sequence homology to the COL4A3BP promoter (SEQ ID NO:6) or the POLK promoter (SEQ ID NO:7), which are demonstrated herein to be TNF-inducible. The isolated nucleic acid sequence may be single-stranded or double-stranded DNA, but preferably is double-stranded DNA.

An used herein, an "isolated nucleic acid sequence" refers to a nucleic acid sequence that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). An "isolated" TNF inducible promoter nucleic acid sequence according to the present invention may, however, be linked to other nucleotide sequences that do not normally flank the recited sequence, such as a heterologous protein-encoding nucleic acid sequence operatively linked to the TNF inducible promoter. It is not necessary for the isolated nucleic acid sequence to be free of other cellular material to be considered "isolated", as a nucleic acid sequence according to the invention may be part of an expression vector that is used to transfect host cells (see below).

As used herein a "protein encoding sequence" means a nucleic acid sequence that contains an open reading frame encoding a protein product. The protein encoding sequence can be a cDNA, or can be genomic DNA containing introns.

A TNF inducible promoter and a protein encoding sequence are "operatively linked" when the promoter is capable of driving expression of the protein encoding sequence into RNA.

In another embodiment, the present invention provides an expression vector comprising one or more TNF-inducible promoter sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29, SEQ ID NO:33, SEQ ID NO:34, SEQ ID NO:35, SEQ ID NO:36. In this embodiment, it is preferred that the TNF-inducible promoter sequence is a double stranded DNA sequence. Thus, a single expression vector may comprise multiple TNF-inducible promoter sequence based on the bi-directional nature of the promoter sequences. For example, an expression vector comprising a TNF-inducible promoter sequence consisting of the nucleic acid sequence of SEQ ID NO:6 also comprises a TNF-inducible promoter sequence consisting of the nucleic acid sequence of SEQ ID NO:7, since SEQ ID NOS:6–7 are complementary sequences. This is similarly true for complementary pairs SEQ ID NOS:8–9; SEQ ID NOS:10–11; SEQ ID NOS:12–13; SEQ ID NOS:14–15; SEQ ID NOS:16–17; SEQ ID NOS:18–19; SEQ ID NOS:20–21; SEQ ID NOS:22–23; SEQ ID NOS:24–25; SEQ ID NOS:26–27; SEQ ID NOS:28–29, SEQ ID NOS:33–34; and SEQ ID NOS:35–36. Alternatively, the expression vector can comprise multiple TNF-inducible promoter sequences that are not complementary.

In a preferred embodiment, the vector comprises a TNF inducible promoter which consists of a nucleic acid sequence selected from the group consisting of SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:26, SEQ ID NO:27, SEQ ID NO:28, and SEQ ID NO:29. In a most preferred embodiment, the vector comprises a TNF inducible promoter which consists of the nucleic acid sequences of SEQ ID NO:6 and SEQ ID NO:7.

As used herein, the term "vector" refers to a nucleic acid molecule capable of transporting another nucleic acid to which it has been linked. One type of vector is a "plasmid", which refers to a circular double stranded DNA into which additional DNA segments may be cloned. Another type of vector is a viral vector, wherein additional DNA segments may be cloned into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors), are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In the present invention, the expression of any genes is directed by the promoter sequences of the invention, by operatively linking the promoter sequences of the invention to the gene to be expressed. In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

In a preferred embodiment, the vector further comprises a polylinker for sub-cloning of a gene of interest in a position to be operatively linked with the promoter sequence. As used herein, "polylinker" means a multipurpose cloning region that has multiple restriction enzyme sites to facilitate cloning of heterologous sequences into the vector. In those embodiments where the expression vector comprises more than one TNF-inducible promoter, it is preferred that a polylinker site be adjacent to each of the promoter sequences for subcloning of genes of interest operatively linked to the promoter sequence.

The vector may also contain additional sequences, such as a polyadenylation signal to effect proper polyadenylation of the transcript. The nature of the polyadenylation signal is not believed to be crucial to the successful practice of the invention, and any such sequence may be employed, including but not limited to the SV40 and bovine growth hormone poly-A sites. Also contemplated as an element of the vector is a termination sequence, which can serve to enhance message levels and to minimize read through from the construct into other sequences. Finally, expression vectors typically have selectable markers, often in the form of antibiotic resistance genes, that permit selection of cells that carry these vectors.

In those embodiment where more than one TNF inducible promoter is used, it is preferred that each TNF inducible promoter sequence be operatively linked to a different protein encoding gene of interest. In a most preferred embodiment, the protein encoding gene of interest is a reporter gene, which produces a product having a readily identifiable and assayable phenotype. Such reporter genes include, but are not limited to luciferase (Promega, Madison, Wis.) chloramphenicol acetyl transferase (Promega), β-galactosidase (Promega), green fluorescent protein (Clontech, Palo Alto, Calif.), human growth hormone (Amersham Life Science, Arlington Heights, Ill.), alkaline phosphatase (Clontech), and β-glucuronidase (Clontech).

In a further embodiment, the present invention provides recombinant host cells transfected with one or more of the expression vectors disclosed herein. As used herein, the term "host cell" is intended to refer to a cell into which a nucleic acid of the invention, such as a recombinant expression vector of the invention, has been introduced. Such cells may be prokaryotic, which can be used, for example, to rapidly produce a large amount of the expression vectors of the invention, or may be eukaryotic. In a preferred embodiment, the host cells are of eukaryotic origin. In a more preferred embodiment, the eukaryotic host cells possess TNF receptors (virtually any cell type from higher level mammals, with the exception of erythrocytes and unstimulated lymphocytes), and are capable of expressing a gene product operatively linked to the TNF-inducible promoter sequence of interest. Examples of such cells include, but are not limited to, human hTERT-RPE1 cells, mouse NIH 3T3, and human 293 cells.

The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The host cells can be transiently or stably transfected with one or more of the expression vectors of the invention. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique,* 2$^{nd}$ Ed. (R. I. Freshney. 1987. Liss, Inc. New York, N.Y.).

The host cells can be transfected with an expression vector that comprises one of the TNF-inducible promoter sequences of the invention and a polylinker site for subcloning of genes of interest to operatively link to the promoter sequence. In another embodiment, the host cells are transfected with an expression vector that comprises two or more of the TNF-inducible promoter sequences of the invention and a polylinker site adjacent to each of the TNF-inducible promoter sequences for subcloning of genes of interest to operatively link to the promoter sequence. For example, an expression vector comprising a TNF-inducible promoter sequence consisting of the nucleic acid sequence of SEQ ID NO:6 also comprises a TNF-inducible promoter sequence consisting of the nucleic acid sequence of SEQ ID NO:7, since SEQ ID NOS:6–7 are complementary sequences. In this case, one polylinker is preferably placed 3' to the 3' end of SEQ ID NO: 6 and a second polylinker is placed 3' to the 3' end of SEQ ID NO: 7. A similar arrangement of polylinkers is preferred for use with the other complementary pairs of TNF-inducible promoter sequences, SEQ ID NOS:8–9; SEQ ID NOS:10–11; SEQ ID NOS:12–13; SEQ ID NOS:14–15; SEQ ID NOS:16–17; SEQ ID NOS:18–19; SEQ ID NOS:20–21; SEQ ID NOS: 22–23; SEQ ID NOS:24–25; SEQ ID NOS:26–27; SEQ ID NOS:28–29, SEQ ID NOS:33–34; and SEQ ID NOS:35–36. The expression vector can comprise concatamers of one of the TNF-inducible promoter sequences of the present invention. Alternatively, the expression vector can comprise multiple TNF-inducible promoter sequences that are not complementary (for example, SEQ ID NO:6–7; as well as SEQ ID NO:8–9 may all be present in a single expression vector). The host cells may also be transfected with two or more expression vectors according to the present invention.

In another embodiment, the host cells are transfected with expression vectors in which a gene of interest has already been cloned into the vector so as to be operatively linked to the TNF-inducible promoter sequence. In those embodiment where more than one promoter sequence is used, it is preferred that each promoter sequence be operatively linked to a different gene of interest. In a most preferred embodiment, the gene of interest is a reporter gene, whose expression is easily assayed. Such reporter genes include, but are not limited to luciferase (Promega, Madison, Wis.) chloramphenicol acetyl transferase (Promega), β-galactosidase (Promega), green fluorescent protein (Clontech, Palo Alto, Calif.), human growth hormone (Amersham Life Science, Arlington Heights, Ill.), alkaline phosphatase (Clontech), and β-glucuronidase (Clontech).

In another aspect, the present invention provides methods for identifying candidate compounds for treating or preventing autoimmune disorders or cancer, comprising providing one or more recombinant eukaryotic cells according to the invention, wherein the recombinant eukaryotic cell is transfected with at least one of the expression vectors of the invention that comprises at least one of the TNF-inducible promoter sequences of the invention operably linked to a detectable reporter gene; contacting the recombinant eukaryotic cell with tumor necrosis factor in the presence or absence of one or more test compounds under conditions that promote expression of the reporter gene, determining the reporter gene expression levels, and identifying those test compounds that modify TNF-induced reporter gene expression, or that modify constitutive expression from the reporter constructs (in the presence or absence of TNF), wherein a modification, such as a reduction or increase in reporter gene expression, identifies a test compound as a candidate for the treatment or prevention of autoimmunity or cancer.

A decrease in promoter activity is measured by a corresponding decrease in production of the reporter gene's product. An increase in promoter activity is measured by a corresponding increase in production of the reporter gene's product. Thus, a decrease in the production of, for example, firefly luciferase, indicates that promoter activity is being suppressed by the compound being tested; an increase in the production of firefly luciferase is indicative of stimulation of the promoter. The effect in production of the assayed product thus reflects the effect of the test compound on the activity of the promoters of the invention in a cell treated with the compound.

The screening method is amendable to high throughput screening, and thus chemical libraries, peptide libraries, and/or collections of natural products can be screened for their ability to modify TNF-induced reporter gene expression.

Any eukaryotic cell that is known to be susceptible to TNF induction of gene expression can be used with these methods, as described above.

While useful data can be obtained assaying a single TNF-inducible promoter-reporter gene construct, it is preferred that the cells be transfected with one or more vectors that in total comprise two or more TNF-inducible promoters of the invention operatively linked to two or more different reporter genes. In this way, the assay can distinguish between factors that might independently operate on one of the genes, and those that are involved in coordinate regulation of the various TNF-inducible genes. Thus, for example, the host cells can be transfected with a first expression vector comprising SEQ ID NO:6 operably linked to a nucleic acid sequence encoding a green fluorescent protein, and further comprising SEQ ID NO:7 operably linked to a nucleic acid sequence encoding a luciferase. In a further example, the host cells may be further transfected with a second expression vector comprising SEQ ID NO:11 operably linked to a nucleic acid sequence encoding a β-galactosidase, and also comprising SEQ ID NO:10 operably linked to a nucleic acid sequence encoding human growth hormone.

In a further aspect, the present invention provides methods for identifying promoters that are regulated by tumor necrosis factor, wherein the method comprises (a) aligning one or more test sequences with a comparison sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29, SEQ ID NO:33, SEQ ID NO:34, SEQ ID NO:35, SEQ ID NO:36, using a gap opening penalty of 50 and a gap extension penalty of 3 to define one or more test alignments; (b) shuffling each individual test sequences at least 100 times, while maintaining its length and composition, to produce a series of randomized sequences; (c) aligning individual randomized sequences with the comparison sequence using a gap opening penalty of 50 and a gap extension penalty of 3, to produce a series of randomized alignments; (d) determining an average alignment quality of the randomized alignments, wherein the average alignment quality of the randomized alignments represents an alignment expected by chance; (e) comparing the one or more test alignments with the average alignment quality of the corresponding randomized alignments; and (f) identifying those test alignments with a probability value of less than 0.05 that the alignment is obtained by chance, wherein such a probability value identifies a test sequence as being a candidate tumor necrosis factor inducible promoter.

This method can serve to identify known test sequences with the requisite homology to known TNF-inducible promoters, to identify them as potentially being TNF-inducible promoters. The ability of such known test sequences to serve as TNF inducible promoters can be assayed, as disclosed herein.

The present invention may be better understood with reference to the accompanying examples that are intended for purposes of illustration only and should not be construed to limit the scope of the invention, as defined by the claims appended hereto.

EXAMPLES

Materials and Methods

Synthetic oligonucleotides. The following oligonucleotides and other used for DNA sequencing were synthesized by Genosys, Life Technology Inc., Roche or Pharmacia:

| | | |
|---|---|---|
| ON-GPBP-6c, | CTCGCTCGCCCAGGGAAGGAAAAGGGAAAAGAAGGGA-3'; | (SEQ ID NO:37) |
| ON-GPBP-14c, | 5'-CTGCCTGGCCCACTATTTACC-3'; | (SEQ ID NO:38) |
| ON-GPBP-18m, | 5'-GGCATGGTTAACGTGGTTCTC-3'; | (SEQ ID NO:39) |
| ON-XbaG/Bpro1m, | 5'-GACTCTAGAGGGTTCGGGAGGAGGATCCCG-3'; | (SEQ ID NO:40) |
| ON-XbaG/Bpro1c, | 5'-GACTCTAGACTGGCCCACTATTTACCCTCC-3'; | (SEQ ID NO:41) |
| ON-SP1Del, | 5'-CGCCGGGAGGGGACGTAGTGGGGGAGAAT-3'; | (SEQ ID NO:42) |
| ON-TATADel, | 5'-CAGGGGAGGGGAGGGGTGGGCCAGTCTAGA-3'; | (SEQ ID NO:43) |
| ON-DIN2c, | 5'-GGATTATTGCACTTGCCTTCAC-3'; | (SEQ ID NO:44) |
| ON-DIN5'm, | 5'-AAAGGATCCATGGATAGCACAAAGGAG-3'; | (SEQ ID NO:45) |
| ON-DIN-THc, | 5'-AAAAAAGTCGACTTACTTAAAAAATATATCAAGGGT-3'; | (SEQ ID NO:46) |
| ON-DINB1-R2, | 5'-TGGTATTGCTCAAATTTCGGC-3'; | (SEQ ID NO:47) |
| ON-GPBP-39c, | 5'-TGAGAGAGCTTTCCGCTG-3'; | (SEQ ID NO:48) |
| ON-LMPTAP1m, | 5'-ATGTCTAGATGTGTAGGGCAGATCTGCCC-3'; | (SEQ ID NO:49) |

-continued

| | | |
|---|---|---|
| ON-LMPTAP1c, | 5'-ATGTCTAGACTGGTGCCCAATTTTCTCCA-3'; | (SEQ ID NO:50) |
| ON-HSP1m, | 5'-ATGTCTAGATAAGCCGGCCGGAGAGGGCT-3'; | (SEQ ID NO:51) |
| ON-HSP1c, | 5'-ATGTCTAGACGCGGCACCGCGTGTGCAGG-3'; | (SEQ ID NO:52) |
| ON-SA3A4m, | 5'-GACTCTAGAGGGTTAAGGAGGTGATGCTCCC-3'; | (SEQ ID NO:53) |
| ON-SA3A4c, | 5'-GACTCTAGATGGCCACTCCCTCCACCCTGCGC-3'; | (SEQ ID NO:54) |
| ON-JNGA3A4m, | 5'-GACTCTAGACACCCAGGCTTTTTGGTTGTGGC-3'; | (SEQ ID NO:55) |
| ON-INGA3A4c, | 5'-GACTCTAGAAAGCGGGGCCTCCCGCAGACGC-3'; | (SEQ ID NO:56) |
| ON-S2A3A4m, | 5'-ATGTCTAGATAGGCACTGGACAAGCCCCC-3'; | (SEQ ID NO:57) |
| ON-S2A3A4c, | 5'-ATGTCTAGAGGGCTAGTGGCGAGGCTGAG-3'; | (SEQ ID NO:58) |
| ON-IDH-F1, | 5'-CACAGAGGGCGAGTACAGCA-3'; | (SEQ ID NO:59) |
| ON-IDH-R1, | 5'-TGATCTTCAGGCTCTCCACCA-3'; | (SEQ ID NO:60) |
| ON-TRAPD-F1, | 5'-GGGTCCAGAACATGGCTCTC-3'; | (SEQ ID NO:61) |
| ON-TRAPD-R1, | 5'-ACATCCTGGCCTCGAGTGAC-3'; | (SEQ ID NO:62) |
| ON-LMP2-F2, | 5'-GCAGCATATAAGCCAGGCATG-3'; | (SEQ ID NO:63) |
| ON-LMP2-R2, | 5'-TGGCCAGAGCAATAGCGTCT-3'; | (SEQ ID NO:64) |
| ON-TAP1-F2, | 5'-GCCGCCTCACTGACTGGAT-3'; | (SEQ ID NO:65) |
| ON-TAP1-R2, | 5'-TCGAGTGAAGGTATCGGCTGA-3'; | (SEQ ID NO:66) |
| ON-DHFR-F1, | 5'-CCTGTGGAGGAGGAGGTGG-3'; | (SEQ ID NO:67) |
| ON-DHFR-R1, | 5'-CCGATTCTTCCAGTCTACGGG-3'; | (SEQ ID NO:68) |
| ON-MSH3-F1, | 5'-TGGGTAAAGGTTGGAAGCACA-3'; | (SEQ ID NO:69) |
| ON-MSH3-R1, | 5'-AAAAGGAGAGTGAAAGCGGCT-3'; | (SEQ ID NO:70) |
| ON-HO3-F2, | 5'-GAGCTGTTGTCCCTCCGCT-3'; | (SEQ ID NO:71) |
| ON-HO3-R2, | 5'-GGCCAGATAACGAGCAAAGG-3'; | (SEQ ID NO:72) |
| ON-HARS-F2, | 5'-AGGTGGCGAAACTCCTGAAAC-3'; | (SEQ ID NO:73) |
| ON-HARS-R2, | 5'-TGCTTTCATCAGGACCCAGC-3'; | (SEQ ID NO:74) |
| ON-Hsp10-F1, | 5'-GGAGGGAGTAATGGCAGGACA-3'; | (SEQ ID NO:75) |
| ON-Hsp10-R1, | 5'-AGCAGCACTCCTTTCAACCAA-3'; | (SEQ ID NO:76) |
| ON-Hsp60-F1, | 5'-GCCTTTGGTCATAATCGCTGA-3'; | (SEQ ID NO:77) |
| ON-Hsp60-R1, | 5'-TGCCACAACCTGAAGACCAAC-3'; | (SEQ ID NO:78) |
| ON-COL4A1-F1, | 5'-GCTCTACGTGCAAGGCAATGA-3'; | (SEQ ID NO:79) |
| ON-COL4A1-R1, | 5'-ATTGTGCTGAACTTGCGCAG-3'; | (SEQ ID NO:80) |
| ON-COL4A2-F1, | 5'-GAAAAGGGTGACGTAGGGCA-3' | (SEQ ID NO:81) |
| ON-COL4A2-R1, | 5'-GGTGTCTGATGGAATCCCGTT-3'; | (SEQ ID NO:82) |
| ON-GP-F1, | 5'-GGAGACAGTGGATCACCTGCA-3'; | (SEQ ID NO:83) |
| ON-GP-R1, | 5'-TGCTGTGGTTTGACTGTGTCG-3'; | (SEQ ID NO:84) |
| ON-COL4A4-F1, | 5'-CTTGCCTTCCCGTATTTAGCA-3'; | (SEQ ID NO:85) |
| ON-COL4A4-R1, | 5'-GGATCTGTCGTTTCTCTGGGC-3'; | (SEQ ID NO:86) |
| ON-COL4A5-F1, | 5'-CATCGAATGTCATGGGAGGG-3'; | (SEQ ID NO:87) |
| ON-COL4AS-R1, | 5'-AGTTGCCAGCCAAAAGCTGTA-3'; | (SEQ ID NO:88) |
| ON-COL4A6-F1, | 5'-TTTGGGCTAGACTACCGGACA-3'; | (SEQ ID NO:89) |

| | | -continued | |
|---|---|---|---|
| ON-COL4A6-R1, | 5'-TCTCTATGGACCCGAGGGCT-3'; | | (SEQ ID NO:90) |
| ON-GPBP-F1, | 5'-CTGAATCCAGCTTGCGTCG-3'; | | (SEQ ID NO:91) |
| ON-GPBP-R1, | 5'-GCAGAGTAGCCACTTGCTCC-3'; | | (SEQ ID NO:92) |
| ON-DinB1-F3, | 5'-GCCCCCCAACTTTGACAAAT-3'; | | (SEQ ID NO:93) |
| ON-DinB1-R3, | 5'-GCTTCATCAAGACTCATGCC-3'; | | (SEQ ID NO:94) |
| ON-hGAPDH-F1, | 5'-GAAGGTGAAGGTCGGAGTC-3'; | | (SEQ ID NO:95) |
| ON-hGAPDH-R1, | 5'-GAAGATGGTGATGGGATTTC-3'; | | (SEQ ID NO:96) |
| ON-GPBP-26-1F, | 5'-GCTGTTGAAGCTGCTCTTGACA-3'; | | (SEQ ID NO:97) |
| ON-mGPBP-26-1R, | 5'-CCATTTCTTCAACCTTTTGTACAA-3'; | | (SEQ ID NO:98) |
| ON-GPBPe26-1R, | 5'-CTTGGGAGCTGAATCTGTGAA-3'; | | (SEQ ID NO:99) |
| ON-huDINB-76-F1, | 5'-CCAGTGCAGGTGTTCGGATA-3'; | | (SEQ ID NO:100) |
| ON-huDTNB-76-R1, | 5'-TTTCCAGCCTGTAAAAAGCCA-3'. | | (SEQ ID NO:101) |
| ON-hGPBP-26-1R, | 5'-CCATCTCTTCAACCTTTTGGACA-3' | | (SEQ ID NO:102) |

Isolation of the 5' genomic region of COL4A3BP. The 5'-end region of COL4A3BP was isolated by PCR using ON-GPBP-6c, Adapter primer 2 (AP2)(Clontech) and DNA from human genomic libraries (PromoterFinder DNA Walking Kit (Clontech)). We obtained a single DNA fragment in four of the five of the libraries screened (1.6, 1.3, 0.8, and 0.4 kb, respectively). By sequencing the 0.4-kb DNA fragment we characterized the COL4A3BP region immediately upstream of the cDNA clone (n4') (SEQ ID 1) previously reported (Disclosed in WO 00/50607; GenBank accession no AF136450) [2]. Based on the sequence of the 0.4 kb fragment, we designed and synthesized ON-GPBP-14c, and used it in combination with AP2 to perform PCR on the 1.6 kb genomic library fragment. From this PCR, we obtained a PCR DNA fragment of ~1.5 kb containing the 5' genomic region of COL4A3BP without any exon sequences present in n4'. This DNA fragment was then used to screen a HeLa-derived cDNA library, from which we isolated HeLa 4.1, a clone containing 1.3 kb of cDNA (SEQ ID NO:2 (GenBank accession no AF315601). Finally, we used ON-GPBP-18m (an oligonucleotide derived from HeLa 4.1) and ON-GPBP-6c (an oligonucleotide derived from n4') to conduct PCR on human genomic DNA, from which we generated a 955-bp PCR product (SEQ ID NO:3)(GenBank accession no AF315603) that contained HeLa 4.1 sequence, the 5' region of the first exon of COL4A3BP, and the intervening DNA region (FIG. 1).

Plasmid construction. A 772-bp DNA fragment was generated by digesting the 955-bp PCR product (SEQ. ID NO:3) with XbaI and EclXI, the ends were filled-in, and the orientation expressing COL4A3BP (SEQ ID NO:4) or POLK (SEQ ID NO:5) cloned into the HincII site of pΦGH (Nichols Institute) immediately upstream of human growth hormone reporter gene to generate LpromGPBP and Lprom-Polκ. Alternatively, ON-XbaG/Bpro1m and ON-XbaG/Bpro1c were used to obtain a 140-bp PCR product which contained the intergene region, the major transcription start sites for each gene and a few nucleotides of the corresponding exon 1 from either COL4A3BP or POLK (shaded sequence in FIG. 1). Upon digestion with XbaI, each of the two orientations (SEQ ID NO: 6; SEQ ID NO: 7) was cloned in the corresponding restriction site of the polylinker region of pΦGH to generate SpromGPBP and SpromPolK, respectively. Subsequently, SpromGPBP was used to obtain constructs in which Sp1, TATA, or both sites were selectively deleted. This was accomplished using ON-SP1Del, ON-TATADel or both and a site-directed mutagenesis approach. To obtain the corresponding promoter mutants for POLK, we cloned the reverse orientation of the SpromGPBP mutants by XbaI digestion and re-ligation.

To generate pΦGH-based constructs containing 140-bp homologous regions of COL4A3/COL4A4, LMP2/TAP1 and HSP10/HSP60, human DNA was prepared from blood cells using a DNA purification kit (Epicenter), and the regions of interest amplified by PCR using the following pair of synthetic oligonucleotides ON-S2A3A4m/ON-S2A3A4c, ON-SA3A4m/ON-SA3A4c, ON-INGA3A4m/ON-INGA3A4c to obtain the DNA regions corresponding to 182–318 (SEQ ID NO: 8; SEQ ID NO:9), 849–990 (SEQ ID NO: 10; SEQ ID NO:11), 675–1045 nucleotides (SEQ ID NO: 12; SEQ ID NO:13) of AF218541; ON-LMPTAP1m/ON-LMPTAP1c to obtain the DNA fragment containing the 24579–24718 nucleotides (SEQ ID NO: 14; SEQ ID NO:15) of X66401; and ON-HSP1m/ONHSP1c to obtain the 3451–3590 nucleotides (SEQ ID NO: 26; SEQ ID NO:27) of AJ250915. The DNA fragments were individually digested with XbaI and cloned in the corresponding site of the polylinker region of pΦGH in each of the two orientations.

To generate pGBT9 and pGAD424 plasmids for pol κ and pol κ76 the corresponding cDNA fragments obtained by RT-PCR (see below) were digested with BamHI and SalI and cloned in the corresponding sites of a FLAG modified version of the corresponding expression vectors (Clontech) engineered essentially as previously described [2] but containing a BamHI site immediately downstream of the FLAG peptide sequence.

All the plasmid-based constructs were characterized by nucleotide sequencing.

Plasmid expressing human glyceraldehyde 3-phosphate dehydrogenase (GAPDH) was provided by Erwin Knecht.

Ribonuclease protection assays. By digesting LpromG-PBP with ApaI and EclXI we obtained a DNA fragment of 503-bp containing the two 5' end regions of POLK and COL4A3BP genes and the intergene region. The DNA fragment was blunt-end with T4 DNA polymerase and cloned into the HincII site of Bluescribe M13+ (Stratagene).

Ribonucleotide probes from T3 and T7 promoters representing the antisense of the GPBP or pol κ mRNAS respectively were obtained using MAXIscript ™ T7/T3 in vitro transcription kit (Ambion). Individual ribonucleotide probes were subject to ribonuclease protection assays using RPAIII™ (Ambion) and total RNA from human cultured hTERT-RPE1 (Clontech) or 293 cells (ATCC # CRL-1573). The digestion mixtures were analyzed by gel electrophoresis (8M urea 8% acrylamide gel) and autoradiography.

RNA purification. Total RNA was prepared from human tissues or cultured cells using TRI-REAGENT (Sigma) and following the manufacturer's recommendations.

Reverse transcription (RT) and polymerase chain reactions studies(PCR).

To obtain a continuous cDNA fragment containing HeLa 4.1 and pol κ coding sequences (GenBank accession no AF318313 (SEQ ID NO: 32) we carried out a PCR on human striated muscle cDNA library (MATCHMAKER™ from Clontech) with ON-GPBP-39c and ON-DINB1-R2 primers using the Expand™ Long Template PCR System (Roche). To obtain the cDNA for pol κ or pol κ76, 5 µg of total RNA extracted from human foreskin was reverse-transcribed with ON-DIN2c using the Ready-To-Go system (Pharmacia). An aliquot (0.5 µl) of the resulting cDNA-RNA hybrid was similarly subjected to PCR using ON-DIN5'm and ON-DIN-THc.

Real Time PCR studies were performed using a SDS 7700 Applied Biosystems apparatus and aliquots of either human cDNA libraries for striated muscle, HeLa cells, keratinocytes, pancreas, brain and kidney (MATCHMAKER from Clontech) or random hexamer reverse-transcriptase reactions performed as above using total RNA extracted from human hTERT-RPE1 cells, foreskin, lung, spleen, adrenal gland and kidney or from mouse kidney.

The mRNA determinations in hTERT-RPE were done on 5 µl of a 1:10 (for the different genes of interest) or 1:1000 (for GAPDH) dilution of a single reverse transcriptase reaction using the Relative Quantitation Method analysis (ΔΔCt) following manufacturer's recommendations. GAPDH was used as endogenous control to normalize quantification. The pair of oligonucleotides were, ON-IDH-F1 and ON-IDH-R1 for IDHG; ON-TRAPD-F1 and ON-TRAPD-R1 for TRAPD; ON-LMP2-F2 and ON-LMP2-R2 for LMP2; ON-TAP1-F2 and ON-TAP1-R2 for TAP1; ON-DHFR-F1 and ON-DHFR-R1 for DHFR; ON-MSH3-F1 and ON-MSH3-R1 for MRP1; ON-HO3-F2 and ON-HO3-R2 for HO3; ON-HARS-F2 and ON-HARS-R2 for HRS; ON-Hsp10-F1 and ON-Hsp10-R1 for HSP10; ON-Hsp60-F1 and ON-Hsp60-R1 for HSP60; ON-COL4A1-F1 and ON-COL4A1-R1 for COL4A1; ON-COL4A2-F1 and ON-COL4A2-R1 for COL4A2; ON-GP-F1 and ON-GP-R1 for COL4A3; ON-COL4A4-F1 and ON-COL4A4-R1 for COL4A4; ON-COL4A5-F1 and ON-COL4A5-R1 for COL4A5; ON-COL4A6-F1 and ON-COL4A6-R1 for COL4A6; ON-GPBP-F1 and ON-GPBP-R1 for COL4A3BP; ON-DinB1-F3 and ON-DinB1-R3 for POLK; ON-hGAPDH-F1 and ON-hGAPDH-R1 for GAPDH.

To determine mRNA levels for human pol κ or pol κ76 PCR reactions were performed using ON-DINB1-F3 and ON-DINB1-R3 or ON-huDINB-76-F1 and ON-huDINB-76-R1 respectively, and either 6 and 60 ng of the different cDNA libraries, or 5 µl of a 1:10 dilution of the individual reverse transcriptase reactions. Standard curves for each PCR were done using the same oligonucleotides and different amounts of individual plasmids containing the corresponding cDNAs.

To determine GPBP and GPBPΔ26 mRNA levels in mouse kidney PCR reactions were done using ON-GPBP-26-1F and ON-GPBPe26-1R or ON-mGPBP-26-1R, respectively and 5 µl of a 1:10 and 1:100 dilution of the individual reverse transcriptase reactions.

To determine GPBP and GPBPΔ26 mRNA levels in human skin samples PCR reactions were done using ON-GPBP-26-1F and ON-GPBPe26-1R or ON-hGPBP-26-1R, respectively and 5 µl of a 1:10 dilution of the individual reverse transcriptase reactions.

Northern analysis. Pre-made Northern blots (Clontech) were probed with $^{32}$P-labeled cDNAs representing GPBP (n4') or pol κ (see above) according to manufacturer's instructions.

Cell culture and transient gene expression assays. Cells were grown in DMEM (NIH 3T3 and 293) or DMEM F-12 HAM (hTERT-RPE1) with 100 units/ml of penicillin and 100 µg/ml streptomycin, and supplemented with 10% calf serum (NIH 3T3 cells) or fetal calf serum (hTERT-RPE1 and 293). For transient gene expression assays, NIH 3T3 cells ($1.4 \times 10^5$) were seeded in 9.5 cm² plates, cultured for 14–16 hours, and then transfected for 16–18 hours with 2.5 µg of each individual pΦGH-derived plasmid and 2.5 µg of β-galactosidase expression vector (Promega) using the calcium phosphate precipitation method of the Profection Mammalian Transfection System (Promega). After transfection, the cells were rinsed with phosphate-buffered saline, fresh medium was added, and the levels of human growth hormone in the media were determined after 48 hours using a solid phase radioimmunoassay system (Nichols Institute). β-galactosidase activity determination was performed following manufacturer's recommendations. For some purposes, after transfection the cells were cultured in low serum (0.5%) media for 24 hours, media was discarded, and fresh low serum media containing TNFα (10 ng/ml) or TNFβ (50 ng/ml) was added, and levels of human growth hormone similarly determined.

For other purposes hTERT-RPE1 cells were grown up to 60–70% confluence, media removed and fresh serum-free media added and culture continued. After 24 hours the media was removed, fresh serum-free media containing TNFβ (50 ng/ml) added, and, after one hour, the media was discarded and cells were used for RNA preparation.

Isolation of genomic DNA encoding GPBP. We have used human GPBP cDNA fragments obtained from specific PCR amplification of n4' to screen a human genomic library, λfix-w138 (Stratagene). Two independent and overlapping genomic clones λfixGPBP1 and λfixGPBP3, of ~14 kb and ~13 kb respectively, were characterized by restriction mapping and partial nucleotide sequencing. The nucleotide sequence of ~12 Kb of the λfixGPBP1 has been recently reported (GenBank accession no AF232935) [3].

Chromosome localization of COL4A3BP, the structural gene for GPBP. To map COL4A3BP, a fluorescence in situ hybridization (FISH) analysis was performed essentially as described in Ref. 13 on metaphase chromosomes obtained from control peripheral blood using λfixGPBP1 and λfixGPBP3, labeled by standard nick-translation with digoxigenin-11-dUTP and biotin-16-dUTP respectively. The hybridized material was detected using either sheep anti-digoxigenin-FITC (fluoresceine isothiocyanate (Roche) or avidine-rhodamine (Vector Laboratories).

Computer analysis. Alignments were generated with the program GAP of the GCG-package (Genetics Computer Group). GAP uses the algorithm of Needleman and Wunsch [14] As originally introduced the algorithm sought to maximize a similarity, or quality (Q), between two sequences.

From any pair of bases, an alignment can be extended in three ways: adding a base in each sequence, with a specified addition to the distance if the bases do not match, or adding a base in one sequence but a gap in the other, or vice versa. Introduction of a gap also contributes a specific amount to the distance. Formally, the best alignment will be the one that keeps up the relationship $Q=\max(x-\Sigma z_k w_k)$, where x is the number of matched pairs, $z_k$ the number of gaps with length k, and $w_k$ the penalty for a gap of length k. Many systems of gap penalty have been used; the liner system being the most commonly used because it saves computer time. In this system $w_k=\alpha+\beta k$, where $\alpha$ (the gap-opening penalty) and $\beta$ (the gap-extension penalty) are non-negative parameters. Which alignment is preferable depends upon the penalty weights used. For example, a small $\alpha$ along with a big $\beta$ will favor an alignment with many short gaps, whereas a large $\alpha$ with a small $\beta$ will favor an alignment with few long gaps. The gap parameters employed in the analysis were $\alpha=50$ and $\alpha=3$. The statistical distribution of Q is not well characterized. Therefore, to assess the statistical significance of an alignment it is necessary to use a bootstrapping technique. In brief, the sequence being aligned is shuffled 100 times, maintaining its length and composition, and then realigned to the target POLK/COL4A3BP sequence. The average alignment quality, E(Q), plus or minus the standard deviation, of all randomized alignments can be used to evaluate the significance of the alignment. If the observed Q is significantly larger than that expected by chance, E(Q), then a P<0.05 would be obtained. FIGS. 3 and 4 show the observed Q values as well as E(Q) (±standard error).

Animal studies. The implication of TNF and GPBP in the development of murine systemic lupus erythematosus (SLE) was analyzed in F1 hybrids between NZW females and C57BL/6 (B6) males that over-express a human Bcl-2 transgene in the B cell compartment under the regulation of the SV40 promotor and IgM enhancer. These Bcl-2-transgenic F1 mice develop an aggressive SLE characterized by the production of a large spectrum of pathogenic autoantibodies resulting in the development of an immunocomplex-mediated gomerulonephritis and early death (50% of mortality is observed at 9–10 months of age) [15]. In contrast, non-transgenic (NZW×B6)F1 mice are immunologically normal and are used as controls. The development of the disease in the Bcl-2-transgenic F1 mice is believed to be a consequence of an over-expression of human Bcl-2 in B cells that prolongs the survival of potentially autoreactive B cells generated either in the bone marrow or in the germinal centers of secondary lymphoid organs in the course of T cell-dependent antibody responses, and also because of the genetic predisposition to SLE provided by the NZW genetic background. In this respect, several genetic loci associated with the production of autoantibodies and/or glomerulonephritis (GN) have been mapped in the NZW mouse strain. However, the nature of these genetic defects associated with the different autoimmune traits remains at the present largely unknown. The production of autoantibodies in Bcl-2-transgenic F1 mice is first observed at 2 months, and glomerular lesions are already evident at 3–5 months of age. As observed in other murine models of spontaneous SLE, both autoantibody production and GN are inhibited after the treatment from birth of (NZW×B6)F1-Bcl-2 mice with an anti-CD4 monoclonal antibody, indicating that the disease is a CD4-dependent phenomenon.

For some purposes, (NZW×B6)F1 mice were treated from birth with anti-CD4 antibodies as previously reported [16], and the presence of the transgene (Tg) in each animal determined as described [17]. The anti-CD4 treatment was continued for the F1Tg(+) up to three month and then half of mice were maintained without additional treatment whereas the other half were enrolled in a program with anti-TNF antibodies (V1q) essentially as described [18] but using 30 µl of V1q ascites three times per week. After two and a half months both anti-TNF treated and non-treated animals were sacrificed and one of the kidneys used for histology and immohistochemistry, and the other for mRNA studies. For similar purposes we also obtained the kidneys of animals representing the parental strands, female NZW and male C57BL/6-Bcl-2 and three month old (NZW×B6)F1Tg(−) and (NZW×B6)F1Tg(+) maintained without anti-CD4 treatment.

For other purposes, B6 mice were intraperitoneally injected with 50 µg of lipopolysaccharides (LPS) obtained from Salmonella minnesota (Sigma), which induces a dramatic increase in the serum levels of TNFα, resulting in the development of endotoxic shock [19]. Either three or six hours after LPS injection, mice were sacrificed and their kidneys immediately extracted, frozen in dry ice, and used for RNA isolation. Non injected C57BL/6 mice were similarly sacrificed and their kidneys obtained for use as controls.

Immunochemical techniques. Immunihistochemical studies were performed on formalin-fixed, paraffin-embedded mouse kidneys essentially as described [2,3], using GPBP polyclonal antibodies (2) at 1:50 dilutions. Prior to antibody detection, antigen retrieval was achieved heating with autoclave (1.5 atmospheres for 3 minutes in 10 mM sodium citrate buffer pH 6.0).

For some purposes the presence of anti-ssDNA autoantibodies was determined in the sera of the mice using an ELISA approach [17].

Results

Structural characterization of the 5' region of COL4A3BP. To characterize the promoter region of COL4A3BP we first attempted to determine the transcriptional start site by primer extension analysis. However, and likely due to the high G+C content at the 5'-end untranslatable region (UTR) [2], we obtained premature stops during reverse transcription at positions 56, 61 or 68 of the cDNA in n4' (GenBank accession no AF136450) (not shown). A similar negative results were obtained when a 5'-RACE approach was used to identify mRNA species extending beyond the 5' end of n4' (not shown). To overcome this inconvenient, we isolated and characterized by partial nucleotide sequencing ~1.5 kb of genomic DNA located upstream of the 5'-UTR of n4', and screened a cDNA human library to identify clones containing additional 5'-UTR of GPBP not present in n4'. We isolated and sequenced 1.3-kb HeLa 4.1 ((SEQ ID NO:2) GenBank accession no AF315601), which did not overlap with n4' although contained sequence present in the 1.5-kb DNA. Because HeLa 4.1 did not contain open readings of consideration in the six frames (not shown), its cDNA likely represents either 5'-UTR of GPBP not present in n4' or sequence corresponding to an UTR of other gene mapping 5' of COL4A3BP. The first possibility was abandoned since we failed to amplify by RT-PCR a continuous cDNA fragment containing both HeLa 4.1 and n4' sequences (not shown). As expected, however, we succeeded obtaining a DNA fragment of 955-bp ((SEQ ID NO:3) GenBank accession no AF315603) when subjecting human DNA to PCR using ON-GPBP-18m, a forward primer derived from HeLa 4.1, and ON-GPBP-6c, a reverse primer derived from n4' (FIG. 1), thus supporting the second possibility. To assign a gene for HeLa 4.1, we first search at the data banks and we found not a gene to contain HeLa 4.1 cDNA sequence. However, when we included in the search the 418-bp DNA connecting HeLa 4.1 and n4' sequences at the human genome which is comprised in SEQ ID NO:3 (FIG. 1), we found that it contained inverted 159-bp of 5'-UTR present in the mRNA encoding for pol κ (GenBank accession no AF163570), a novel member of the growing family of DNA polymerases that display ability to bypass mismatches during DNA replication [5]. This suggested that HeLa 4.1 contained part of the 5'UTR of pol κ not present in the mRNA molecular species previously characterized. Therefore HeLa 4.1 represented either an alternatively spliced variant or an alternative transcriptional start site. Using a RT-PCR approach we have not been able to identify a mRNA species containing both HeLa 4.1 and the 159-bp exon sequence (not shown), suggesting that HeLa 4.1 likely represents an alternative transcription start site. Nevertheless to assess that HeLa 4.1 indeed contains 5'-UTR of POLK we have performed specific PCR on human muscle cDNA and identified a molecular species containing both HeLa 4.1 and pol κ coding sequence (GenBank accession no AF318313). The resulting cDNA fragment, however, did not contain the full HeLa 4.1 sequence and contained 142-bp of UTR not present neither in HeLa 4.1 neither in the original pol κ sequence reported [5], thus confirming the existence of at least three mRNA species for pol κ with different 5'-UTR and suggesting that the 140-bp flanked by the most 5'-UTR of the two genes (FIG. 1) (SEQ ID NO: 6 and SEQ ID NO:7) (SEQ ID NO:33 and SEQ ID NO:34 show the corresponding mouse 140 bp sequence) contains a bidirectional promoter. Finally, we have used RNA-protection assays to map the transcriptional start sites for each of the genes. When radiolabeled RNA probes representing the antisense strand of POLK or COL4A3BP between the ApaI and EclXI sites (FIG. 1) were separately hybridized with human RNA, one major fragment of 169 and 63 nucleotides long was respectively protected from RNase digestion. Minor fragments, one of 151 nucleotides for POLK and several others for COL4A3BP were also protected (not shown). However, from the comparison of DNA and cDNA sequences the fragments expected to be protected by the exon 1 were 159 and 55 nucleotides long respectively. Therefore, these results would suggest the existence of two major transcriptional start sites one for POLK and another for COL4A3BP which extend the 5' end of the corresponding mRNAs ten and eight nucleotides into the intergene region with respect to the cDNA sequence previously reported (FIG. 1). The significance of the additional protected fragments identified is uncertain as may represent alternative transcriptional start sites, a common feature in bidirectional promoters [20–22] or alternatively, and because of the high content in G+C, lack of protection of the more abundant fragments due to defective pairing caused by secondary structures. Nevertheless these findings suggest that the genomic region flanked by the two major transcriptional start sites contains the structural requirements for bidirectional transcription. In this respect the size, the presence of alternative transcriptional start sites, a Sp1 site, a single TATA box and the high content in G+C are structural features shared by other bidirectional promoters [20–22].

Chromosomal mapping of the human COL4A3BP gene. By FISH analysis others have shown a single locus for POLK at band 5q13 [5]. In similar studies and consistent with the proposed head-to-head arrangement of COL4A3BP and POLK, two independent overlapping DNA fragments of COL4A3BP hybridized with a single locus mapping at 5q12–13. According to the last publicly available data on the human genome sequence, both COL4A3BP and POLK map to 5q13.3. In the last freeze of the sequence (http://genome.ucsc.edu/goldenPath/apr2001Tracks.html) there still remains a gap between both genes that is bridged with the sequence reported here (SEQ ID NO:3) GenBank accession no AF315603) (FIG. 1). Finally whereas this manuscript was being completed a GenBank accession number AB036934 was released which contained the sequence reported here thus confirming the head-to-head arrangement we have proposed.

Characterization of the bidirectional transcription unit for POLK and COL4A3BP. To investigate the presence of a bidirectional promoter in the intergene region we cloned in pΦGH each of the two orientations of a 772-bp DNA fragment (SEQ ID NO: 4 and SEQ ID NO:5) encompassing the region of interest (LpromPolκ and LpromGPBP) and we assessed their ability to drive heterologous gene expression in NIH 3T3 cells (FIG. 2A). The 772-bp fragment efficiently promoted heterologous gene expression in each orientation, 25-fold over control in the POLK direction for 21-fold in the COL4A3BP orientation. When we assessed the transcriptional activity of the 140-bp DNA region (shaded sequence in FIG. 1) containing the identified 5' transcriptional start sites for each gene (SEQ ID NO:6 and SEQ ID NO:7) (SpromPolκ and SpromGPBP), we observed a reduction in the activity that was more evident for COL4A3BP orientation than for POLK, a 45% reduction versus 18%, indicating that although the 140-bp contains the core of the bidirectional transcriptional unit and the structural requirements for divergent transcription, in the flanking structural gene regions there are regulatory elements that modulate both gross activity and relative transcription rates in each orientation. In this regard in the exon 1 of POLK there is a Sp1 site (FIG. 1) that could account at least in part for the higher transcriptional activity of the larger promoter constructs.

The contribution that the individual DNA elements identified in the 140-bp DNA region had on the transcriptional activity was assessed using promoter constructs in which the Sp1 site or/and the TATA box were deleted (FIG. 2B). The removal of each of the two DNA elements had consequences in the transcriptional activity of the promoter although these were significantly different for each orientation. Thus Sp1 site deletion greatly impaired transcription in the two orientations although this was more evident for POLK transcription. In contrast TATA box deletion greatly reduced transcription in COL4A3BP direction but had little effect over POLK transcription. Finally, double deletions were additive in the negative effects over transcription in either orientation reaching values slightly above those obtained with empty vector (7–12%). These results suggest that the TATA box is mainly used for COL4A3BP expression whereas Sp1 is the major element through which operates the bidirectional expression.

The expression of the bidirectional unit in human tissues The transcriptional activity of the bidirectional promoter in human tissues was investigated by Northern blot analysis. With the exception of brain and pancreas that showed a relatively reduced expression of pol κ, comparison of mRNA levels among tissues revealed that the two genes are expressed in a coordinated manner in normal human tissues, whereas coordination appears to be disrupted during cell transformation as comparison of mRNA levels in human cancer cell lines showed that cells with a relative higher expression of GPBP expressed relatively less pol κ and vice versa (not shown). In either case this suggests that pol κ and GPBP are likely partners in specific biological functions and that the head-to-head arrangement of the corresponding genes is the strategy to co-regulate their expression.

Sequence homology between POLK/COL4A3BP and COL4A3/COL4A4 promoters. Several housekeeping genes, including those encoding a chains of collagen type IV, are transcribed from short, bi-directional, G+C rich promoters containing Sp1 sites [22]. Six related genes organized in three transcriptional units encode the human α(IV)chains (α1/α2, α3/α4 and α5/α6) [23–25] which likely have evolved from a primitive genetic unit the proto-α1/proto-α2 resulting from duplication and inversion of a unique primitive gene with an unidirectional promoter [26–29]. Consistent with this evolutionary model the structural genes for α1,α3 and α5 on one site and α2,α4 and α6 on the other, are more closely related [26–29].

Because GPBP has been shown to bind and phosphorylate the α3(IV)NC1 domain and a similar binding to the homologous α1 and α5 NC1 domains has been found to exist [3] we searched for sequence homology between the 140-bp of POLK/COL4A3BP containing the intergene region and genomic regions expected to contain the core of each transcriptional collagen IV unit (FIG. 3). The COL4A3/COL4A4 junction (GenBank accession no AF218541) contains regions conspicuously homologous to each of the two orientations of the 140-bp yielding alignments with a high statistical significance (P<0.0001). One of the alignments (SEQ ID NO: 10 (A3 orientation) and SEQ ID NO:11 (A4 orientation) maps between the transcriptional start site of COL4A3 and one of the two alternative transcriptional start sites of COL4A4, whereas the other (SEQ ID NO: 8 (A3 orientation) and SEQ ID NO:9 (A4 orientation) is at the first intron of COL4A3 upstream of the second transcriptional start site for COL4A4. Similarly, each orientation of the 140-bp was homologous to DNA regions in the COL4A5/COL4A6 junction (GenBank accession no D28116) with alignments also highly significant (FIG. 3). One of the aligned regions (SEQ ID NO: 18 (A5 orientation) and SEQ ID NO:19 (A6 orientation) maps in between the two structural genes at the intergene region flanked by the transcriptional start site for COL4A5 and one of the two alternative transcription start sites for COL4A6, whereas the other (SEQ ID NO:20 (A5 orientation) and SEQ ID NO:21 (A6 orientation) is located upstream of the second transcription start site of COL4A6. Finally, only one region (SEQ ID NO:22 (A1 orientation) and SEQ ID NO:23 (A2 orientation) of COL4A1/COL4A2 junction (GenBank accession no M36963) aligned significantly with the orientation of the 140-bp expressing COL4A3BP (FIG. 3). Interestingly no alternative transcription start sites for COL4A2 have been reported. Although the values for Q and E(Q) in the alignment with COL4A1/COL4A2 compromises its biological significance, the preferred alignment of the 140-bp at a 127-bp region between the two 5'-UTR in COL4A1/COL4A2, in a search of 2184-bp of COL4A1/COL4A2 nucleotides, suggests that the homology is of biological significance.

Sequence homology between COL4A3BP/POLK and other bidirectional human promoters. The genomic regions representing the intergene and flanking structural genes of a number of bidirectional transcriptional units others than collagen α(IV) (GenBank accession no X66401, K01612, U00239, M96646, AJ250915 and Z68129) [30–37] were similarly analyzed for sequence homologies with the 140-bp of POLK/COL4A3BP (FIG. 4). Four out of six transcriptional units yielded statistically significant alignments at the intergene region where the corresponding core promoter is expected to map. These were LMP2/TAP1; MRP1/DHFR; HO3/HRS and HSP10/HSP60 respectively encoding low molecular mass polypeptide 2 and transporter associated with antigen processing 1; mismatch repair protein 1 and dihydrofolate reductase; histidyl-tRNA synthetase homolog and histidyl-tRNA synthetase; and, mitochondrial heat shock protein 10 and heat shock protein 60. The most remarkable alignments were those resulting from the comparison of the promoter sequence representing the orientation for COL4A3BP transcription with LMP2/TAP1 or HSP10/HSP60 transcriptional units. In the first case, among 66061-bp containing five structural genes of the MHC class II and the corresponding intergene regions the preferred alignment was in the ~600-bp at the intergene region of LMP2/TAP1 unit with a probability of 0.0002 that the homology could be found by chance. In the second case, a similar result was obtained when the search for sequence homology was done over 16986-bp which contained the two structural genes and ~550-bp of intergene region. Finally, the promoter sequence representing the orientation for POLK transcription aligned most significantly (P<0.0001) with the MRP1/DHFR junction region immediately upstream (nucleotides 704–843) (SEQ ID NO:16 (MRP1 orientation) and SEQ ID NO:17 (DHFR orientation)) of the first transcription start site for DHFR (nucleotide 844). It is also of interest to mention the statistical significance of the alignment between the transcription orientation for COL4A3BP and POLK with the first exon of HO3 and HSP60 (P<0.0001 and P=0.0013) respectively. In the case of HO3 (SEQ ID NO: 24 (HO3 orientation) and SEQ ID NO:25 (HRS orientation)), the alignment maps upstream of an alternative transcriptional start site for HRS (HRS'). Other alignments were either marginally significant and/or mapped at regions unlikely to contain a bidirectional promoter e.g. COL4A3BP orientation alignment with IDHG-TRAPD (FIG. 4).

These data demonstrate that the COL4A3BP/POLK base pair promoter sequence, which was shown to comprise a bi-directional promoter, contain sequences that are significantly homologous to a number of other known bi-directional promoters, and thus probably constitute regulatory elements shared in common by a family of bi-directional promoters.

TNF induces the POLK/COL4A3BP and COL4A3/COL4A4 promoters in transient gene expression assays. GPBP is highly expressed in apoptotic blebs in tissues undergoing autoimmune attack and is virtually not expressed in transformed cell lines [3]. Consequently to identify modulators of the transcriptional activity of POLK/COL4A3BP, a number of cytokines (TNFα, TNFβ and γIFN) with ability to cause cell death, with an anti-tumoral potential and with a role in the immune defense but also in autoimmune pathogenesis were used as inducers on cultured NIH3T3 or HeLa cells transfected with the 140-bp promoter constructs (SpromPolk and SpromGPBP). Whereas we found no effect on the transcriptional activity of the constructs when inducing the cells with IFNγ (20 ng/ml) or when inducing HeLa cells with any of the three cytokines, we found that either TNFα (10 ng/ml) or TNFβ (50 ng/ml) induced the two promoter constructs in NIH 3T3 cells (FIG. 5A), however, the induction from the 140-bp promoter was more efficient in the COL4A3BP than in the POLK direction.

To date no functional characterization of the transcriptional unit for COL4A3/COL4A4 has been reported. To explore the biological significance of sequence homology between this bidirectional promoter and the promoter of POLK/COL4A3BP (SEQ ID NOS: 6–7), we cloned each of the two orientations of the COL4A3/COL4A4 homologous regions (FIG. 3) (SEQ ID NOS:8–11) in pΦGH vector and assessed transcriptional activity in NIH3T3 cells in response to TNF (FIG. 5B). No transcriptional activity was observed in the absence of TNF treatment for any of the four constructs indicating that differently to the POLK/COL4A3BP promoter (FIG. 2) the two homologous regions in COL4A3/COL4A4 do not show constitutive transcriptional activity in NIH 3T3 cells. In contrast, when the cells were induced with TNF the two DNA regions were able to drive reporter gene expression although more efficiently for COL4A4 than for COL4A3 direction. In fact the later was only appreciable when assaying the promoter mapping at the intergene region (nucleotides 849–990 of AF218541) (SEQ ID NO:10), whereas the promoter mapping inside the COL4A3 (nucleotides 182–318 of AF218541) (SEQ ID NO:8) showed no inducible activity in this direction. In order to further support the bidirectional activity of the 849–990 region the entire intergene region flanked by the two transcriptional start sites (nucleotides 675–1045) (SEQ ID NOS:12–13) was similarly cloned and assayed. As observed for the 849–990 constructs these had not significant constitutive transcriptional activity and showed a limited response to TNF in COL4A3 direction that contrasted with the induction of the transcriptional activity in the COL4A4 direction which resulted to be significantly higher than when assaying the 849–990 construct. These results suggest the existence of two independent promoters in the DNA region that connects the 5' ends of COL4A3 and COL4A4 which respond to TNF, one bidirectional and another unidirectional. The low activity of the bidirectional promoter in the COL4A3 direction may be due to the existence of regulatory elements far apart from the core or to the lack of specific transacting factors in NIH 3T3. In any event these results suggest that the POLK/COL4A3BP and the COL4A3/COL4A4 bi-directional promoter are coordinately regulated by TNF, and verify the biological significance of the homology found between the POLK/COL4A3BP 140 base pair bi-directional promoter fragment, and the homologous promoter fragments from the COL4A3/COL4A4 promoter.

TNF induce dual homologous bidirectional promoters other than COL4A3/COL4A4. The coordinated regulation above could be understood as a part of a regulatory mechanism which depend of TNF in the context of the previously identified biological partnership of GPBP and the α chains of collagen IV [2,3], however, no immediate biological relation exists between pol κ and GPBP, and between GPBP and the products of the other bidirectional units which have been identified by sequence homology. To explore the scope of our findings we cloned and similarly assayed the 140-bp homologous DNA fragment mapping at the intergene region of LMP2/TAP1 (SEQ ID NO: 14 (LMP2 orientation) and SEQ ID NO:15 (TAP1 orientation) and HSP10/HSP60 (SEQ ID NO: 26 (HSP10 orientation) and SEQ ID NO:27 (HSP60 orientation), which represented the statistically more significant homologies (FIG. 4). Transient gene expression assays carried in NIH 3T3 cells show that whereas no transcriptional activity was found in any of the two orientation of the LMP2/TAP1 fragment (nucleotides 24579–24718 of X66401) (SEQ ID NOS: 14–15) the fragment of HSP10/HSP60 (nucleotides 3451–3590 of AJ250915) (SEQ ID NOS: 26–27) displayed both constitutive and inducible activity which was similar for each of the two orientations (FIG. 5C). Previous studies have shown that the LMP2/TAP1 unit responds to TNF and that the major transcriptional start and regulatory sites for either the two orientations in response to this cytokine mapped at the TAP1-proximal region (nucleotides 24757–24965 of X66401) [35]. However in this study the ability of this particular fragment to transcribe LMP2 in response to TNF was not assayed and therefore no direct experimental evidence was provided to rule out that the DNA region containing the homologous 140-bp indeed does not contain TNF responsive elements for LMP2 transcription, moreover, when the site at the TAP1-proximal region accounts only for the 65% of the total induction in this direction.

Figure 6:
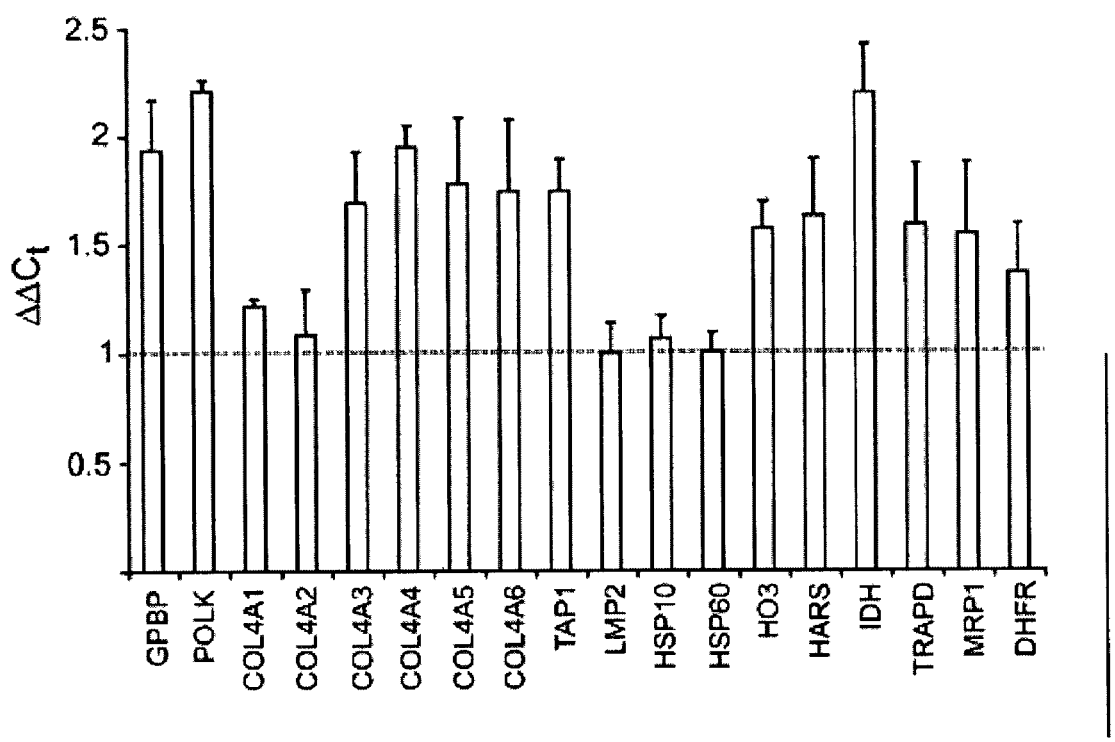
FIG. 6. TNF induction of multiple bidirectional transcriptional units in human hTERT-RPE cells. Human hTERT-RPE cells, which are retinal pigment epithelial cells immortalized by over-expression of telomerase (Clontech) were induced by TNFβ, RNA was extracted and the transcriptional activity for the indicated genes estimated by specific mRNA quantification using the Relative Quantitation Method or "ΔΔCt" as described in Materials and Methods. The values represent fold induction of induced versus non-induced cells after normalization with GAPDH mRNA values and are the mean of three different samples done by duplicated ±S.D. The MRNA levels for GAPDH were not affected by cytokine induction.

Finally the transcriptional induction of the different dual units in response to TNF was investigated in cultured human hTERT-RPE1 cells by determining mRNA levels using a Real Time PCR approach (FIG. 6). Since these cells are immortalized by over-expression of telomerase, they can be considered as primary cells, and thus more physiologically relevant than established cell lines. We have determined that these cells produce α3(IV) and GPBP. Furthermore, they are derived from retina, and retinal basement membrane contains abundant α3-α4-α5 collagen IV chains, and, similarly to glomerular basement membrane, it has been shown to contain linear deposits of autoantibodies in Goodpasture patients. In these cells TNF induced the transcription of POLK and COL4A3BP however when we assessed the level of expression of GPBP and GPBPΔ26, the two alternatively spliced products of COL4A3BP, we found that the induction depended mainly of GPBP and little induction of GPBPΔ26 was observed (not shown). The effects on the transcriptional units for the α chains of collagen IV genes varied, thus the promoter for the ubiquitous α1 and α2 chains, which displayed the less significant homology, was not inducible whereas the promoters for the α3–α6 chains with a more restricted tissue distribution and displaying the most significant alignments were induced to a similar extent and in the two transcriptional directions. The studies on dual units coding for proteins other than collagen IV α chains revealed that LMP2/TAP1 unit responded to TNF although the induction was only detected in the TAP1 direction whereas no induction of the promoter for HSP10/HSP60 was detectable in these cells. Interestingly the rest of the bidirectional units that the computer analysis showed to contain 140-bp homologous regions also were inducible by the cytokine including IDHG/TRAPD which homologous region mapped ~1.5 kb 3' of the polyadenylation signal of TRAPD. The coordinated expression of IDHG/TRAPD and POLK/COL4A3BP was also evident when the expression in different human tissues of GPBP and IDHγ was compared using standardized Northern blots (compare FIG. 2 of Ref. 2 and Ref. 37).

All these data indicate that at least for the number of genes we have reported the head-to-head arrangement is a convergent evolution phenomenon to coordinate their expression in response to TNF and that the 140-bp homologous modules contain responsive elements for the coordinated expression. Finally, our findings indicate that TNF not only induces the expression of COL4A3BP by increasing the copy number of the corresponding mRNA molecular species but also increases the relative expression of GPBP versus GPBPΔ26, a phenomenon which we have previously shown to be related with autoimmune pathogenesis [3].

Figure 7:
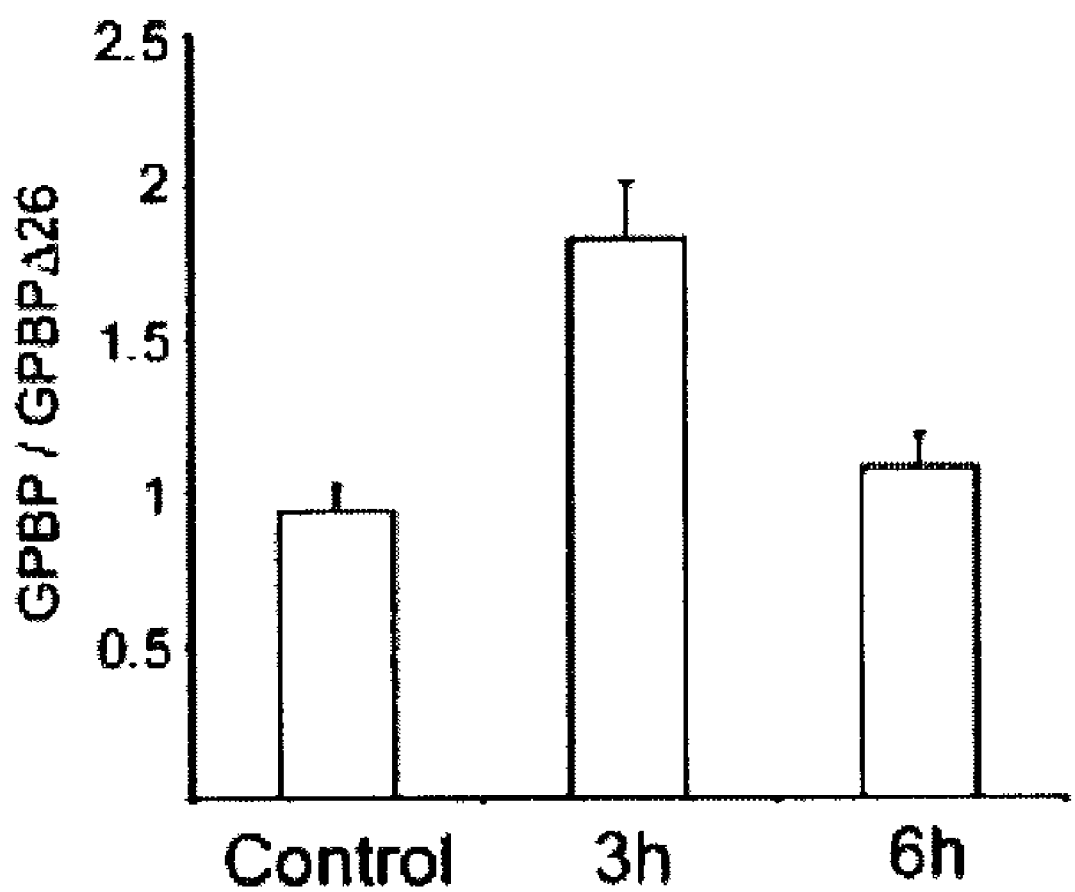
FIG. 7. Evidences for increases in the relative expression of GPBP in response to TNF in vivo. B6 mice were injected with LPS and after three or six hours the kidneys were excised, total RNA prepared and the expression level of GPBP and GPBPΔ26 determined by Real Time PCR. Non-injected mice were used in control studies. Values represent the mean±S.D. of two mice and four independent determinations.

Evidences for TNF increasing the relative expression of GPBP in vivo, a phenomenon critical for SLE development in a lupus prone mouse model. The role of TNF regulating GPBP/GPBPΔ26 ratio in the kidney was explored in B6 mice by inducing endogenous TNF production in response to LPS (FIG. 7). At the time of injection the GPBP/GPBPΔ26 values were below 1, however after three hours of LPS injection the GPBP/GPBPΔ26 ratio reached values of ~2 to finally return to near initial values after six hours of LPS injection. Contrary to what we have found when inducing hTERT-RPE1 cells the total copy number of these mRNA species with respect to the copy number of mRNA for GAPDH did not varied significantly (not shown), thus indicating that the relative increase of GPBP at the three hours was a consequence of a reduced expression levels of GPBPΔ26.

To explore the role of TNF inducing the expression of GPBP in an autoimmune response we first determined the expression of GPBP and GPBPΔ26 in a recently reported lupus prone model [15] which we have described here under Material and Methods (FIG. 8A). In this model the genetic background that predisposes female NZW to undergo SLE is "activated" by transgenic over-expression of Bcl-2 in the B cells compartment in the F1 generation which develops a severe autoimmune GN that is evident at the third month of life. We have previously reported that GPBP is poorly expressed in the kidney of Balb/c mice and that glomerular expression of GPBP was not detectable by standard immunochemical techniques [3]. Consistently we have not detected expression of GPBP in the glomerulus of the C57BL/6 (B6) male which over-express Bcl-2 transgene and we have found that in these kidneys the levels of mRNA for GPBP were lower than for GPBPΔ26 (GPBP/GPBΔ26<1). In contrast, the kidney of a NZW female expressed GPBP to a higher levels than GPBPΔ26 (GPBP/GPBPΔ26 values between 1.6 and 3.0) and contained hyaline deposits in the glomerulus which were detectable by standard immunochemical techniques using GPBP-specific antibodies. Finally, we found that in the (NZW×B6)F1 generation, and with independence of Bcl-2 transgene (Tg) expression, the GPBP/GPBPΔ26 values in the kidney were higher than in NZW (GPBP/GPBPΔ26>3.0) and showed important variations between homologous animals (GPBP/GPBPΔ26 values ranged between 3.2 and 15.5). The relative increase of GPBP however did not represent in any case (NZW or F1) an absolute increase in the mRNA copy number of GPBP which was always 5–15% of the mRNA copy number of GAPDH but rather was caused by a decrease in the expression of GPBPΔ26 (not shown). Immunohistochemical studies showed that both (NZW×B6)F1Tg(+) as well as (NZW×B6)F1Tg(-) did not express GPBP-containing hyaline deposits at the glomerulus and only the (NZW×B6)F1Tg(+) developed an autoimmune glonerulonephritis (not shown).

Treatment with anti-CD4 immediately after birth (see Material and Methods) had important consequences in both mRNA expression and immunohistochemical pattern of the (NZW×B6)F1Tg(+) (FIG. 8B). Thus the GPBP/GPBPΔ26 ratio was substantially reduced with respect to untreated animals and dropped to levels similar to those of NZW and the expression of GPBP at the glomerulus as estimated by immunohistochemistry was greatly reduced in comparison with NZW. Finally, interruption of anti-CD4 treatment for two and a half months resulted in an increase in the relative expression of GPBP in the kidney (GPBP/GPBPD26>4.0) and in the restoration of specific GPBP deposits at the glomerulus unless anti-TNF antibodies were administered, in which case the ratio GPBP/GPBPΔ26 remained down and the presence of GPBP-conataining deposits at the glomerulus was not detectable by immunohistochemical techniques (FIG. 8B). Histological evaluation of the kidneys revealed that as expected early treatment with anti-CD4 prevented development of GN whereas interruption of this treatment resulted in a progressive restoration of the GN unless the anti-TNF program was started in which case the consequences were unequal, one mouse did not developed GN whereas the other showed a more severe nephritis.

To investigate the consequences that the immunological treatment had on the autoimmune response the levels of anti-ssDNA autoantibodies in the sera (a standard and very sensitive marker for autoimmunity) of six month old (NZW×B6)F1Tg(-) or (NZW×B6)F1Tg(+) maintained untreated, were compared with the levels of these autoantibodies in (NZW×B6)F1Tg(+) treated with anti-CD4 for three months and either untreated or treated with anti-TNF for three additional months (FIG. 8C). As expected (NZW×B6)F1Tg(-) showed levels of autoantibodies in the background range (0.1–0.5) whereas untreated (NZW×B6)F1Tg (+) showed elevated titers of autoantibodies (1.0–2.2 OD). Treatment of the (NZW×B6)F1Tg(+) for three months with anti-CD4 and further maintained with anti-TNF up to six months efficiently inhibited the autoimmune response as estimated by the maintenance of autoantibodies level at the background range. In contrast the (NZW×B6)F1Tg(+) which were kept untreated for three months after the anti-CD4 treatment displayed autoantibodies values in between the untreated and the anti-TNF treated suggesting that the autoimmune response starts as the T cell population increases, unless anti-TNF is added, in which case the autoimmune response remains silent.

From all these data we conclude that the autoimmune response in the lupus prone model studied is mediated by TNF and operates through an elevated ratio of GPBP/GPBPΔ26.

Molecular cloning of a 76-kDa alternatively spliced variant of DNA polymerase κ. Alternatively spliced variants of pol κ have been reported to exist in human and mouse testis [5]. The presence in HeLa and in human striated muscle of molecular species with different 5'-UTR (see above) also indicated the presence of molecular species representing alternatively spliced variants previously unrecognized. We have use RT-PCR on total human RNA from foreskin and we have cloned a previously unidentified mRNA species for pol κ. This novel mRNA species contain a 672-residue open reading frame predicting pol κ76, a 76-kDa pol κ isoform (GenBank accession no AF315602) (SEQ ID NO:31), which represents an alternatively exon splicing variant that diverged with respect to the alternatively spliced isoforms previously identified in that exon skipping does not cause a reading frame shift but eliminates the bulk of the sequence predicting two in tandem helix-hairpin-helix domains and a coiled-coil motif characteristic of the primary product (FIG. 9A).

Figure 10:
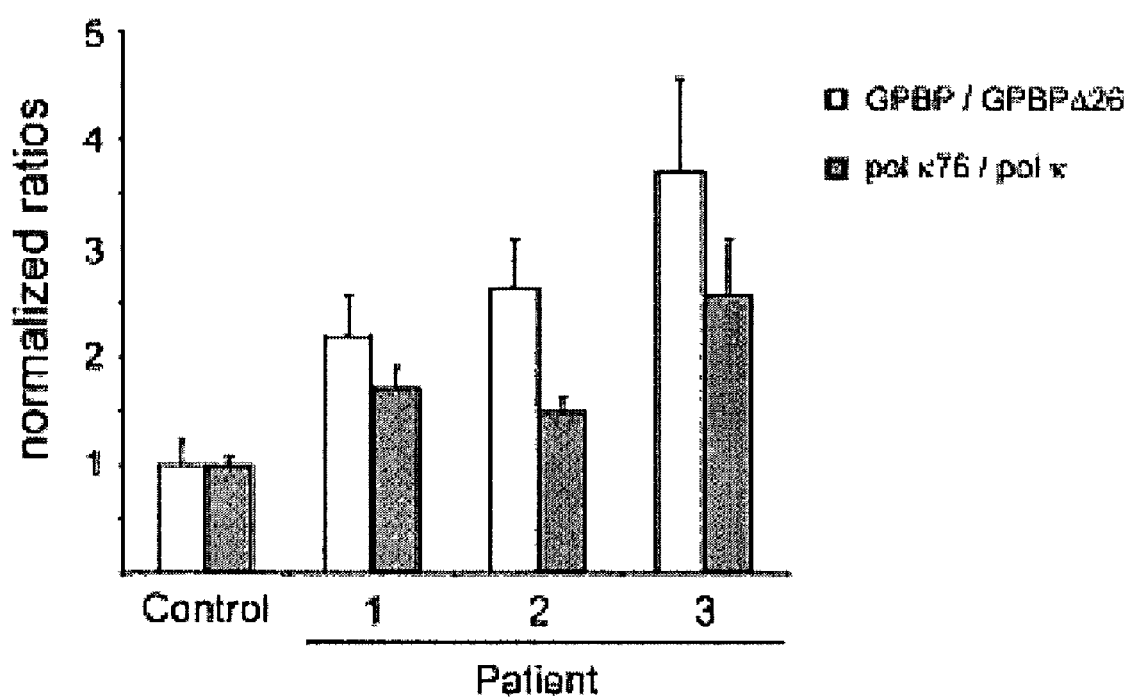
FIG. 10. The relative expression of pol κ76 and GPBP with respect to their alternative isoforms pol κ and GPBPΔ26 is augmented in cutaneous lupus. The expression of pol κ76, pol κ, GPBP and GPBPΔ26 was determined by Real Time PCR in reverse transcriptase mixtures of human foreskin (Control) or skin affected of cutaneous lupus (Patient 1–3). The indicated ratio values were normalized with respect to control ratio values that were set at 1. Values represent the mean±S.D. of two determinations. In addition to clinical diagnosis all the patients samples had histological diagnosis confirmation and showed lineal deposits of immunocomplexes at the dermal-epidermal junction in direct immunofluorescence, which is characteristic of cutaneous lupus.

To estimate the relative expression of this novel molecular species in human tissues we performed specific Real Time PCR on several cDNA libraries or reverse transcriptase reactions from human tissues (FIG. 9B). Pol κ76 resulted to be a minor form which was comparatively more abundant in skin and in keratinocytes than in the rest of the tissues studied. The relative higher expression in the keratinocytes of the skin, a cell with an ongoing apoptotic program required for adequate maturation, prompted the idea that pol κ76 may be part of the cell machinery involved in the apoptotic program in which GPBP has been proposed to be involved in these cells [3]. We have investigated using a yeast two hybrid system the existence of protein-protein interactions between pol κ/pol κ76 and GPBP/GPBPΔ26 and we got no positive results (unpublished observations). However, we demonstrated that pol κ76 interacts with a protein that also interacts with GPBP/GPBPΔ26 (not shown). This data further suggests that GPBP and pol κ76 are partners in specific apoptotic pathways relevant in keratinocyte maturation and which become deregulated during autoimmune pathogenesis. We have previously reported that in the skin undergoing autoimmune attack there is a relative increase in the expression of GPBP with respect to GPBPΔ26 therefore resulting in increased values for the GPBP/GPBPΔ26 ratio [3], and suggesting that during pathogenesis changes in the exon splicing pattern of COL4A3BP also occur. In order to assess if this condition applies for POLK gene expression, affected skin from patients undergoing cutaneous lupus were individually RNA extracted and the mRNA levels for pol κ, pol κ76, GPBP and GPBPΔ26 measured. We have found that in these patients elevated pol κ76/pol κ ratios correlated with elevated ratios of GPBP/GPBPΔ26 (FIG. 10).

Discussion

In normal human tissues GPBP is expressed at a lower level than GPBPΔ26, an alternatively spliced variant devoid of 26-residues serine-rich motif which represents a less active isoform of the protein kinase [3]. Although GPBP and GPBPΔ26 are widely expressed in human tissues they show a preferential expression in cells and tissue structures which are the target of common autoimmune responses. [2,3]. These isoforms represent two different strategies to regulate the activity of a common catalytic domain, and several lines of evidence indicate that homeostasis is achieved by a balanced expression of each isoform, whereas a breakage of the homeostasis caused by a relative increase in GPBP expression results in autoimmune pathogenesis [3].

GPBP is expressed at very low levels in cancer cells and is highly expressed in apoptotic blebs of differenced keratinocytes at the periphery of normal epidermis [3]. Keratinocytes from patients suffering from skin autoimmune processes show an increased sensitivity to UV-induced apoptosis, and a premature apoptosis at the basal keratinocytes has been reported to occur in these patients [38–41]. Consistently, we have found GPBP to be expressed in apoptotic bodies expanding from basal to peripheral strata in epidermis undergoing an autoimmune attack [3]. Altered autoantigens including phosphorylated versions thereof have been reported to be produced and released from these apoptotic bodies [40]. All these suggest that GPBP is part of an apoptotic-mediated strategy for desired cell removal that generates aberrant counterparts of critical cell components and operates illegitimately during autoimmune pathogenesis [3].

It has been shown that dinB1 (pol IV) and the eukaryotic counterpart pol κ induces spontaneous mutation on undamaged DNA [4,6,7], likely as a result of a high error nucleotide incorporation rates and an efficient mismatch extension [7]. The latter feature largely depends on the formation of a primer-template misalignment that generates –1 frameshift products [4,6].

The coordinated expression of COL4A3BP and POLK demonstrated herein suggest that the products encoded by these genes are partners in specific cell program(s), and that pol κ may represent a somatic mutation-based strategy to generate structural diversity which in some instances, such as in keratincocytes could be used to generate aberrant counterparts of critical cellular components as part of an apoptotic strategy. The disruption of the coordinated expression of the two genes during cell transformation (see Northern blot results) and its maintenance at higher levels in autoimmune affected tissues further supports the implication pol κ/κ76 in apoptotic strategies relevant in autoimmune pathogenesis. Finally, disruption of transcriptional coordination of POLK and COL4A3BP may be required in cancer to prevent cell death but also autoimmune attack during tumor growth.

Alternative exon splicing of the pre-mRNA of pol κ serves to generate three different types of mRNA products. Transcripts encoding truncated forms of the polymerase contain divergent, shortened C-termini that are devoid of the Zn clusters and bipartite nuclear localization signals [5], and therefore are expected to play a regulatory role in the expression or activity of the primary pol κ product rather than to represent an alternative replicating enzyme. Transcripts with alternative 5'-UTR, essentially differing from each other in the nucleotide sequence at the vicinity of the translation start site, may represent mRNAs translated with different efficiency or molecules with different stability.

Pol κ76 is the first member of the UmuC/DinB superfamily that contains the N-terminal nucleotidyl transferase domain, but lacks the helix-hairpin-helix motifs and the predictable coiled-coil structure at the C-terminal conserved domain. This isoform retains the Zn clusters for DNA binding also existing in other family members devoid of nucleotidyl transferase domain, but with demonstrated DNA repair activity (Rab18 and Snm1) [5]. The helix-hairpin-helix has been implicated in non-specific binding to DNA and the coiled-coil structure could mediate protein-protein interactions. The fact that pol κ76 still harbors the critical structural requirements for DNA polymerase, and also maintain those characteristic of the DNA repair related enzymes, suggest that pol κ76 may represent the version of pol κ to generate aberrant counterparts of critical cell components in the context of a common apoptotic-mediated strategy for a desired cell removal, similarly to the proposed role for GPBP versus GPBPΔ26 in keratinocyte apoptosis. [3]

Multiple sclerosis is an autoimmune disorder with a complex mode of inheritance. A genome search has suggested co-segregation of a locus for this disease with the marker D5S815 [42]. Whereas this marker maps at positions 79000 Kbp and 81556 Kbp from the telomere according to GeneMap (http://www.ncbi.nlm.nih.gov/genome/guide), POLK, and consequently COL4A3BP, maps to position 80300 Kbp. This, in addition to the other data presented above and in WO 00/50607, suggests that the expression products of the POLK and GPBP genes play a role in human autoimmunity.

We show here that each orientation of a 140 base pair fragment of the bi-directional promoter for POLK/COL4A3BP is highly homologous to DNA regions at the gene junctions of a variety of bi-directional promoters. The sequence homology found among different intergene regions transcribing structurally unrelated genes, as well as the TNF-induced coordinated expression of these genes, likely reflect a strategy to link the expression of proteins that are partners in complex biological programs. Furthermore, we have shown that this 140 base pair fragment and homologous regions in other bi-directional units contain the structural requirements to initiate transcription and to respond to TNF.

Our data suggest that the presence of elevated GPBP/GPBPΔ26 ratios is not sufficient to develop an autoimmune response, since NZW and (NZW×B6)F1Tg(–) do not produce autoantibodies. Rather, the data support the view that elevated GPBP/GPBPΔ26 ratios represent part of the genetic trait that predisposes NZW female and the (NZW×B6)F1 generation to develop an autoimmune response. In our model, normal apoptosis of autoreactive cells is prevented by over-expressing Bcl-2 in the B cell compartment, and mice are placed into the pathogenic condition that triggers the autoimmune response [15]. To be effective, the autoimmune response requires T cell assistance, as anti-CD4 treatment prevented autoantibody production. Furthermore, the inhibition of autoantibody production by the immunological blockade of TNF, one of the cytokines produced by TH1 cells, suggests that these subset of the T cells plays a critical role in the autoimmune response.

Anti-TNF treatment decreased GPBP/GPBPΔ26 ratios in the animal model, and LPS induction of endogenous production of TNF increased the GPBP/GPBPΔ26 ratios in the kidney of B6 mice, suggesting that TNF is a major regulator of the GPBP/GPBPΔ26 ratio in vivo. Since in our animal model, elevated GPBP/GPBPΔ26 ratios are required for the autoantibody production to occur, it seems that TNF induction mediates the autoimmune response in part by increasing the GPBP/GPBPΔ26 ratio. Consistent with this idea, suspension of anti-CD4 treatment in (NZW×B6)F1Tg(+) results in an increase in the GPBP/GPBPΔ26 ratios and autoantibody production, unless treatment with anti-TNF is restored, in which case both GPBP/GPBPΔ26 ratios and autoantibodies remain down.

Goodpasture kidneys express elevated GPBP/GPBPΔ26 ratios, and the autoantibodies mediating this autoimmune GN recognize aberrantly folded counterparts of the autoantigen, suggesting that elevated levels of GPBP are responsible for the aberrant production of autoantigen. Consistently, GPBP, but not GPBPΔ26, catalyzes the in vitro synthesis of conformational species of the autoantigen, which are characteristic of a Goodpasture kidney (not shown).

Without being bound by any proposed mechanism, the totality of the evidence suggests that NZW and the subsequent F1 generation, which inherited the expression mode of COL4A3BP, are continually producing a number of aberrant components, which only in the case of F1Tg(+) promotes an autoimmune response because of the presence of an increased repertoire of autoreactive B cells in the periphery. In this scenario, the autoimmune response can be understood as an epiphenomenon of a clinically low penetrating cell disorder which, because of its deleterious consequences in renal function, becomes the protagonist. According to this idea, we have found important histological changes at the glomerulus of NZW mainly consisting of eosinophile PAS positive hyaline deposits, which are likely to be the substrate for antibody binding in the immunohistochemical studies (not shown). These deposits exist in the absence of an open autoimmune response in NZW, whereas they would be accompanied by production of autoantibodies in the F1Tg (+) when anti-CD4 treatment is abandoned.

The mechanism by which NZW expresses elevated GPBP/GPBPΔ26 ratios is presently unknown. However, the failure of anti-TNF treatment to lower the GPBP/GPBPΔ26 ratios in the F1Tg(+) generation to the levels of B6 suggests that this mode of expression of COL4A3BP is constitutive, rather than depending on an enhanced TNF response, and therefore that the constitutive GPBP/GPBPΔ26 ratios are under the control of additional factors. In this scenario, TNF induction during the autoimmune response could have an enhanced response, reaching GPBP/GPBPΔ26 ratios much higher than expected for the gene expression mode of B6, leading to a cooperative deleterious effect between the autoimmune response and abnormally high GPBP/GPBPΔ26 ratios.

Anti-TNF based therapeutic approaches have been shown to be effective in several autoimmune conditions including rheumatoid arthritis and Crohn's disease and is presently at the stage of critical clinical trials [12,43]. Anti-TNF based therapy has been shown also to have important therapeutic effects on experimental allergic encephalomyelitis (EAE), an animal model for multiple sclerosis, however similar therapeutic approach in human clinical trials resulted in clinical worsening [12]. In our case, although the animals treated maintained the autoantibody levels one developed a GN more aggressive than untreated animals and mice in which anti-TNF treatment was extended for one additional month showed more abundant histological damage and very high GPBP/GPBPΔ26 ratios (not shown).

All the evidences above suggest that, in our model, the anti-TNF treatment is likely operating over the autoimmune response, and is very effective at inhibiting autoantibody production. However, likely because the cytokine is expected to be high in the pathogenic cascade and is known to be involved in various biological functions [12], anti-TNF treatment appears to have limitations. The coordinated expression of the multiple bi-directional promoters in response to TNF and the coordinated elevation of the GPBP/GPBPΔ26 and pol κ76/pol κ ratios in human cutaneous lupus suggest that bi-directional promoters are partners in apoptotic programs which become upregulated during autoimmune pathogenesis. Consequently, an intervention at the transcriptional level over common trans-acting factor(s) likely represent a way to achieve therapeutic effects on the autoimmune response with less site effects than anti-TNF based therapy.

REFERENCES

1. Saus, J. (1998) in *Goodpasture's Syndrome: Encyclopedia of Immunology* 2nd edn. Vol. 2, eds. Delves, P. J., & Roitt, I. M., (Academic Press Ltd., London),pp. 1005–1011.
2. Raya, A., Revert, F., Navarro, S., and Saus, J. (1999) Characterization of a novel type of serine/threonine kinase that specifically phosphorylates the human Goodpasture antigen J. Biol. Chem. 274, 12642–12649.
3. Raya, A., Revert-Ros, F., Martinez-Martinez, P., Navarro, S., Roselló, E., Vieites, B., Granero, F., Forteza, J. and Saus, J. (2000) Goodpasture antigen-binding protein, the kinase that phosphorylates the Goodpasture antigen, is an alternatively spliced variant implicated in autoimmune pathogenesis. J. Biol. Chem. 275, 40392–40399.
4. Wagner, J., Gruz, P., Kim, S. -R., Yamada, M., Matsui, K., Fuchs, R. P. P. and Nohmi, T.(1999) The dinB gene encodes a novel *E. coli* DNA polymerase, DNA Pol IV, involved in mutagenesis. Mol. Cell 4, 281–286.
5. Gerlach, V. L., Aravind, L., Gotway, G., Schultz, R. A., Koonin, E. V. and Friedberg, E. C.(1999) Human and mouse homologs of *E. coli* DinB (DNA polymerase IV), members of the UmuC/DinB superfamily. Proc. Natl. Acad. Sci. USA 96, 11922–11927.
6. Johnson, R. E., Prakash, S. and Prakash, L.(2000) The human DINB1 gene encodes the DNA polymerase polθ. Proc. Natl. Acad. Sci. USA 97, 3838–3843.
7. Tang, M., Pham, P., Shen, X., Taylor, J. -S., O'Donnell, M., Woodgate, R. and Goodman, M. F. (2000) Roles of the *E.coli* DNA polymerases IV and V in lesion-targeted and untargeted SOS mutagenesis. Nature 404, 1014–1018.
8. Ohashi, E., Bebenek, K., Matsuda, T., Feaver, W. J., Gerlach, V. L., Friedberg, E. C., Ohmori, H. and Kunkel, T. A.(2000) Fidelity and processivity of DNA synthesis by DNA polymerase κ, the product of the human DINB1 gene. J. Biol. Chem. 275, 39678–39684.

9. Zhang, Y., Yuan, F., Xin, H., Wu, X., Rajpal, D. K., Yang,D. and Wang, Z.(2000) Human DNA polymerase κ synthesizes DNA with extraordinarily low fidelity. Nucleic Acids Res. 28, 4147–4156.
10. Zhang, Y., Yuan, F., Wu, X., Wang, M., Rechkoblit, O., Taylor, J. -S., Geacintov, N. E. and Wang, Z.(2000) Error-free and error-prone lesion bypass by human DNA polymerase κ in vitro. Nucleic Acids Res. 28, 4138–4146.
11. Gerlach, V. L., Feaver, W. J., Fischhaber, P. L., and Friedberg, E. C.(2001) Purification and characterization of pol κ, a DNA polymerase encoded by the human DINB1 gene. J. Biol. Chem. 276, 92–98.
12. Oppenheim, J. J and Feldmann, M.(2001) in *Cytokine Reference. A compedium of cytokines and other mediators of host defense* Vol. 1 (Academic Press Ltd.,London), pp 413–447.
13. Nadal, M., Moreno, S., Pritchard, M., Preciado, M. A., Estivill, X., and Ramos-Arroyo, M. A.(1997) Down syndrome: characterisation of a case with partial trisomy of chromosome 21 owing to a paternal balanced translocation (15;21) (q26;q22.1) by FISH. J. Med. Genet. 34, 50–54.
14. Needleman, S. B. and Wunsch, C. D. (1970) A general method applicable to the search for similarities in the amino acid sequence of two proteins. J. Mol. Biol. 48, 443–453.
15. López-Hoyos, M., Diez, M. A., Buelta, L., Izui, S., Merino J., and Merino, R.(1999) Overexpression of human Bcl-2 in germinal center B cells induce a new and severe autoimmune syndrome in (C57BL/6×NZW)F1 mice. Arthritis Rheum. 42(9):S393.
16. Gonzalez M, Schurmans S, Ramos A, Merino R, Lambert P -H and Merino J. (1995) CD4+ T cells determine the ability of spleen cells from F1 hybrid mice to induce neonatal tolerance to alloantigens and autoimmunity in parental mice. Eur. J. Immunol. 25: 1760–1764.
17. López-Hoyos, M., Carrió, R., Merino, R., Buelta, L., Izui, S., Núñez, G., and Merino, J.(1996). Constitutive expression of Bcl-2 in B cells causes a lethal form of lupuslike autoimmune disease after induction of neonatal tolerance to H-2$^b$ alloantigens. J. Exp. Med. 183, 2523–2531.
18. Echtenacher B, Falk W, Mannel D A and Krammer P H (1990) Requirement of endogenous Tumor Necrosis Factor/Cachectin for recovery from experimental peritonitis. J. Immunol. 145, 3762–3766
19. Remick D, Manohar P, Bolgos G, Rodriguez J, Moldawer L, and Wollenberg G. (1995) Blockade of tumor necrosis factor reduces lipopolysaccharide lethality, but not the lethality of cecal ligation and puncture. Shock, 4, 89–95.
20. Wasylyk, B., Wasylyk, C., Augereau, P. and Chambon, P.(1983) The SV40 72 bp repeat preferentially potentiates transcription starting from proximal natural or substitute promoter elements. Cell 32, 503–514.
21. Hansen, U. and Sharp, P. (1983) Sequences controlling in vitro transcription of SV40 promoters. EMBO J. 2, 2293–2303.
22. Lavia, P., Macleod, D. and Bird, A. (1987) Coincident start sites for divergent transcripts at a randomly selected CpG-rich island of mouse. EMBO J. 6, 2773–2779.
23. Pöschl, E., Pollner, R. and Künh, K. (1988) The genes for the α1(IV) and α2(IV) chains of human basement membrane collagen type IV are arranged head-to-head and separated by a bi-directional promoter of unique structure. EMBO J. 7, 2687–2695.
24. Momota, R., Sugimoto, M., Oohashi, T., Kigasawa, K., Yoshioka, H. and Ninomiya, Y.(1998) Two genes, COL4A3 and COL4A4 coding for the human α3(IV) and α4(IV) collagen chains are arranged head-to-head on chromosome 2q36. FEBS Lett. 424, 11–16.
25. Sugimoto, M., Oohashi, T., and Ninomiya, Y. (1994) The genes COL4A5 and COL4A6, coding for basement membrane collagen chains α5(IV) and α6(IV), are located head-to-head in close proximity on chromosome Xq22 and COL4A6 is transcribed from two alternative promoters. Proc. Natl. Acad. Sci. USA 91, 11679–11683.
26. Quinones, S., Bernal, D., Garcia-Sogo, M., Elena, S. F. and Saus, J. (1992) Exon/intron structure of the human α3(IV) gene encompassing the Goodpasture antigen (α3 (IV)NC1). J. Biol. Chem. 267, 19780–19784.
27. Mariyama, M., Kalluri, R. , Hudson, B. G. and Reeders, S. T. (1992) The α4(V) chain of basement membrane collagen. J. Biol. Chem. 267, 1253–1258.
28. Sugimoto, M., Oohashi, T., Yoshioka, H., Matsuo, N., and Ninomiya, Y. (1993). cDNA isolation and partial gene structure of the human α4(IV)collagen chain. FEBS Lett. 330, 122–128.
29. Oohashi, T., Ueki, Y., Sugimoto, M. and Ninomiya, Y.(1995). Isolation and structure of the COL4A6 gene encoding the human α6(IV) collagen chain and comparison with other type IV collagen genes. J. Biol. Chem. 270, 26863–26867.
30. Shimada, T, Fujii, H. and Lin, H. (1989) A 165-base pair sequence between the dihydrofolate reductase gene and the divergently transcribed upstream gene is sufficient for bi-directional transcriptional activity. J. Biol. Chem. 264, 20171–20174.
31. Shinya, E. and Shimada, T. (1994) Identification of two initiator elements in the bi-directional promoter of the human dihydrofolate reductase and mismatch repair protein 1 genes. Nucleic Acids Res. 22, 2143–2149.
32. O'Hanlon, T. P., Raben, N., and Miller F. W. (1995) A novel gene oriented in a head-to-head configuration with the human histidyl-tRNA synthetase (HRS) gene encodes an mRNA that predicts a polypeptide homologous to HRS. Biochem. Biophys. Res. Commun. 210, 556–566.
33. Tsui, H. W., Mok, S., Souza, L., Marttin, A., and Tsui, F. W. L.(1993) Transcriptional analyses of the gene region that encodes the human histidyl-tRNA synthetase: Identification of a novel bi-directional regulatory element. Gene 131, 201–208.
34. Gavalas, A. and Zalkin, H. (1995) Analysis of the chicken GPAT/AIRC bi-directional promoter for de novo purine nucleotide synthesis. J. Biol. Chem. 270, 2403–2410.
35. Wright, K. L., White, L. C., Kelly, A., Beck, S., Trowsdale, J., and Ting, J. P. -Y. (1995) Coordinate regulation of the human TAP1 and LMP2 genes from a shared bi-directional promoter. J. Exp. Med. 181, 1459–1471.
36. Ryan, M. T., Herd, S. M., Sberna, G., Samuel, M. M., Hoogenraad, N. J. and Hoj, P. B. (1997) The genes encoding mammalian chaperonin 60 and chaperonin 10 are linked head-to-head and share a bi-directional promoter. Gene 196, 9–17.
37. Brenner, V., Nyakatura, G., Rosenthal, A. and Platzer, M. (1997) Genomic organization of two novel genes on human Xq28:Compact head to head arrangement of IDHγ and TRAPδ is conserved in rat and mouse. *Genomics* 44, 8–14.
38. Casciola-Rosen, L. A., Anhalt, G. and Rosen, A. (1994) Autoantigens targeted in systemic lupus erythematosus are clustered in two populations of surface structures on apoptotic keratinocytes. J. Exp. Med. 179, 1317–1330.

39. Casciola-Rosen, L., & Rosen, A. (1997) Ultraviolet light-induced keratinocyte apoptosis: a potential mechanism for the induction of skin lesions and autoantibody production in LE. Lupus 6, 175–180.

40. Utz, P. J., and Anderson, P. (1998) Posttranslational protein modifications, apoptosis, and the bypass of tolerance to autoantigens. Arthritis & Rheum. 41, 1152–1160.

41. Pablos, J. L:, Santiago, B., Galindo, M., Carreira, P. E., Ballestin, C. and Gomez-Reino, J. J. (1999) Keratinocyte apoptosis and p53 expression in cutaneous lupus and dermatomyositis. J. Pathol. 188, 63–68.

42. The Multiple Sclerosis Genetics Group (1996) A complete genomic screen for multiple sclerosis underscores a role for the major histocompatability complex. Nature Genet. 13, 469–471.

43. Felmann, M., Bondeson, J., Brennan, F. M., Foxwell, B. M., and Maini, RN.(1999). The rationale for the current boom in anti-TNFα treatment. Is there an effective means to define therapeutic targets for drugs that provide all the benefits of anti-TNFα and minimise hazards? Ann. Rheum. Dis. 58 Suppl1, I27–31.

I claim:

1. A tumor necrosis-factor inducible promoter, consisting of an isolated nucleic acid sequence selected from the group consisting of SEQ ID NO:6, and SEQ ID NO:7.

2. An expression vector comprising one or more of the tumor necrosis-factor inducible promoters of claim 1.

3. The expression vector of claim 2 further comprising a polylinker adjacent to the 3' end of the one or more tumor necrosis-factor inducible promoters.

4. The expression vector of claim 2 comprising two or more of the tumor necrosis-factor inducible promoters.

5. The expression vector of claim 4 further comprising a polylinker adjacent to the 3' end of each of the two or more tumor necrosis-factor inducible promoters.

6. The expression vector of claim 2 further comprising a reporter gene operatively linked to the one or more of the tumor necrosis-factor inducible promoters.

7. The expression vector of claim 4 further comprising a reporter gene operatively linked to the two or more of the tumor necrosis-factor inducible promoters.

8. An isolated host cell transfected with one or more of the expression vector of claim 2.

9. An isolated host cell transfected with one or more of the expression vector of claim 3.

10. An isolated host cell transfected with one or more of the expression vector of claim 4.

11. An isolated host cell transfected with one or more of the expression vector of claim 5.

12. An isolated host cell transfected with one or more of the expression vector of claim 6.

13. An isolated host cell transfected with one or more of the expression vector of claim 7.

* * * * *